US012709739B2

(12) United States Patent
Zhang et al.

(10) Patent No.: US 12,709,739 B2
(45) Date of Patent: Aug. 18, 2026

(54) ENGINEERED CELLS SECRETING THERAPEUTIC ENZYMES

(71) Applicant: Cartesian Therapeutics, Inc., Gaithersburg, MD (US)

(72) Inventors: Yi Zhang, Gaithersburg, MD (US); C. Andrew Stewart, Frederick, MD (US); Shaji Daniel, Germantown, MD (US); Metin Kurtoglu, Bethesda, MD (US); Murat V. Kalayoglu, Silver Spring, MD (US)

(73) Assignee: Cartesian Therapeutics, Inc., Frederick, MD (US)

( * ) Notice: Subject to any disclaimer, the term of this patent is extended or adjusted under 35 U.S.C. 154(b) by 862 days.

(21) Appl. No.: 17/919,092

(22) PCT Filed: Apr. 15, 2021

(86) PCT No.: PCT/US2021/027489
§ 371 (c)(1),
(2) Date: Oct. 14, 2022

(87) PCT Pub. No.: WO2021/211848
PCT Pub. Date: Oct. 21, 2021

(65) Prior Publication Data

US 2023/0174944 A1 Jun. 8, 2023

Related U.S. Application Data

(60) Provisional application No. 63/047,516, filed on Jul. 2, 2020, provisional application No. 63/010,489, filed on Apr. 15, 2020.

(51) Int. Cl.
*C12N 5/0775* (2010.01)
*C07K 16/28* (2006.01)
*C12N 9/22* (2006.01)

(52) U.S. Cl.
CPC ........ *C12N 5/0662* (2013.01); *C07K 16/2878* (2013.01); *C12N 9/22* (2013.01); *C12Y 301/21001* (2013.01)

(58) Field of Classification Search
None
See application file for complete search history.

(56) References Cited

U.S. PATENT DOCUMENTS

2014/0199329 A1 7/2014 Wagner et al.
2014/0287509 A1 9/2014 Sharei et al.
2017/0218355 A1 8/2017 Buie et al.
2019/0030129 A1 1/2019 Schrum et al.
2019/0263920 A1 8/2019 Vu et al.
2020/0024585 A1 1/2020 Fuchs et al.
2023/0072226 A1* 3/2023 Fox ...................... C12Q 1/6806

FOREIGN PATENT DOCUMENTS

WO WO 90/05144 A1 5/1990
WO WO 2009/142767 A1 11/2009
WO WO 2019/036719 A2 2/2019
WO WO 2019/099639 A1 5/2019

OTHER PUBLICATIONS

Ullah et al. Iscience 15 (2019): 421-438. (Year: 2019).*
Balyasnikova et al. Journal of tissue engineering and regenerative medicine 4.4 (2010): 247-258. (Year: 2010).*
Friedman et al. Human gene therapy 29.5 (2018): 585-601. (Year: 2018).*
Davis et al., Recombinant human Dnase I (rhDNase) in patients with lupus nephritis. Lupus. 1999;8(1):68-76. doi: 10.1191/096120399678847380.
Macanovic et al., The treatment of systemic lupus erythematosus (SLE) in NZB/W F1 hybrid mice; studies with recombinant murine DNase and with dexamethasone. Clin Exp Immunol. Nov. 1996;106(2):243-52. doi: 10.1046/j.1365-2249.1996.d01-839.x.
Ullah et al., Mesenchymal Stromal Cell Homing: Mechanisms and Strategies for Improvement. iScience. May 31, 2019;15:421-438. doi: 10.1016/j.isci.2019.05.004. Epub May 9, 2019.
Extended European Search Report, mailed Apr. 15, 2024 for European Application No. 21789568.9.
Carpenter et al., B-cell maturation antigen is a promising target for adoptive T-cell therapy of multiple myeloma. Clin Cancer Res. Apr. 15, 2013;19(8):2048-60. doi: 10.1158/1078-0432.CCR-12-2422. Epub Jan. 23, 2013.
Gupta et al., The role of neutrophils and NETosis in autoimmune and renal diseases. Nat Rev Nephrol. Jul. 2016;12(7):402-13. doi: 10.1038/nrneph.2016.71. Epub May 31, 2016. Author Manuscript, 28 pages.
Oliveri et al., DNase I behaves as a transcription factor which modulates Fas expression in human cells. Eur J Immunol. Jan. 2004;34(1):273-9. doi: 10.1002/eji.200223817.
International Search Report and Written Opinion, mailed Aug. 6, 2021 for International Application No. PCT/US2021/027489.
International Preliminary Report on Patentability, mailed Oct. 27, 2022 for International Application No. PCT/US2021/027489.
Bird et al., Single-chain antigen-binding proteins. Science. Oct. 21, 1988;242(4877):423-6. doi: 10.1126/science.3140379. Erratum in: Science Apr. 28, 1989;244(4903):409.
Burgener et al., Extracellular Traps in Host Defense. Cold Spring Harb Perspect Biol. Jul. 1, 2020;12(7):a037028. doi: 10.1101/cshperspect.a037028.

(Continued)

*Primary Examiner* — Maria Marvich
*Assistant Examiner* — Brendan Thomas Tinsley
(74) *Attorney, Agent, or Firm* — Wolf, Greenfield & Sacks, P.C.

(57) ABSTRACT

Provided herein are mammalian cells comprising a first exogenous nucleic acid encoding a DNAse protein and a second exogenous nucleic acid encoding another DNAse protein, such as DNASE1 protein and DNASE1L3 protein, that have improved properties, including the ability to degrades extracellular chromatin and remove Neutrophil Extracellular Traps (NETs). Use of these cells, including the use in the treatment of a subject in need thereof, is also contemplated.

15 Claims, 11 Drawing Sheets

Specification includes a Sequence Listing.

(56) References Cited

OTHER PUBLICATIONS

Geurts et al., Gene transfer into genomes of human cells by the sleeping beauty transposon system. Mol Ther. Jul. 2003;8(1):108-17. doi: 10.1016/s1525-0016(03)00099-6.

Holliger et al., "Diabodies": small bivalent and bispecific antibody fragments. Proc Natl Acad Sci U S A. Jul. 15, 1993;90(14):6444-8. doi: 10.1073/pnas.90.14.6444.

Huston et al., Protein engineering of antibody binding sites: recovery of specific activity in an anti-digoxin single-chain Fv analogue produced in *Escherichia coli.* Proc Natl Acad Sci U S A. Aug. 1988;85(16):5879-83. doi: 10.1073/pnas.85.16.5879.

Keyel, P.A., Dnases in health and disease. Dev Biol. Sep. 1, 2017;429(1):1-11. doi: 10.1016/j.ydbio.2017.06.028. Epub Jun. 28, 2017.

Neumann et al., Extracellular Traps: An Ancient Weapon of Multiple Kingdoms. Biology (Basel). Feb. 18, 2020;9(2):34. doi: 10.3390/biology9020034.

Nishikawa et al., Nonviral vectors in the new millennium: delivery barriers in gene transfer. Hum Gene Ther. May 20, 2001;12(8):861-70. doi: 10.1089/104303401750195836.

Poljak, R.J., Production and structure of diabodies. Structure. Dec. 15, 1994;2(12):1121-3. doi: 10.1016/s0969-2126(94)00113-8.

Spiess et al., Alternative molecular formats and therapeutic applications for bispecific antibodies. Mol Immunol. Oct. 2015;67(2 Pt A):95-106. doi: 10.1016/j.molimm.2015.01.003. Epub Jan. 27, 2015.

Ward et al., Binding activities of a repertoire of single immunoglobulin variable domains secreted from *Escherichia coli.* Nature. Oct. 12, 1989;341(6242):544-6. doi: 10.1038/341544a0.

Espiritu et al., A Web of Challenges: The Therapeutic Struggle to Target NETs in Disease. Int J Mol Sci. May 16, 2025;26(10):4773. doi: 10.3390/ijms26104773.

* cited by examiner a b c d 1000 bp
500 bp
200 bp
100 bp

ENGINEERED CELLS SECRETING THERAPEUTIC ENZYMES

This application is a national stage filing under 35 U.S.C. § 371 of International PCT Application PCT/US2021/027489, filed Apr. 15, 2021, which claims priority under 35 U.S.C. § 119(e) to U.S. Provisional Patent Application, U.S. Ser. No. 63/010,489, filed on Apr. 15, 2020, and U.S. Provisional Patent Application, U.S. Ser. No. 63/047,516, filed on Jul. 2, 2020, the entire content of both each of which is incorporated herein by reference.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 13, 2022, is named C154070002US02-SEQ-AZW and is 72,998 bytes in size.

BACKGROUND

Neutrophil Extracellular Traps (NETs) are extracellular webs of chromatin, i.e., DNA and associated nuclear proteins, released by neutrophils in a controlled process called NETosis. NETs were discovered only 16 years ago but have since been recognized as a fundamental and biologically ancient component of innate immunity and host defense. See Neumann A. et al., Extracellular traps: an ancient weapon of multiple kingdoms, *Biology* 2020, doi 10.3390/biology9020034; Burgener S. et al., Neutrophil Extracellular Traps in host defense, *Cold Spring Harb Perspect Biol.* 2019, doi 10.1101/cshperspect.a037028.

NETs have also been implicated as key mediators in a wide array of acute and chronic diseases, e.g., acute respiratory distress syndrome (ARDS), acute kidney injury (AKI), sepsis, myocardial infarction, systemic lupus erythematosus (SLE), rheumatoid arthritis (RA), systemic sclerosis (SS), asthma, and various cancers. See, e.g., Keyel P. A., DNAses in health and disease, *Dev. Biol.* 2017, doi 10.1016/j.ydbio.2017.06.028; Fuchs T. A. et al., Neutrophil Extracellular Traps, *Inflammation* 2018, doi 10/1142/9789813198445_0006.

There has been much interest in therapies to remove NETs to treat or prevent human disease. One such therapy is the therapeutic administration of exogenously produced DNAse enzymes, e.g., DNAse 1 (DNASE1) or DNAse 1-like-3 (DNASE1L3), to an individual in need thereof. See, e.g., U.S.S.N. 2014/0199329 and U.S.S.N. 2020/0024585

There are many challenges and shortcomings, however, to the manufacture and administration of exogenously produced DNAse enzymes. For example, such enzymes are difficult to manufacture, not least because they can be toxic to cells customarily used for recombinant expression. Most DNAse enzymes are rapidly eliminated from the systemic circulation; and they can be immunogenic.

Therefore, a new approach for the therapeutic removal of NETs.

SUMMARY OF THE INVENTION

The present invention arises from the inventors' discovery that a mammalian cell, e.g., a human Natural Killer (NK) cell or Mesenchymal Stem (or Stromal) Cell (MSC), can be modified in vitro to secrete one or more DNAse enzymes that remove NETs, and that such a cell can be administered to an individual in need thereof for therapeutic or prophylactic purposes. The DNAse enzymes can be, e.g., DNASE1L3, DNASE1, another DNAse, or a combination thereof. There are several potential benefits to this approach. For example, with reference to MSCs: (1) MSCs cells naturally home to sites of inflammation within the body, such as the lungs in patients with Acute Respiratory Distress Syndrome (ARDS). Thus, in contrast to systemic administration of an enzyme, which provides uniform enzyme concentrations in the bloodstream, MSCs will deliver the enzyme in close proximity to the inflamed tissue where NETs are concentrated. (2) MSCs can be produced from a separate donor for safe "off-the-shelf" administration to one or more recipients different from the donor, without risk of an adverse host immune response. This makes it possible to manufacture the cells economically, in bulk, and in advance, so that they can be immediately available when needed. (3) The MSCs can be modified to express and secrete one or more native DNAse enzymes by introduction of recombinant RNA or DNA, and the resultant DNAse enzyme(s) will have all the normal post-translational modifications that render them identical to the native enzyme. This stands in contrast to the usual industrial production of DNAse enzymes in *E. coli*, yeast, insect, or mammalian cell lines, which is not only costly and labor-intensive, but can also yield products that differ from the native enzyme, for example, due to differences in post-translational modification. These potential benefits are meant to be non-limiting and the disclosed invention would still be beneficial without one or more of these potential benefits.

The invention also embraces other cells, including, but not limited to, homospecific cells, e.g., blood cells (e.g., T cells, NK cells, monocytes, macrophages or CD34+ cells), or other stem cells, modified in vitro to produce one or more DNAse enzymes to remove NETs.

Where the invention describes cells modified to secrete one or more DNAse enzymes, it is also envisioned that any of those cells may be further modified to express one or more additional proteins. For example, the cells described herein can be further modified to express an anti-BCMA protein. B cell maturation antigen (BCMA) is a tumor necrosis family receptor (TNFR) member expressed in cells of the B cell lineage. BCMA expression is the highest on terminally differentiated B cells, e.g., plasma cells. BCMA is involved in mediating the survival of plasma cells for maintaining long-term humoral immunity. Therefore, BCMA-positive cells also play an important role in certain cancers, e.g., myeloma and Hodgkin lymphoma, and diseases mediated by auto-antibodies, e.g., myasthenia gravis, systemic lupus erythematosus, rheumatoid arthritis, blistering skin diseases (e.g., pemphigus, psoriasis), inflammatory bowel disease, celiac sprue, pernicious anemia, idiopathic thrombocytopenia purpura, scleroderma, Graves' disease, Sjögren syndrome, Goodpasture syndrome, and type 1 diabetes. In some conditions where both auto-antibodies and NETs play a role, e.g., systemic lupus erythematosus, the ability to reduce or remove both NETs and BCMA+ cells would be of particular value. Indeed, the inventors envision that simultaneous reduction of NETs and BCMA+ cells would provide synergistic benefits in the aforementioned conditions, especially systemic lupus erythematosus. For purposes of this disclosure, an "anti-BCMA protein" means a protein that specifically binds to BCMA. Preferably, the anti-BCMA protein causes reduction of BCMA+ cells. The anti-BCMA protein can be, e.g., an anti-BCMA monoclonal antibody; or a bispecific antibody, e.g., a bispecific T-cell engager, e.g., directed against each of BCMA and CD3. See, e.g., U.S. Pat. Pub. No. 2019/0263920A1.

Furthermore, the invention includes not only the inventive cells, but also specific constructs or vectors used in production of the inventive cells, methods to produce the inventive cells, methods of treatment that comprise administration of the inventive cells to an individual in need thereof, and uses of the inventive cells for the treatment or prevention of disease.

BRIEF DESCRIPTION OF THE DRAWINGS

FIG. 4A represents DNase1 mRNA. FIG. 4B represents DNase1L3 mRNA.

FIG. 5A represents DNase1 protein expression. FIG. 5B represents DNase1L3 protein expression at Day 1. No expression was evident at Day 2-6.

FIG. 6D shows a fluorescent micrograph of NETs induced from human neutrophils by incubating with 100 μg/mL of phorbol myristate acetate (PMA).

FIG. 7C shows a representative fluorescence micrograph of NETs cultured overnight in the presence of 100,000 MSC or 100,000 GR-17 (highest concentration). Background image settings are identical between control and GR-17 conditions and the images are at the same magnification.

DEFINITIONS

Figures 1, 2:
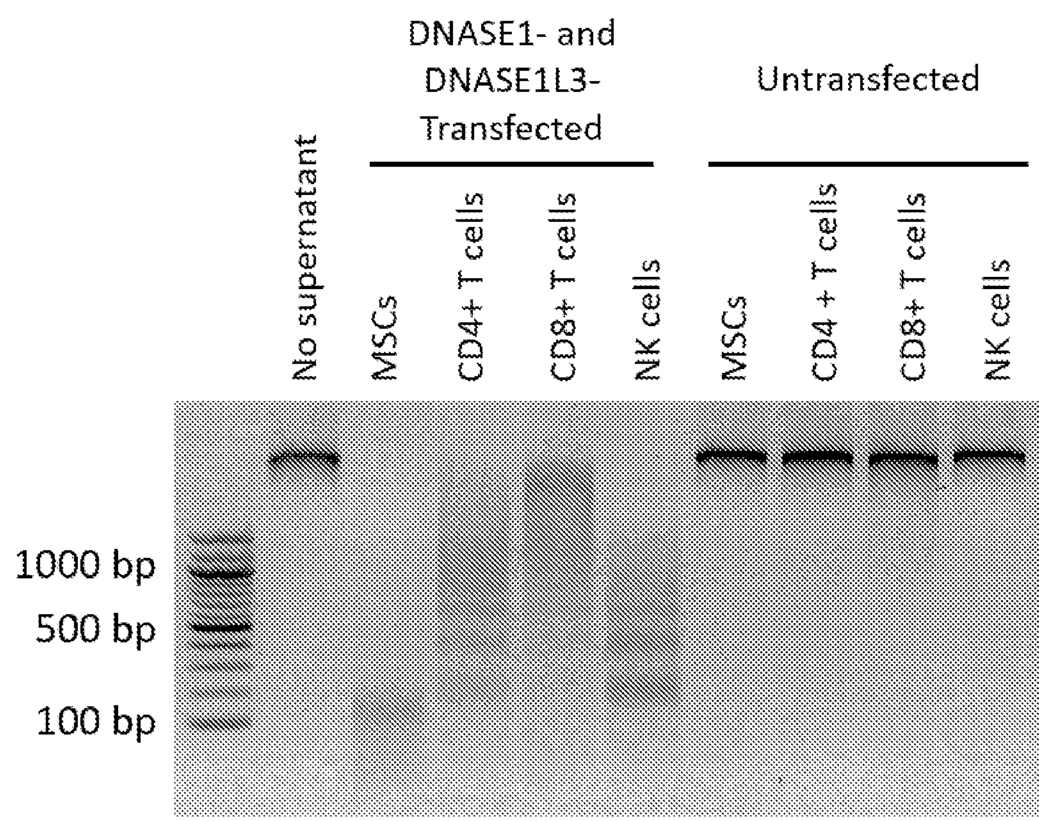
FIG. 1 shows the results of a chromatin degradation assay with DNA electrophoresis following treatment of chromatin with supernatants of cells transfected with DNASE1 and DNASE1L3, or cells that were untransfected. The cells used in this assay were MSCs, CD4+ T cells, CD8+ T cells, and NK cells.
FIG. 2 shows the results of a chromatin degradation assay with DNA electrophoresis following treatment of chromatin with MSC supernatant samples. Lane A represents unmodified MSCs. Lane B represents MSCs modified to express DNASE1. Lane C represents MSCs modified to express DNASE1L3 (by means of a pseudouridine-substituted mRNA). Lane D represents MSCs modified to express both DNASE1 and DNASE1L3.

As used herein and in the claims, the singular forms "a," "an," and "the" include the singular and the plural reference unless the context clearly indicates otherwise. Thus, for example, a reference to "an agent" includes a single agent and a plurality of such agents.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multi-specific formats; specifically binding to two or more different antigens. Multispecific, dual specific, and bispecific antibody constructs are well known in the art and described and characterized in Kontermann (ed.), Bispecific Antibodies, Springer, NY (2011), and Spiess et al., Mol. Immunol. 67(2):96-106 (2015).

Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations, kappa and lambda light chains refer to the two major antibody light chain isotypes.

The term "synthetic antibody" as used herein, refers an antibody which is generated using recombinant DNA technology, such as, for example, an antibody expressed by a viral vector. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

An "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include, but are not limited to, those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Unless otherwise specified, where used in reference to a nucleic acid or nucleic acid construct, "exogenous" refers to a nucleic acid or nucleic acid construct that originates from outside a cell and is introduced into the cell by one more artificial manipulations.

An exogenous nucleic acid can include, without limitation, nucleic acid analogs, unnatural and/or modified nucleotides, and other modifications known in the art, including, without limitation, 5' caps or other covalently linked chemical moieties known in the art.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence or nucleic acid encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo, ex vivo or in vitro.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner. A "constitutive" promoter is a nucleotide sequence which, when operably linked with a polynucleotide which encodes or specifies a gene product, causes the gene product to be produced in a cell under most or all physiological conditions of the cell.

The terms "patient," "subject," "individual," and the like are used interchangeably herein, and refer to any animal, or cells thereof whether in vitro or in situ, amenable to the methods described herein. In some embodiments, the patient, subject or individual is a human. Examples of subjects include humans, dogs, cats, mice, rats, and transgenic species thereof. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject has a NET-mediated or NET-associated condition or disease (e.g., ARDS). In other embodiments, the subject is a healthy volunteer.

By "NETs" is meant Neutrophil Extracellular Traps, which are extracellular webs of chromatin, i.e., DNA and associated nuclear proteins, released by neutrophils in a controlled process called, e.g., NETosis.

Where used with respect to pseudouridine, the terms "substituted" or "substitution" refer to an RNA wherein one or more pseudouridine nucleotides occupy sequence position(s) that are otherwise described as occupied, or otherwise would be occupied, by uridine(s) in one or more nucleic acid sequences or embodiments described or referenced herein, including those uridine(s) implied to occur in RNAs that are complementary to any DNA sequence described or referenced herein. For example, of the sum of uridine and pseudouridine nucleotides in a particular nucleic acid, pseudouridine can account for at least 50%, at least 60%, at least 70%, at least 80%, at least 90%, at least 95%, at least 97%, at least 99%, at least 99.5%, or at least 99.9%. In some embodiments where substantially all positions that would otherwise be occupied by uridines are occupied by pseudouridines, at least 90%, at least 95%, at least 97%, at least 99%, at least 99.5%, or at least 99.9% of such positions are occupied by pseudouridines.

The term "therapeutic" as used herein means a treatment and/or prophylaxis. A therapeutic effect is obtained by suppression, remission, or eradication of a disease state.

As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

DETAILED DESCRIPTION OF CERTAIN EMBODIMENTS

Sequences

The following amino acid (AA) or nucleotide (nt) sequences are referenced herein:

```
SEQ ID NO: 1 (human DNASE1; AA sequence)
MRGMKLLGALLALAALLQGAVSLKIAAFNIQTFGETKMSNATLVSYIVQILSRYDIALVQEVRDS
HLTAVGKLLDNLNQDAPDTYHYVVSEPLGRNSYKERYLFVYRPDQVSAVDSYYYDDGCEPCGNDT
FNREPAIVRFFSRFTEVREFAIVPLHAAPGDAVAEIDALYDVYLDVQEKWGLEDVMLMGDFNAGC
SYVRPSQWSSIRLWTSPTFQWLIPDSADTTATPTHCAYDRIVVAGMLLRGAVVPDSALPFNFQAA
YGLSDQLAQAISDHYPVEVMLK

SEQ ID NO: 2 (human DNASE1L3; AA sequence)
MSRELAPLLLLLLSIHSALAMRICSFNVRSFGESKQEDKNAMDVIVKVIKRCDIILVMEIKDSNN
RICPILMEKLNRNSRRGITYNYVISSRLGRNTYKEQYAFLYKEKLVSVKRSYHYHDYQDGDADVF
SREPFVVWFQSPHTAVKDFVIIPLHTTPETSVKEIDELVEVYTDVKHRWKAENFIFMGDFNAGCS
YVPKKAWKNIRLRTDPRFVWLIGDQEDTTVKKSTNCAYDRIVLRGQEIVSSVVPKSNSVFDFQKA
YKLTEEEALDVSDHFPVEFKLQSSRAFTNSKKSVTLRKKTKSKRS

SEQ ID NO: 3 (human DNASE1-T2A-human DNASE1L3; AA sequence)
MRGMKLLGALLALAALLQGAVSLKIAAFNIQTFGETKMSNATLVSYIVQILSRYDIALVQEVRDS
HLTAVGKLLDNLNQDAPDTYHYVVSEPLGRNSYKERYLFVYRPDQVSAVDSYYYDDGCEPCGNDT
FNREPAIVRFFSRFTEVREFAIVPLHAAPGDAVAEIDALYDVYLDVQEKWGLEDVMLMGDFNAGC
```

-continued

SYVRPSQWSSIRLWTSPTFQWLIPDSADTTATPTHCAYDRIVVAGMLLRGAVVPDSALPFNFQAA
YGLSDQLAQAISDHYPVEVMLKEGRGSLLTCGDVEENPGPMSRELAPLLLLLLSIHSALAMRICS
FNVRSFGESKQEDKNAMDVIVKVIKRCDIILVMEIKDSNNRICPILMEKLNRNSRRGITYNYVIS
SRLGRNTYKEQYAFLYKEKLVSVKRSYHYHDYQDGDADVFSREPFVVWFQSPHTAVKDFVIIPLH
TTPETSVKEIDELVEVYTDVKHRWKAENFIFMGDFNAGCSYVPKKAWKNIRLRTDPRFVWLIGDQ
EDTTVKKSTNCAYDRIVLRGQEIVSSWPKSNSVFDFQKAYKLTEEEALDVSDHFPVEFKLQSSR
AFTNSKKSVTLRKKTKSKRS

SEQ ID NO: 4 (transmembrane IL15; AA sequence)
MALPVTALLLPLALLLHAARPNWVNVISDLKKIEDLIQSMHIDATLYTESDVHPSCKVTAMKCFL
LELQVISLESGDASIHDTVENLIILANNSLSSNGNVTESGCKECEELEEKNIKEFLQSFVHIVQM
FINTSFVPVFLPAKPTTTPAPRPPTPAPTIASQPLSLRPEACRPAAGGAVHTRGLDFACDIYIWA
PLAGTCGVLLLSLVITLYCNHRNGGSDYKDDDDK SEQ ID NO: 5 (IL15-TGFbeta fusion protein; AA sequence)
MGWSCIILFLVATATGVHSDYKDDDDKTIPPHVQKSVNNDMIVTDNNGAVKFPQLCKFCDVRFST
CDNQKSCMSNCSITSICEKPQEVCVAVWRKNDENITLETVCHDPKLPYHDFILEDAASPKCIMKE
KKKPGETFFMCSCSSDECNDNIIFSEEYNTSNPDTIPPHVQKSVNNDMIVTDNNGAVKFPQLCKF
CDVRFSTCDNQKSCMSNCSITSICEKPQEVCVAVWRKNDENITLETVCHDPKLPYHDFILEDAAS
PKCIMKEKKKPGETFFMCSCSSDECNDNIIFSEEYNTSNPDGTGGSSGITCPPPMSVEHADIWVK
SYSLYSRERYICNSGFKRKAGTSSLTECVLNKATNVAHWTTPSLKCIRDPALVHQRPAPPSGGSG
GGGSGGGSGGGGSLQNWVNVISDLKKIEDLIQSMHIDATLYTESDVHPSCKVTAMKCFLLELQVI
SLESGDASIHDTVENLIILANNSLSSNGNVTESGCKECEELEEKNIKEFLQSFVHIVQMFINTS SEQ ID NO: 6 (IL15-TGFbeta fusion protein, alternate; AA
sequence)
MGWSCIILFLVATATGVHSDYKDDDDKNWVNVISDLKKIEDLIQSMHIDATLYTESDVHPSCKVT
AMKCFLLELQVISLESGDASIHDTVENLIILANNSLSSNGNVTESGCKECEELEEKNIKEFLQSF
VHIVQMFINTSGTGGSSGITCPPPMSVEHADIWVKSYSLYSRERYICNSGFKRKAGTSSLTECVL
NKATNVAHWTTPSLKCIRDPALVHQRPAPPSGGSGGGGSGGGSGGGGSLQTIPPHVQKSVNNDMI
VTDNNGAVKFPQLCKFCDVRFSTCDNQKSCMSNCSITSICEKPQEVCVAVWRKNDENITLETVCH
DPKLPYHDFILEDAASPKCIMKEKKKPGETFFMCSCSSDECNDNIIFSEEYNTSNPDTIPPHVQK
SVNNDMIVTDNNGAVKFPQLCKFCDVRFSTCDNQKSCMSNCSITSICEKPQEVCVAVWRKNDENI
TLETVCHDPKLPYHDFILEDAASPKCIMKEKKKPGETFFMCSCSSDECNDNIIFSEEYNTSNPD SEQ ID NO: 7 (Influenza NS1; AA sequence)
MDSNTVSSFQVDCFLWHVRKQVADQELGDAPFLDRLRRDQKSLKGRGSTLGLNIETATCVGKQIV
ERILKEESDEAFRMTMASALASRYLTDMTIEEMSRDWFMLMPKQKVAGPLCVRMDQAIMDKNIIL
KANFSVIFDRLETLTLLRAFTEEGAIVGEISPLPSLPGHTNEDVKNAIGVLIGGLEWNDNTVRVS
ETLQRFAWRSSNENGGPPLTPTQKRKMAGKIRSEV SEQ ID NO: 8 (Vaccinia E3; AA sequence)
MSKIYIDERSDAEIVCAAIKNIGIEGATAAQLTRQLNMEKREVNKALYDLQRSAMVYSSDDIPPR
WFMTTEADKPDADAMADVIIDDVSREKSMREDHKSFDDVIPAKKIIDWKDANPVTIINEYCQITK
RDWSFRIESVGPSNSPTFYACVDIDGRVFDKADGKSKRDAKNNAAKLAVDKLLGYVIIRF SEQ ID NO: 9 (Human XBP1-iso2; AA sequence)
MVVVAAAPNPADGTPKVLLLSGQPASAAGAPAGQALPLMVPAQRGASPEAASGGLPQARKRQRLT
HLSPEEKALRRKLKNRVAAQTARDRKKARMSELEQQVVDLEEENQKLLLENQLLREKTHGLVVEN
QELRQRLGMDALVAEEEAEAKGNEVRPVAGSAESAAGAGPVVTPPEHLPMDSGGIDSSDSESDIL
LGILDNLDPVMFFKCPSPEPASLEELPEVYPEGPSSLPASLSLSVGTSSAKLEAINELIRFDHIY
TKPLVLEIPSETESQANVVVKIEEAPLSPSENDHPEFIVSVKEEPVEDDLVPELGISNLLSSSHC
PKPSSCLLDAYSDCGYGGSLSPFSDMSSLLGVNHSWEDTFANELFPQLISV SEQ ID NO: 10 (DP71L; AA sequence)
MGGRRRKKRTNDTKHVRFAAAVEVWEADDIERKGPWEQVAVDRFRFQRRIASVEELLSTVLLRQK
KLLEQQ SEQ ID NO: 11 (PP1-GADD34 eIF2a binding protein; AA sequence)
MSDSEKLNLDSIIGRLLEVQGSRPGKNVQLTENEIRGLCLKSREIFLSQPILLELEAPLKICGDI
HGQYYDLLRLFEYGGFPPESNYLFLGDYVDRGKQSLETICLLLAYKIKYPENFFLLRGNHECASI
NRIYGFYDECKRRYNIKLWKTFTDCFNCLPIAAIVDEKIFCCHGGLSPDLQSMEQIRRIMRPTDV
PDQGLLCDLLWSDPDKDVQGWGENDRGVSFTFGAEVVAKFLHKHDDLICRAHQVVEDGYEFFAKR
QLVTLFSAPNYCGEFDNAGAMMSVDETLMCSFQILKPADKNKGKYGQFSGLNPGGRPITPPRNSA
KAKKARQGPWEQLARDRSREARRITQAQEELSPCLTPAARARAWA SEQ ID NO: 12 (B18R; AA sequence)
MGTMKMMVHIYFVSLLLLLFHSYAIDIENEITEFFNKMRDTLPAKDSKWLNPACMFGGTMNDIAA
LGEPFSAKCPPIEDSLLSHRYKDYVVKWERLEKNRRRQVSNKRVKHGDLWIANYTSKFSNRRYLC
TVTTKNGDCVQGIVRSHIRKPPSCIPKTYELGTHDKYGIDLYCGILYAKHYNNITWYKDNKEINI
DDIKYSQTGKELIIHNPELEDSGRYDCYVHYDDVRIKNDIVVSRCKILTVIPSQDHRFKLILDPK
INVTIGEPANITCTAVSTSTSLLIDDVLIEWENPSGWLIGFDFDVYSVLTSRGGITEATLYFENVTE
EYIGNTYKCRGHNYYFEKTLTTTVVLE SEQ ID NO: 13 (IRES; Internal Ribosomal Entry Site; nt sequence)
Gcggccatcgatgtcgacaactaacttaagctagcaacggtttccctctagcgggatcaattccg
cccccccccctaacgttactggccgaagccgcttggaataaggccggtgtgcgtttgtctatat
gttattttccaccatattgccgtcttttggcaatgtgagggcccggaaacctggccctgtcttct
tgacgagcattcctaggggtctttcccctctcgccaaaggaatgcaaggtctgttgaatgtcgtg -continued aaggaagcagttcctctggaagcttcttgaagacaaacaacgtctgtagcgaccctttgcaggca
gcggaacccccccacctggcgacaggtgcctctgcggccaaaagccacgtgtataagatacacctg
caaaggcggcacaaccccagtgccacgttgtgagttggatagttgtggaaagagtcaaatggctc
tcctcaagcgtattcaacaaggggctgaaggatgcccagaaggtaccccattgtatgggatctga
tctggggcctcggtgcacatgctttacatgtgtttagtcgaggttaaaaaaacgtctaggccccc
cgaaccacggggacgtggttttcctttgaaaaacacgataataccaattcgccgccacc SEQ ID NO: 14 (T2A; AA sequence)
EGRGSLLTCGDVEENPGP SEQ ID NO: 15 (5'UTR of pSFVC vector; nt sequence)
atggcggatgtgtgacatacacgacgccaaaagattttgttccagctcctgccacctccgctacg
cgagagattaaccacccacg SEQ ID NO: 16 (3'UTR of pSFVC vector; nt sequence)
taataaccgggcagggggatcccgggtaattaattgaattacatccctacgcaaacgttttacg
gccgccggtggcgcccgcgcccggcggcccgtccctggccgttgcaggccactccggtggctccc
gtcgtccccgacttccaggcccagcagatgcagcaactcatcagcgccgtaaatgcgctgacaat
gagacagaacgcaattgctcctgctaggcctcccaaaccaaagaagaagaagacaaccaaaccaa
agccgaaaacgcagcccaagaagatcaacggaaaaacgcagcagcaaaagaagaaagacaagcaa
gccgacaagaagaagaagaaacccggaaaaagagaaagaatgtgcatgaagattgaaaatgactg
tatctatgcggctagccacagtaacgtagtgtttccagacatgtcgggcaccgcactatcatggg
tgcagaaaatctcgggtggtctgggggccttcgcaatcggcgctatcctggtgctggttgtggtc
acttgcattgggctccgcagataagttagggtaggcaatggcattgatatagcaagaaaattgaa
aacagaaaaagttagggtaagcaatggcatataaccataactgtataacttgtaacaaagcgcaa
caagacctgcgcaattggccccgtggtccgcctcacggaaactcggggcaactcatattgacaca
ttaattggcaataattggaagcttacataagcttaattcgacgaataattggatttttattttat
tttgcaattggtttttaatatttcc SEQ ID NO: 17 (NSP1-NSP4; AA sequence)
MAAKVHVDIEADSPFIKSLQKAFPSFEVESLQVTPNDHANARAFSHLATKLIEQETDKDTLILDI
GSAPSRRMMSTHKYHCVCPMRSAEDPERLVCYAKKLAAASGKVLDREIAGKITDLQTVMATPDAE
SPTFCLHTDVTCRTAAEVAVYQDVYAVHAPTSLYHQAMKGVRTAYWIGFDTTPFMFDALAGAYPT
YATNWADEQVLQARNIGLCAASLTEGRLGKLSILRKKQLKPCDTVMFSVGSTLYTESRKLLRSWH
LPSVFHLKGKQSFTCRCDTIVSCEGYVVKKITMCPGLYGKTVGYAVTYHAEGFLVCKTTDTVKGE
RVSFPVCTYVPSTICDQMTGILATDVTPEDAQKLLVGLNQRIVVNGRTQRNTNTMKNYLLPIVAV
AFSKWAREYKADLDDEKPLGVRERSLTCCCLWAFKTRKMHTMYKKPDTQTIVKVPSEFNSFVIPS
LWSTGLAIPVRSRIKMLLAKKTKRELIPVLDASSARDAEQEEKERLEAELTREALPPLVPIAPAE
TGVVDVDVEELEYHAGAGVVETPRSALKVTAQPNDVLLGNYVVLSPQTVLKSSKLAPVHPLAEQV
KIITHNGRAGRYQVDGYDGRVLLPCGSAIPVPEFQALSESATMVYNEREFVNRKLYHIAVHGPSL
NTDEENYEKVRAERTDAEYVFDVDKKCCVKREEASGLVLVGELTNPPFHEFAYEGLKIRPSAPYK
TTVVGVFGVPGSGKSAIIKSLVTKHDLVTSGKKENCQEIVNDVKKHRGLDIQAKTVDSILLNGCR
RAVDILYVDEAFACHSGTLLALIALVKPRSKVVLCGDPKQCGFFNMMQLKVNFNHNICTEVCHKS
ISRRCTRPVTAIVSTLHYGGKMRTTNPCNKPIIIDTTGQTKPKPGDIVLTCFRGWVKQLQLDYRG
HEVMTAAASQGLTRKGVYAVRQKVNENPLYAPASEHVNVLLTRTEDRLVWKTLAGDPWIKVLSNI
PQGNFTATLEEWQEEHDKIMKVIEGPAAPVDAFQNKANVCWAKSLVPVLDTAGIRLTAEEWSTII
TAFKEDRAYSPVVALNEICTKYYGVDLDSGLFSAPKVSLYYENNHWDNRPGGRMYGFNAATAARL
EARHTFLKGQWHTGKQAVIAERKIQPLSVLDNVIPINRRLPHALVAEYKTVKGSRVEWLVNKVRG
YHVLLVSEYNLALPRRRVTWLSPLNVTGADRCYDLSLGLPADAGRFDLVFVNIHTEFRIHHYQQC
VDHAMKLQMLGGDALRLLKPGGSLLMRAYGYADKISEAVVSSLSRKFSSARVLRPDCVTSNTEVF
LLFSNFDNGKRPSTLHQMNTKLSAVYAGEAMHTAGCAPSYRVKRADIATCTEAAVVNAANARGTV
GDGVCRAVAKKWPSAFKGEATPVGTIKTVMCGSYPVIHAVAPNFSATTEAEGDRELAAVYRAVAA
EVNRLSLSSVAIPLLSTGVFSGGRDRLQQSLNHLFTAMDATDADVTIYCRDKSWEKKIQEAIDMR
TAVELLNDDVELTTDLVRVHPDSSLVGRKGYSTTDGSLYSYFEGTKFNQAAIDMAEILTLWPRLQ
EANEQICLYALGETMDNIRSKCPVNDSDSSTPPRTVPCLCRYAMTAERIARLRSHQVKSMVVCSS
FPLPKYHVDGVQKVKCEKVLLFDPTVPSVVSPRKYAASTTDHSDRSLRGFDLDWTTDSSSTASDT
MSLPSLQSCDIDSIYEPMAPIVVTADVHPEPAGIADLAADVHPEPADHVDLENPIPPPRPKRAAY
LASRAAERPVPAPRKPTPAPRTAFRNKLPLTFGDFDEHEVDALASGITFGDFDDVLRLGRAGAYI
FSSDTGSGHLQQKSVRQHNLQCAQLDAVEEEKMYPPKLDTEREKLLLLKMQMHPSEANKSRYQSR
KVENMKATVVDRLTSGARLYTGADVGRIPTYAVRYPRPVYSPTVIERFSSPDVAIAACNEYLSRN
YPTVASYQITDEYDAYLDMVDGSDSCLDRATFCPAKLRCYPKHHAYHQPTVRSAVPSPFQNTLQN
VLAAATKRNCNVTQMRELPTMDSAVFNVECFKRYACSGEYWEEYAKQPIRITTENITTYVTKLKG
PKAAALFAKTHNLVPLQEVPMDRFTVDMKRDVKVTPGTKHTEERPKVQVIQAAEPLATAYLCGIH
RELVRRLNAVLRPNVHTLFDMSAEDFDAIIASHFHPGDPVLETDIASFDKSQDDSLALTGLMILE
DLGVDQYLLDLIEAAFGEISSCHLPTGTRFKFGAMMKSGMFLTLFINTVLNITIASRVLEQRLTD
SACAAFIGDDNIVHGVISDKLMAERCASWVNMEVKIIDAVMGEKPPYFCGGFIVFDSVTQTACRV
SDPLKRLFKLGKPLTAEDKQDEDRRRALSDEVSKWFRTGLGAELEVALTSRYEVEGCKSILIAMA
TLARDIKAFKKLRGPVIHLYGGPRLVR SEQ ID NO: 18 (26S Promoter; nt sequence)
tacacagaattctgattatagcgcactattatagcaccatgaattacatccctacgcaaacgttt
tacggccgccggtggcgcccgcgcccggcggcccgtccctggccgttgcaggccactccg SEQ ID NO: 19 (C Protein fragment; AA sequence)
VAPVVPDFQAQQMQQLISAVNALTMRQNAIAPARPPKPKKKKTTKPKPKTQPKKINGKTQQQKKK
DKQADKKKKKPGKRERMCMKIENDCIFEVKHEGKVTGYACLVGDKVMKPAHVKGVIDNADLAKLA
FKKSSKYDLECAQIPVHMRSDASKYTHEKPEGHYNWHHGAVQYSGGRFTIPTGAGKPGDSGRPIF
DNKGRVVAIVLGGANEGSRTALSVVTWNKDMVTRVTPEGSEEWDP -continued

```
SEQ ID NO: 20 (Kozak Sequence; nt sequence)
gccgccaccatga

SEQ ID NO: 21 (anti-BCMA, anti-CD3 bispecific T-cell engager,
with signal sequence)
MYRMQLLSCIALSLALVTNSDIVLTQSPASLAVSPGQRATITCRASESVSFLGINLIHWYQQKPG
QPPKLLIYSASNLQSGVPARFSGSGSGTDFTLTISSVEPEDTANYYCLQSRTLPRTFGQGTKVEI
KGSTSGSGKPGSGEGSTKGQIQLVQSGPELKKPGGSVKISCKASGYTFTSYSINWVRQAPGKGLE
WVGWINTETREPAYAQGFTGRFTFSADTSKSMAYLQINSLRAEDTAVYYCALDYLYSLDFWGQGT
LVTVSSGGGGSQVQLVQSGAEVKKPGASVKVSCKASGYTFTRYTMHWVRQAPGQGLEWIGYINPS
KGYTNYNQKFKGRVTMTADKSTSTAYMELSSLRSEDTAVYYCARYYDDHYSLDYWGQGTLVTVSS
GGGGSGGGGSGGGGSGGGGSEIVMTQSPATLSVSPGERATLSCRASSSVSYLNWYQQKSGTSPKR
WIYDTSKVASGVPYRFSGSGSGTDFTLTISSLQAEDEATYYCQQWSSNPLTFGQGTKLEIK

SEQ ID NO: 22 (anti-BCMA, anti-CD3 bispecific T-cell engager,
without signal sequence)
DIVLTQSPASLAVSPGQRATITCRASESVSFLGINLIHWYQQKPGQPPKLLIYSASNLQSGVPAR
FSGSGSGTDFTLTISSVEPEDTANYYCLQSRTLPRTFGQGTKVEIKGSTSGSGKPGSGEGSTKGQ
IQLVQSGPELKKPGGSVKISCKASGYTFTSYSINWVRQAPGKGLEWVGWINTETREPAYAQGFTG
RFTFSADTSKSMAYLQINSLRAEDTAVYYCALDYLYSLDFWGQGTLVTVSSGGGGSQVQLVQSGA
EVKKPGASVKVSCKASGYTFTRYTMHWVRQAPGQGLEWIGYINPSKGYTNYNQKFKGRVTMTADK
STSTAYMELSSLRSEDTAVYYCARYYDDHYSLDYWGQGTLVTVSSGGGGSGGGGSGGGGSGGGGS
EIVMTQSPATLSVSPGERATLSCRASSSVSYLNWYQQKSGTSPKRWIYDTSKVASGVPYRFSGSG
SGTDFTLTISSLQAEDEATYYCQQWSSNPLTFGQGTKLEIK

SEQ ID NO: 23 (5'UTR for Inventive Construct; nt sequence)
AGACCCAAGCTGGCTAGCtctaaagaagcccctgggagcacagctcatcacc

SEQ ID NO: 24 (3'UTR for Inventive Construct; nt sequence)
ctatgaagaaggaaggcatccagaccagaaaccgaaaaatgtctagcaaatccaaaaagtgcaaa
aaagtgcatgactcactggaggacttccccaagaacagctcgtttaacccggccgccctctccag
acacatgtcctccctgagccacatctcgcccttcagccactccagccacatgctgaccacgccca
cgccgatgcacccgccatccagc
```

Where a polynucleotide sequence or "open reading frame" is described as, or by reference to, an amino acid sequence, the skilled person will understand that a corresponding polynucleotide sequence can be readily obtained that encodes the amino acid sequence. Generally, naturally occurring polynucleotide sequences (or fragments thereof) that encode a naturally occurring protein of interest (or fragment thereof) can be obtained from public sequence databases.

Exemplary Nucleotide Constructs

Provided herein are examples of RNA constructs useful to modify a cell to secrete one or more DNAse(s) in accordance with the invention:

Construct A:

| Cap | 5' UTR | NSP1-NSP4 | 26S promoter | DNASE1 | 3' UTR | polyA |
|---|---|---|---|---|---|---|

wherein "Cap" refers to a 5' cap, e.g., a 5-methylguanosine cap or other cap known in the art;

- "5' UTR" refers to a 5' untranslated region, e.g., the sequence of SEQ ID NO: 15;
- "NSP1-NSP4" refers to the nonstructural proteins of alphavirus NSP1, NSP2, NSP3, and NSP4, which can be exemplified as a combined unit, e.g., by the sequence of SEQ ID NO: 17;
- "26S promoter" is a transcriptional promoter exemplified by the sequence of SEQ ID NO: 18;
- DNASE1 encodes a DNASE1 protein, e.g., of the sequence of SEQ ID NO: 1 and in some embodiments preferably starts with a Kozak consensus sequence;
- "3' UTR" refers to a 3' untranslated region, e.g., the sequence of SEQ ID NO: 16; and "polyA" refers to a polyadenine tail, e.g., of 70 adenine units. The region denoted as "DNASE1" preferably includes a Kozak consensus sequence.

Construct B:

| Cap | 5' UTR | NSP1-NSP4 | 26S promoter | DNASE1L3 | 3' UTR | polyA |
|---|---|---|---|---|---|---|

wherein terms are as defined for Construct A, and wherein DNASE1L3 encodes a DNASE1L3 protein, e.g., of the sequence of SEQ ID NO: 2 and in some embodiments preferably starts with a Kozak consensus sequence.

Construct C:

| Cap | 5' UTR | NSP1-NSP4 | 26S promoter | DNASE1 | T2A | DNASE1L3 | 3' UTR | polyA |
|---|---|---|---|---|---|---|---|---|

wherein terms are as defined for Constructs A and B, and wherein "T2A" refers to a self-cleaving peptide, e.g., of the sequence of SEQ ID NO: 14.

Construct D:

| Cap | 5' UTR | NSP1-NSP4 | 26S promoter | DNASE1 | T2A | DNASE1L3 | 3' UTR | polyA |
|---|---|---|---|---|---|---|---|---|

wherein terms are as defined for Construct D.

Construct E:

| Cap | 5' UTR | NSP1-NSP4 | 26S promoter | DNASE1 | IRES | DNASE1L3 | 3' UTR | polyA |
|---|---|---|---|---|---|---|---|---|

wherein terms are as defined for Construct D, and wherein "IRES" refers to an Internal Ribosome Entry Site, e.g., of the sequence of SEQ ID NO: 13.

Construct F:

| Cap | 5' UTR | NSP1-NSP4 | 26S promoter | C protein | DNASE1 | T2A | DNASE1L3 | 3' UTR | polyA |
|---|---|---|---|---|---|---|---|---|---|

wherein terms are as defined for Construct D, and wherein "C protein" refers to a fragment of a viral C protein, e.g., of the sequence of SEQ ID NO: 19. Alternatively, the fragment of a viral C protein can consist of the first 34 or more amino acids recited in SEQ ID NO: 19.

Construct G:

| Cap | 5' UTR | NSP1-NSP4 | 26S promoter | C protein | DNASE1L3 | T2A | DNASE1 | 3' UTR | polyA |
|---|---|---|---|---|---|---|---|---|---|

wherein terms are as defined for Construct F.

Construct H:

| Cap | 5' UTR | NSP1-NSP4 | 26S promoter | C protein | DNASE1 | IRES | DNASE1L3 | 3' UTR | polyA |
|---|---|---|---|---|---|---|---|---|---|

wherein terms are as defined for Construct E and Construct F.

Construct I:

| Cap | 5' UTR | NSP1-NSP4 | 26S promoter | C protein | DNASE1L3 | T2A | DNASE1 | T2A | Bispec | 3' UTR | polyA |
|---|---|---|---|---|---|---|---|---|---|---|---|

wherein terms are as defined for Construct G, and wherein "Bispec" refers to a bispecific antibody, e.g., an anti-BCMA, anti-CD3 bispecific antibody, as further described below.

The above embodiments are particularly well suited for the modification of cells by introduction of self-amplifying RNA (saRNA).

Novel Cells Modified to Secrete One or More DNAse Enzymes

In one aspect, the invention provides a cell modified to secrete a DNase enzyme. In some embodiments, the cell is a mammalian cell. In some embodiments, the cell is a white blood cell, e.g., an NK cell, T cell, CD8+ cell, CD4+ cell, monocyte, macrophage, or CD34+ cell. In some embodiments, the cell is a Mesenchymal Stem (or Stromal) Cell (MSC). In some embodiments, the cell is a stem cell. In some embodiments, the cell is engineered to secrete DNAse.

In some embodiments, the DNAse is DNASE1. In some embodiments, the DNAse is DNASE1L1. In some embodiments, the DNAse is DNASE1L2. In some embodiments, the DNAse is DNASE1L3. In some embodiments, the DNAse is DNASE2A. In some embodiments, the DNAse is DNASE2B. In some embodiments, the DNAse is L-DNASEII. In some embodiments, the DNAse is CAD, also known as DFF40 or DFFB. In some embodiments, the DNAse is EndoG, also known as Endonuclease G.

In some embodiments, the cell is modified to secrete two or more DNase enzymes selected from the group consisting of: DNASE1, DNASE1L1, DNASE1L2, DNASE1L3, DNASE2A, DNAS2B, L-DNASEII, CAD, and EndoG. In some embodiments, the cell is modified to secrete: DNASE1 and DNASE1L1; DNASE1 and DNASE1L2; DNASE1 and DNASE1L3; DNASE1 and DNASE2A; DNASE1 and DNASE2B; DNASE1 and L-DNASEII; DNASE1 and CAD; DNASE1 and EndoG; DNASE1L1 and DNASE1L2; DNASE1L1 and DNASE1L3; DNASE1L1 and DNASE2A; DNASE1L1 and DNASE2B; DNASE1L1 and L-DNASEII; DNASE1L1 and CAD; DNASE1L1 and EndoG; DNASE1 and DNASE1L3; DNASE1 and DNASE2A; DNASE1 and DNASE2B; DNASE1 and L-DNASEII; DNASE1 and CAD; DNASE1 and EndoG; DNASE1L2 and DNASE1L3; DNASE1L2 and DNASE2A; DNASE1L2 and DNASE2B; DNASE1L2 and L-DNASEII; DNASE1L2 and CAD; DNASE1L2 and EndoG; DNASE1L3 and DNASE2A; DNASE1L3 and DNASE2B; DNASE1L3 and L-DNASEII; DNASE1L3 and CAD; DNASE1L3 and EndoG; DNASE2A and DNASE2B; DNASE2A and L-DNASEII; DNASE2A and CAD; DNASE2A and EndoG; DNASE2B and L-DNASEII; DNASE2B and CAD; DNASE2B and EndoG; L-DNASEII and CAD; L-DNASEII and EndoG; or CAD and EndoG.

In some embodiments, the cell is modified to express a DNAse comprising the sequence of SEQ ID NO: 1. In some embodiments, the cell is modified to secrete a protein having the sequence of SEQ ID NO: 1. In some embodiments, the cell is modified to express a DNAse comprising the sequence of SEQ ID NO: 2. In some embodiments, the cell is modified to secrete a protein having the sequence of SEQ ID NO: 2. In some embodiments, the cell is modified to express a protein comprising the sequence of SEQ ID NO: 3. In some embodiments, the cell is modified to secrete a protein having the sequence of SEQ ID NO: 3. In some embodiments, the cell is modified to express a first DNAse comprising the sequence of SEQ ID NO: 1 and a second DNAse comprising the sequence of SEQ ID NO: 2. In some embodiments, the cell is modified to secrete a first DNAse comprising the sequence of SEQ ID NO: 1 and a second DNAse comprising the sequence of SEQ ID NO: 2.

In some embodiments, the cell is modified to express a DNAse comprising a sequence having at least 90% sequence identity to the entire sequence of SEQ ID NO: 1. In some embodiments, the cell is modified to secrete a protein comprising a sequence having at least 90% sequence identity to the entire sequence of SEQ ID NO: 1. In some embodiments, the cell is modified to express a DNAse comprising a sequence having at least 90% sequence identity to the entire sequence of SEQ ID NO: 2. In some embodiments, the cell is modified to secrete a protein having at least 90% sequence identity to the entire sequence of SEQ ID NO: 2. In some embodiments, the cell is modified to express a protein comprising a sequence having at least 90% sequence identity to the entire sequence of SEQ ID NO: 3. In some embodiments, the cell is modified to secrete a protein comprising a sequence having at least 90% sequence identity to the entire sequence of SEQ ID NO: 3. In some embodiments, the cell is modified to express a first DNAse comprising a sequence having at least 90% sequence identity to the entire sequence of SEQ ID NO: 1 and a second DNAse comprising a sequence having at least 90% sequence identity to the entire sequence of SEQ ID NO: 2. In some embodiments, the cell is modified to secrete a first DNAse comprising a sequence having at least 90% sequence identity to the entire sequence of SEQ ID NO: 1 and a second DNAse comprising a sequence having at least 90% sequence identity to the entire sequence of SEQ ID NO: 2.

In some embodiments, the cell is modified to express a DNAse comprising a sequence having at least 80%, at least 85%, at least 90%, at least 95%, at least 96%, at least 97%, at least 98%, at least 99%, or at least 99.5% identical to the entire sequence of SEQ ID NO: 1. In some embodiments, the cell is modified to secrete a protein comprising a sequence having at least 80%, at least 85%, at least 90%, at least 95%, at least 96%, at least 97%, at least 98%, at least 99%, or at least 99.5% identical to the entire sequence of SEQ ID NO: 1. In some embodiments, the cell is modified to express a DNAse comprising a sequence having at least 80%, at least 85%, at least 90%, at least 95%, at least 96%, at least 97%, at least 98%, at least 99%, or at least 99.5% identical to the entire sequence of SEQ ID NO: 2. In some embodiments, the cell is modified to secrete a protein having at least 80%, at least 85%, at least 90%, at least 95%, at least 96%, at least 97%, at least 98%, at least 99%, or at least 99.5% identical to the entire sequence of SEQ ID NO: 2. In some embodiments, the cell is modified to express a protein comprising a sequence having at least 80%, at least 85%, at least 90%, at least 95%, at least 96%, at least 97%, at least 98%, at least 99%, or at least 99.5% identical to the entire sequence of SEQ ID NO: 3. In some embodiments, the cell is modified to secrete a protein comprising a sequence having at least 80%, at least 85%, at least 90%, at least 95%, at least 96%, at least 97%, at least 98%, at least 99%, or at least 99.5% identical to the entire sequence of SEQ ID NO: 3. In some embodiments, the cell is modified to express a first DNAse comprising a sequence having at least 80%, at least 85%, at least 90%, at least 95%, at least 96%, at least 97%, at least 98%, at least 99%, or at least 99.5% identical to the entire sequence of SEQ ID NO: 1 and a second DNAse comprising a sequence having at least 80%, at least 85%, at least 90%, at least 95%, at least 96%, at least 97%, at least 98%, at least 99%, or at least 99.5% identical to the entire sequence of SEQ ID NO: 2. In some embodiments, the cell is modified to secrete a first DNAse comprising a sequence having at least 80%, at least 85%, at least 90%, at least 95%, at least 96%, at least 97%, at least 98%, at least 99%, or at least 99.5% identical to the entire sequence of SEQ ID NO: 1 and a second DNAse comprising a sequence having at least 80%, at least 85%, at least 90%, at least 95%, at least 96%, at least 97%, at least 98%, at least 99%, or at least 99.5% identical to the entire sequence of SEQ ID NO: 2.

In some embodiments, the cell is modified by introduction of one of more polynucleotide constructs selected from the group consisting of Construct A, Construct B, Construct C, Construct D, Construct E, Construct F, Construct G, Construct H, and Construct I. In some embodiments, the cell is modified by introduction of a polynucleotide of Construct A. In some embodiments, the cell is modified by introduction of a polynucleotide of Construct B. In some embodiments, the cell is modified by introduction of a polynucleotide of Construct C. In some embodiments, the cell is modified by introduction of a polynucleotide of Construct D. In some embodiments, the cell is modified by introduction of a polynucleotide of Construct E. In some embodiments, the cell is modified by introduction of a polynucleotide of Construct F. In some embodiments, the cell is modified by introduction of a polynucleotide of Construct G. In some embodiments, the cell is modified by introduction of a polynucleotide of Construct H. In some embodiments, the cell is modified by introduction of a polynucleotide of Construct I.

In some of the foregoing embodiments, the cell is modified to secrete one or more DNase enzymes that the cell does not normally express, or does not normally secrete. In some of the foregoing embodiments, the cell is modified to overexpress one or more DNase enzymes. In some of the foregoing embodiments, the cell is modified to secrete one or more DNase enzymes that it normally expresses but does not normally secrete.

In some embodiments, the modified cells of the invention are modified through the introduction of DNA into the cells; in some such embodiments, the DNA that comprises a sequence that is complementary to one or more RNA sequences described herein, or a portion thereof. In some embodiments, the modified cells of the invention are modified through the introduction of RNA into the cells (e.g., an RNA comprising a sequence that encodes one or more DNAse enzymes, e.g., DNASE1 and/or DNASE1L3, as described herein). In some embodiments, the RNA is a messenger RNA (mRNA). In some embodiments, the RNA is a self-amplifying RNA (saRNA). In some embodiments, the RNA comprises pseudouridine. In some embodiments, the mRNA is artificially enriched in pseudouridine. In some embodiments, substantially all of the uridine nucleotides of the RNA are substituted with pseudouridine. Methods for incorporating pseudouridine into an RNA are generally known in the art.

In some embodiments, two or more mRNA molecules encoding different proteins are used to modify the cells. In some embodiments, two or more saRNA molecules encoding different proteins are used to modify the cells. In some embodiments, two or more protein products are encoded on the same RNA molecule used to modify the cells. In some embodiments, two or more protein products are encoded on the same mRNA molecule used to modify the cells. In some embodiments, two or more protein products are encoded on the same saRNA molecule used to modify the cells. In some embodiments, two or more DNAse enzymes, e.g., DNASE1 and DNASE1L3, are encoded on the same RNA molecule used to modify the cells. In some embodiments, two or more DNAse enzymes, e.g., DNASE1 and DNASE1L3, are encoded on the same mRNA molecule used to modify the cells. In some embodiments, two or more DNAse enzymes, e.g., DNASE1 and DNASE1L3, are encoded on the same saRNA molecule used to modify the cells.

In some embodiments, two separate mRNA molecules encoding DNASE1 and DNASE1L3, respectively, are introduced into cell(s) to cause the cell(s) to express and/or secrete each of DNASE1 and DNASE1L3. In some embodiments, both of the mRNA molecules are artificially enriched in pseudouridine. In some embodiments, substantially all of the uridine nucleotides of the mRNA molecules are substituted with pseudouridine. In some embodiments, the cell is modified by introduction of a DNASE1-encoding mRNA that is enriched in pseudouridine and a DNASE1L3-encoding mRNA that is not enriched in pseudouridine. In some embodiments, the cell is modified by introduction of a DNASE1-encoding mRNA that is not enriched in pseudouridine and a DNASE1L3-encoding mRNA that is enriched in pseudouridine. In some embodiments, the cell is modified by introduction of a DNASE1-encoding mRNA wherein substantially all of the uridine nucleotides are substituted with pseudouridine and a DNASE1L3-encoding mRNA that is not enriched in pseudouridine.

In some embodiments, a cell is modified by introduction of a DNASE1-encoding mRNA that is not enriched in pseudouridine and a DNASE1L3-encoding mRNA wherein substantially all of the uridine nucleotides are substituted with pseudouridine.

In some embodiments wherein a cell is modified to express DNAse enzyme(s) encoded by an saRNA, the same cell is also modified to express an RNA-dependent RNA polymerase (RDRP), whereby the cell amplifies, i.e., replicates, the saRNA(s) introduced into it. In some embodiments, the saRNA molecule encoding the RDRP protein is separate from the saRNA molecule encoding one or more DNAse proteins.

In some embodiments, an in vitro transcribed RNA can be introduced to a cell as a form of transfection. The RNA is produced by in vitro transcription using a polymerase chain reaction (PCR)-generated template. In some embodiments, the RNA is transcribed directly from a linearized plasmid. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence, or any other appropriate source of DNA. The desired template for in vitro transcription is the DNAse of the present invention.

Nucleic acid, including but not limited to RNA, can be introduced into target cells using any of a number of different methods, for instance, commercially available methods which include, but are not limited to, electroporation (4D NUCLEOFECTOR® or AMAXA NUCLEOFECTOR-II® (Lonza, Basel, Switzerland), MaxCyte apparatuses (MaxCyte, Gaithersburg, MD), ECM 830 BTX (Harvard Instruments, Boston, Mass.), GENE PULSER II® (BioRad, Denver, Colo.), or MULTIPORATOR® (Eppendorf, Hamburg Germany)), flow electroporation (e.g., U.S. Pat. Pub. No. 2017/0218355) mechanical membrane disruption (e.g., cell squeezing, see U.S. Pat. Pub. No. 2014/287509A1), cationic liposome mediated transfection using lipofection, nanoparticle-mediated delivery (e.g., with lipid encapsulated nanoparticles, gold, or polymer encapsulated nanoparticles), polymer encapsulation, peptide mediated transfection, or biolistic particle delivery systems, such as "gene guns" (see, e.g., Nishikawa, et al. Hum Gene Ther., 12(8):861-70 (2001).

In some embodiments, the DNAse sequence(s) (e.g., nucleic acid sequence(s) encoding a DNAse, e.g., DNASE1 and/or DNASE1L3, as described herein) are delivered into cells (e.g., NK cells, T cells, monocytes, macrophages, MSCs, or stem cells) using a retroviral or lentiviral vector. DNAse-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In some embodiments, one or more DNAses (e.g., DNASE1 and/or DNASE1L3) can be expressed in the cells (e.g., NK cells, T cells, monocytes, macrophages, MSCs, or stem cells) by way of transposons and/or retrotransposons, e.g., piggyBac™ transposon system (System Biosiences, Palo Alto, CA), and sleeping beauty transposon system (see, e.g., Geurts et al., *Mol. Ther.* 2003; 8:108-117).

In some embodiments, the cell that is modified to express and/or secrete one or more DNAses ((e.g., DNASE1 and/or DNASE1L3) is further modified to express and/or secrete one or more survival factors, e.g., transmembrane IL-15 (e.g., SEQ ID NO:4), secreted IL-15, IL15-TGFβ fusion protein (e.g., SEQ ID NO:6), and/or IL-15 TGFβ fusion protein (e.g., SEQ ID NO: 7).

In some embodiments, the cell that is modified to express and/or secrete one or more DNAses ((e.g., DNASE1 and/or DNASE1L3) is further modified to express one or more translation enhancers, e.g., influenza NS1 (e.g., SEQ ID NO: 7), Vaccinia E3 (e.g., SEQ ID NO: 8), human XBP1-iso2 (e.g., SEQ ID NO: 9), DP71L (e.g., SEQ ID NO: 10), PP1-GADD34 eIF2a binding protein (e.g., SEQ ID NO: 11), and/or B18R (e.g., SEQ ID NO: 12).

In any of the above embodiments wherein a nucleic acid or nucleic acid construct is introduced into a cell, that nucleic acid or nucleic acid construct can be an exogenous nucleic acid or exogenous nucleic acid construct. Generally, the exogenous nucleic acid or nucleic acid construct can be any nucleic acid or nucleic acid construct disclosed herein. In some embodiments, an exogenous RNA or RNA construct is introduced into a cell to modify the cell. In some embodiments, an exogenous DNA or DNA construct is introduced into a cell to modify the cell.

Sources of Homospecific Cells

Prior to modification of the cells of the invention, including homospecific cells, for example NK cells, T cells, monocytes, macrophages, MSCs, stem cells, a source of cells is obtained from a subject of the same species. In some embodiments, the cells are derived from a subject different than the intended recipient of the modified cells (i.e., heterologous use, including clinical heterologous use). In some other embodiments, the cells are derived from the same subject for whom they are intended once modified (i.e., autologous use). Homospecific cells can be obtained from a number of sources, including peripheral blood mononuclear cells, bone marrow, adipose tissue, lymph node tissue, cord blood, thymus tissue, tissue from a site of infection, ascites, pleural effusion, spleen tissue, blood, and tumors. Homospecific cells, including stem cells, may be generated from induced pluripotent stem cells or hematopoietic stem cells or progenitor cells. In some embodiments of the present invention, any number of cell lines, including but not limited to NK cell lines, T cell lines, and/or stem cell lines, available in the art, may be used. In some embodiments of the present invention, homospecific blood cells (e.g., NK cells, T cells, monocytes, macrophages, MSCs, stem cells) can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, NK cells, other nucleated white blood cells including CD34+ cells, red blood cells, and platelets. In some embodiments, the cells collected by apheresis may be washed to remove the plasma fraction and to place the cells in an appropriate buffer or media for subsequent processing steps. In some embodiments of the invention, the cells are washed with phosphate buffered saline (PBS) or other suitable fluid. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, blood cells, including homospecific blood cells, for example, NK cells, T cells, monocytes, macrophages, or CD34+ cells are isolated from peripheral blood lymphocytes by lysing the red blood cells and depleting the monocytes, for example, by centrifugation through a PERCOLL™ gradient or by counterflow centrifugal elutriation. A specific subpopulation of cells, such as NK cells, T cells, or CD34+ cells, can be further isolated by positive or negative selection techniques.

In some embodiments, MSCs are isolated from: bone marrow mononuclear cells, which can be obtained, for example, by bone marrow aspiration; umbilical cord tissue; adipose tissue; and/or a tooth or teeth.

Therapeutic Application

The modified, DNAse-expressing cells of the present invention, including homospecific cells, may be administered either alone, or as a composition (e.g., a pharmaceutical composition) in combination with diluents and/or with other components such as cytokines, immunomodulators, other cell populations, or other small molecules or biologics. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins such as albumin; polypeptides or amino acids such as glycine; antioxidants; chelating agents such as EDTA or glutathione; adjuvants (e.g., aluminum hydroxide); and preservatives.

Compositions of the present invention are preferably formulated for intravenous administration.

In some embodiments, the homospecific cells may be modified in vivo by administering nucleic acid directly to the patient. In some embodiments, the nucleic acid may be administered by, for example, intraveneous, subcutaneous, intradermal, or intramuscular injection. In some embodiments, the nucleic acid may be combined with a suitable carrier. In some embodiments, the carrier may be a nanoparticle carrier, for example a polymeric nanoparticle, lipid-based nanoparticle, or metal nanoparticle such as gold. In some embodiments, the carrier may be a viral vector, for example a lentiviral or adenoviral vector.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The administration of the inventive compositions may be carried out in any convenient manner, including by aerosol inhalation, injection, ingestion, transfusion, implantation or transplantation. The compositions described herein may be administered to a patient subcutaneously, intradermally, intraarticularly, intratumorally, intranodally, intramedullary, intramuscularly, by intravenous injection, or intraperitoneally. In some embodiments, the inventive cell compositions of the present invention are administered to a patient by intradermal or subcutaneous injection. In another embodiment, the inventive cell compositions of the present invention are preferably administered by intravenous injection.

The inventive cells and/or compositions derived thereof can be administered to a subject for therapeutic use. Thus, the invention provides a method for treating or preventing a disease in a subject in need thereof, the method comprising administering to the subject an effective number of the inventive cells. In some embodiments, the effective number (or amount) is determined as the number of cells. In some embodiments, the effective number (or amount) is determined by the amount of DNAse secreted by those cells. In some embodiments, the effective number is more than 1×10^8 cells. In some embodiments, the effective number is more than 5×10^8 cells. In some embodiments, the effective number is more than 1×10^9 cells. In some embodiments, the effective number is more than 2×10^9 cells. In some embodiments, the effective number is more than 5×10^9 cells. In some embodiments, the effective number is more than 10×10^9 cells.

Likewise, the invention provides for use of the inventive cells for the treatment or prevention of a disease.

In the above methods of treatment, or in the above uses, disease in need of treatment or prevention can include, for example: acute respiratory distress syndrome (ARDS), acute kidney injury (AKI), sepsis, myocardial infarction, systemic lupus erythematosus (SLE), rheumatoid arthritis (RA), systemic sclerosis (SS), asthma, and cancer. Some specific forms of ARDS suitable for the above methods of treatment and uses include ARDS caused, for example, by a bacterial infection such as by *Streptococcus pneumoniae* or *Haemophilus influenzae*, viral infections such as influenza virus A-D or SARS-CoV-2, aspiration due to emesis or water (e.g., near-drowning episodes), and inhalation of harmful substances such as smoke or chemical fumes.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXEMPLARY EMBODIMENTS

Some embodiments of the invention are:

Embodiment 1. A mammalian cell modified to secrete a DNAse enzyme.

Embodiment 2. The cell of Embodiment 1, wherein the mammalian cell is a human cell.

Embodiment 3. The cell of any one of Embodiments 1-2, wherein the mammalian cell is a white blood cell.

Embodiment 4. The cell of Embodiment 3, wherein the white blood cell is an NK cell.

Embodiment 5. The cell of Embodiment 3, wherein the white blood cell is a T cell.

Embodiment 6. The cell of Embodiment 5, wherein the white blood cell is a CD8+ cell.

Embodiment 7. The cell of Embodiment 5, wherein the white blood cell is a CD4+ cell.

Embodiment 8. The cell of Embodiment 3, wherein the white blood cell is a monocyte.

Embodiment 9. The cell of Embodiment 3, wherein the white blood cell is a macrophage.

Embodiment 10. The cell of Embodiment 3, wherein the white blood cell is a CD34+ cell.

Embodiment 11. The cell of any one of Embodiments 1-2, wherein the mammalian cell is a mesenchymal stem cell.

Embodiment 12. The cell of any one of Embodiments 1-2, wherein the mammalian cell is a stem cell.

Embodiment 13. The cell of any one of Embodiments 1-12, wherein the DNAse is DNASE1.

Embodiment 14. The cell of any one of Embodiments 1-12, wherein the DNAse is DNASE1L1.

Embodiment 15. The cell of any one of Embodiments 1-12, wherein the DNAse is DNASE1L2.

Embodiment 16. The cell of any one of Embodiments 1-12, wherein the DNAse is DNASE1L3.

Embodiment 17. The cell of any one of Embodiments 1-12, wherein the DNAse is DNASE2A.

Embodiment 18. The cell of any one of Embodiments 1-12, wherein the DNAse is DNASE2B.

Embodiment 19. The cell of any one of Embodiments 1-12, wherein the DNAse is L-DNASEII.

Embodiment 20. The cell of any one of Embodiments 1-12, wherein the DNAse is CAD.

Embodiment 21. The cell of any one of Embodiments 1-13, wherein the cell secretes two or more DNAse enzymes selected from the group consisting of: DNASE1, DNASE1L1, DNASE1L2, DNASE1L3, DNASE2A, DNAS2B, L-DNASEII, CAD, and EndoG.

Embodiment 22. The cell of any one of Embodiments 1-21, wherein the cell is modified by electroporation.

Embodiment 23. The cell of any one of Embodiments 1-21, wherein the cell is modified by cell squeezing.

Embodiment 24. The cell of any one of Embodiments 1-21, wherein the cell is modified by use of a viral vector.

Embodiment 25. The cell of any one of Embodiments 1-24, wherein the cell is modified by introduction of an RNA encoding the DNASE enzyme(s).

Embodiment 26. The cell of any one of Embodiments 1-25, wherein the RNA is artificially enriched in pseudouridine.

Embodiment 27. The cell of any one of Embodiments 1-25, wherein substantially all of the uridine nucleotides in the RNA are substituted with pseudouridine.

Embodiment 28. The cell of any one of Embodiments 1-27, wherein the cell is modified by introduction of an mRNA encoding the DNASE enzyme(s).

Embodiment 29. The cell of any one of Embodiments 1-27, wherein the cell is modified by introduction of a self-amplifying RNA encoding the DNASE enzyme(s).

Embodiment 30. The cell of any one of Embodiments 1-21, wherein the cell is modified by introduction of a nucleic acid encoding a protein of the sequence of SEQ ID NO: 1.

Embodiment 31. The cell of any one of Embodiments 1-21, wherein the cell is modified by introduction of a nucleic acid encoding a protein of the sequence of SEQ ID NO: 2.

Embodiment 32. A cell of any one of Embodiments 1-21, wherein the cell is modified by introduction of a nucleic acid encoding a protein of the sequence of SEQ ID NO: 3.

Embodiment 33. The cell of any one of Embodiments 1-24, wherein the cell is modified by introduction of a DNA encoding the DNASE enzyme(s).

Embodiment 34. The cell of any one of Embodiments 1-33, wherein the cell is modified by means of a nanoparticle, wherein the nanoparticle comprises a nucleic acid that encodes the DNASE enzyme(s).

Embodiment 35. The cell of any one of Embodiments 1-34, wherein the cell is further modified to express an anti-BCMA protein.

Embodiment 36. The cell of Embodiment 35, wherein anti-BCMA protein comprises a monoclonal antibody that binds BCMA.

Embodiment 37. The cell of Embodiment 35, wherein anti-BCMA protein comprises a bispecific antibody that binds BCMA and CD3.

Embodiment 38. The cell of Embodiment 35, wherein anti-BCMA protein comprises a bispecific antibody that binds BCMA and CD8.

Embodiment 39. The cell of Embodiment 35, wherein anti-BCMA protein comprises a bispecific antibody that binds BCMA and CD4.

Embodiment 40. A cell therapy product comprising a plurality of cells of any one of Embodiments 1-39.

Embodiment 41. A cell therapy product comprising: at least one cell of Embodiment 13 and at least one cell of Embodiment 16.

Embodiment 42. A cell therapy product comprising at least one cell selected of Embodiment 16 and at least one cell selected from the group consisting of Embodiments 13, 14, 15, 17, 18, 19 and 20.

Embodiment 43. The cell therapy product of any one of Embodiments 40-42, wherein the number of cells per dose is at least 1×10ˆ8.

Embodiment 44. The cell therapy product of Embodiment 43, wherein the number of cells per dose is at least 5×10ˆ8.

Embodiment 45. The cell therapy product of Embodiment 43, wherein the number of cells per dose is at least 1×10ˆ9.

Embodiment 46. The cell therapy product of Embodiment 43, wherein the number of cells per dose is at least 5×10ˆ9.

Embodiment 47. The cell therapy product of Embodiment 43, wherein the number of cells per dose is at least 1×10ˆ10.

Embodiment 48. A method of treating a subject in need thereof, comprising administering to the subject a cell of any one of Embodiments 1-39.

Embodiment 49. A method of treating a subject in need thereof, comprising administering to the subject a cell therapy product of any one of Embodiments 40-47.

Embodiment 50. The method of any one of Embodiments 48-49, wherein the subject suffers from Acute Respiratory Distress Syndrome.

Embodiment 51. The method of any one of Embodiments 48-49, wherein the subject suffers from a viral infection.

Embodiment 52. The method of any one of Embodiments 48-49, wherein the subject suffers from COVID-19.

Embodiment 53. The method of any one of Embodiments 48-49, wherein the subject suffers from acute kidney injury.

Embodiment 54. The method of any one of Embodiments 48-49, wherein the subject suffers from sepsis.

Embodiment 55. The method of any one of Embodiments 48-49, wherein the subject suffers from myocardial infarction.

Embodiment 56. The method of any one of Embodiments 48-49, wherein the subject suffers from acute ischemia.

Embodiment 57. The method of any one of Embodiments 48-49, wherein the subject suffers from systemic lupus erythematosus.

Embodiment 58. The method of any one of Embodiments 48-49, wherein the subject suffers from rheumatoid arthritis.

Embodiment 59. The method of any one of Embodiments 48-49, wherein the subject suffers from inflammatory bowel disease.

Embodiment 60. The method of any one of Embodiments 48-49, wherein the subject suffers from cancer.

Embodiment 61. Use of a cell of any one of Embodiments 1-39 for treatment of disease.

Embodiment 62. Use of a cell therapy product of any one of Embodiments 40-47 for treatment of disease.

Embodiment 63. The use of any one of Embodiments 61-62, wherein the disease is Acute Respiratory Distress Syndrome.

Embodiment 64. The use of any one of Embodiments 61-62, wherein the disease is a viral infection.

Embodiment 65. The use of any one of Embodiments 61-62, wherein the disease is COVID-19.

Embodiment 66. The use of any one of Embodiments 61-62, wherein the disease is acute kidney injury.

Embodiment 67. The use of any one of Embodiments 61-62, wherein the disease is sepsis.

Embodiment 68. The use of any one of Embodiments 61-62, wherein the disease is myocardial infarction.

Embodiment 69. The use of any one of Embodiments 61-62, wherein the disease is acute ischemia.

Embodiment 70. The use of any one of Embodiments 61-62, wherein the disease is systemic lupus erythematosus.

Embodiment 71. The use of any one of Embodiments 61-62, wherein the disease is rheumatoid arthritis.

Embodiment 72. The use of any one of Embodiments 61-62, wherein the disease is inflammatory bowel disease.

Embodiment 73. The use of any one of Embodiments 61-62, wherein the disease is cancer.

Embodiment 74. A nanoparticle comprising a nucleic acid encoding a DNAse, wherein the nanoparticle is adapted for combination with a mammalian cell, and whereby the combination results in secretion by the mammalian cell of the DNAse.

Embodiment 75. The nanoparticle of Embodiment 74, wherein the DNAse is DNASE1.

Embodiment 76. The nanoparticle of Embodiment 74, wherein the DNAse is DNASE1L3.

Embodiment 77. The nanoparticle of Embodiment 74, wherein the combination results in secretion by the mammalian cell of DNASE1 and DNASE1L3.

Embodiment 78. The nanoparticle of any one of Embodiments 74-77, wherein the nucleic acid is DNA.

Embodiment 79. The nanoparticle of any one of Embodiments 74-77, wherein the nucleic acid is RNA.

Embodiment 80. The nanoparticle of Embodiment 79, wherein the RNA is mRNA.

Embodiment 81. The nanoparticle of Embodiment 79, wherein the RNA is saRNA.

Embodiment 82. The nanoparticle of any one of Embodiments 74-81, wherein the combination occurs in vitro.

Embodiment 83. The nanoparticle of any one of Embodiments 74-81, wherein the combination occurs in vivo.

Embodiment 84. The nanoparticle of Embodiment 74, further comprising a nucleic acid comprising an anti-BCMA protein, whereby the combination further results in secretion by the cell of the anti-BCMA protein.

Embodiment 85. A polynucleotide comprising the structure of Construct A.

Embodiment 86. A polynucleotide comprising the structure of Construct B.

Embodiment 87. A polynucleotide comprising the structure of Construct C.

Embodiment 88. A polynucleotide comprising the structure of Construct D.

Embodiment 89. A polynucleotide comprising the structure of Construct E.

Embodiment 90. A polynucleotide comprising the structure of Construct F.

Embodiment 91. A polynucleotide comprising the structure of Construct G.

Embodiment 92. A polynucleotide comprising the structure of Construct H.

Embodiment 93. A polynucleotide comprising the structure of Construct I.

Embodiment 94. The polynucleotide of any one of Embodiments 85-93, wherein the polynucleotide is artificially enriched in pseudouridine.

Embodiment 95. The polynucleotide of any one of Embodiments 85-93, wherein substantially all of the uridine nucleotides in the RNA are substituted with pseudouridine.

Embodiment 96. A mammalian cell comprising a polynucleotide comprising a structure selected from the group consisting of: Construct A, Construct B, Construct C, Construct D, Construct E, Construct F, Construct G, Construct H, and Construct I.

Embodiment 97. The cell of Embodiment 96, wherein the polynucleotide is an RNA that is artificially enriched in pseudouridine.

Embodiment 98. The polynucleotide of Embodiment 96, wherein the polynucleotide is an RNA wherein substantially all of the uridine nucleotides in the RNA are substituted with pseudouridine.

Embodiment 99. A mammalian cell comprising a polynucleotide having the structure of Construct A.

Embodiment 100. A mammalian cell comprising a polynucleotide having the structure of Construct B.

Embodiment 101. A mammalian cell comprising a polynucleotide having the structure of Construct C.

Embodiment 102. A mammalian cell comprising a polynucleotide having the structure of Construct D.

Embodiment 103. A mammalian cell comprising a polynucleotide having the structure of Construct E.

Embodiment 104. A mammalian cell comprising a polynucleotide having the structure of Construct F.

Embodiment 105. A mammalian cell comprising a polynucleotide having the structure of Construct G.

Embodiment 106. A mammalian cell comprising a polynucleotide having the structure of Construct H.

Embodiment 107. A mammalian cell comprising a polynucleotide having the structure of Construct I.

Embodiment 108. The cell of any one of Embodiments 99-107, wherein the cell is an NK cell.

Embodiment 109. The cell of any one of Embodiments 99-107, wherein the cell is an MSC.

Embodiment 110. The cell of any one of Embodiments 99-107, wherein the cell is a T cell.

Embodiment 111. The cell of any one of Embodiments 99-107, wherein the cell is a monocyte.

Embodiment 112. The cell of any one of Embodiments 99-107, wherein the cell is a macrophage.

Embodiment 113. The cell of any one of Embodiments 99-107, wherein the cell is a stem cell.

Embodiment 114. The cell of any one of Embodiments 99-113, wherein the polynucleotide is an RNA that is artificially enriched in pseudouridine.

Embodiment 115. The cell of any one of Embodiments 99-113, wherein the polynucleotide is an RNA wherein substantially all of the uridine nucleotides in the RNA are substituted with pseudouridine.

Embodiment 116. A mammalian cell comprising a first exogenous RNA encoding DNASE1 and a second exogenous RNA encoding DNASE1L3, wherein the second exogenous RNA is artificially enriched in pseudouridine.

Embodiment 117. A mammalian cell comprising a first exogenously introduced RNA encoding DNASE1 and a second exogenously introduced RNA encoding DNASE1L3, wherein substantially all of the uridine nucleotides in the second exogenously introduced RNA are substituted with pseudouridine.

Embodiment 118. The cell of any one of Embodiments 116-117, wherein the RNA encoding DNASE1 is not artificially enriched in pseudouridine.

Embodiment 119. A mammalian mesenchymal stem cell comprising an exogenous RNA encoding DNASE1.

Embodiment 120. A mammalian mesenchymal stem cell comprising an exogenous RNA encoding DNASE1L3.

Embodiment 121. A mammalian mesenchymal stem cell comprising an exogenous RNA encoding DNASE1 and DNASE1L3.

Embodiment 122. A mammalian mesenchymal stem cell comprising a first exogenous RNA encoding DNASE1 and a second exogenous DNASE1L3.

Embodiment 123. The cell of Embodiment 122, wherein the second exogenous RNA is artificially enriched in pseudouridine.

Embodiment 124. The cell of Embodiment 122, wherein substantially all of the uridine nucleotides in the second exogenously introduced RNA are substituted with pseudouridine.

Embodiment 125. The cell of any one of Embodiments 122-124, wherein the first RNA is not artificially enriched in pseudouridine.

Embodiment 126. The cell of any one of Embodiments 99-125, wherein the cell is a human cell.

Embodiment 127. A method for treating or preventing disease, the method comprising administering to a subject in need thereof a cell of any one of Embodiments 99-125.

Embodiment 128. Use of a cell of any one of Embodiments 99-125 for the treatment or prevention of a disease.

Embodiment 129. The method of any one of Embodiments 127-128, wherein the disease is Acute Respiratory Distress Syndrome.

Embodiment 130. The method of any one of Embodiments 127-128, wherein the disease is a viral infection.

Embodiment 131. The method of any one of Embodiments 127-128, wherein the disease is COVID-19.

Embodiment 132. The method of any one of Embodiments 127-128, wherein the disease is acute kidney injury.

Embodiment 133. The method of any one of Embodiments 127-128, wherein the disease is sepsis.

Embodiment 134. The method of any one of Embodiments 127-128, wherein the disease is myocardial infarction.

Embodiment 135. The method of any one of Embodiments 127-128, wherein the disease is acute ischemia.

Embodiment 136. The method of any one of Embodiments 127-128, wherein the disease is systemic lupus erythematosus.

Embodiment 137. The method of any one of Embodiments 127-128, wherein the disease is rheumatoid arthritis.

Embodiment 138. The method of any one of Embodiments 127-128, wherein the disease is inflammatory bowel disease.

Embodiment 139. The method of any one of Embodiments 127-128, wherein the disease is cancer.

EXAMPLES

Without further elaboration, it is believed that one of ordinary skill in the art can, based on the above description, utilize the present disclosure to its fullest extent. Nevertheless, in order that the invention described herein may be more fully understood, the following examples are set forth. The synthetic examples described in this application are offered to illustrate the compounds and methods provided herein and are not to be construed in any way as limiting their scope. All publications cited herein are incorporated by reference for the purposes or subject referenced herein.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein are meant to be non-limiting. In describing and claiming the present invention, the following terminology will be used.

Example 1: Production of Functional DNAse-Secreting NK Cells from an Inventive saRNA Construct The following example is of human DNAse-secreting NK cells produced by introduction of an inventive saRNA construct that encodes human DNASE1 and DNASE1L3.

An inventive saRNA construct comprising the nucleotide sequence of SEQ ID NO: 3 is generated by in vitro transcription from a DNA plasmid. The in vitro transcription is performed by SP6 RNA polymerase from a linearized plasmid template (alternatively, a T7 polymerase can be used). A polyadenine tail of about 150 adenine nucleotides can be added enzymatically to the saRNA. A 7-methylguanosine cap can be incorporated at the 5' end of the saRNA during the co-transcriptional RNA synthesis.

This inventive saRNA construct comprises, from 5' to 3': a 5' cap, a 5' UTR described as SEQ ID NO: 15, an RNA-dependent RNA polymerase (RDRP) sequence described as SEQ ID NO: 17 (i.e., NSP1-NSP4), a DNASE1 open reading frame (ORF) described as SEQ ID NO: 1, a T2A sequence described in SEQ ID NO: 14, a DNASE1L3 ORF described as SEQ ID NO: 2, an T2A sequence described in SEQ ID NO: 14, a translation enhancer ORF described as SEQ ID NO: 8, a T2A sequence described in SEQ ID NO: 14, a human IL-15 ORF described as SEQ ID NO: 4, a 3' UTR described as SEQ ID NO: 16, and a 3' polyadenine tail of 150 adenine units or more.

A translation enhancer mRNA construct encoding a protein comprising the sequence of SEQ ID NO: 8 is generated by in vitro transcription from a DNA plasmid. The in vitro transcription can be performed by T7 RNA polymerase from a linearized plasmid template. A polyadenine tail of about 150 adenine nucleotides is added enzymatically to the mRNA. A 7-methylguanosine cap is incorporated at the 5' end of the mRNA during the co-transcriptional RNA synthesis. The translation enhancer mRNA construct comprises, from 5' to 3': a 5' cap, a 5' UTR described as SEQ ID NO: 23, a Kozak sequence described in SEQ ID NO: 20, an open reading frame (ORF) of sequence of SEQ ID NO: 8, a 3' UTR described as SEQ ID NO: 24, and a 3' polyadenine tail of 150 adenine units or more.

To prepare NK cells with the RNA constructs, NK cells are isolated from umbilical cord blood by CD3+ magnetic bead negative selection followed by CD56+ magnetic bead positive selection to obtain >98% pure NK cells that are >95% viable. These NK cells are expanded by incubation at 37° C. with 5% $CO_2$ in the presence of K562 feeder cells engineered to express membrane-bound IL-15 for about 14 days. The cells are resuspended in transfection buffer and transfected with a mixture of the saRNA construct and mRNA construct by electroporation (4D NUCLEOFECTOR®, Lonza) according to manufacturer's instructions. The cells are then returned to culture in a standard medium containing IL-15 for overnight incubation, then frozen at −80 C. Transfected cells are thawed and incubated for another 7 days in the presence of complete medium containing IL-15 and supernatant samples are collected and frozen at 4 h, 1 day, 2 days, 3 days, 5 days and 7 days after thaw. Thawed cells and supernatants are assayed for viability and activity according to the methods described below.

NK cells obtained from the above-described process can be tested for viability, DNASE1 and DNASE1L3 expression, and DNA- and chromatin-degrading capacity. Viability can be determined by flow cytometry on a GUAVA® EASYCYTE® 12HT Flow cytometer (EMD Millipore). To test viability, a sample of the NK cells is mixed with propidium iodide and run on the flow cytometer with electronic gating on fluorescence in the near infrared channel. To test expression of DNASE1 and DNASE1L3, commercially available DNASE1 and DNASE1L3 kits (i.e., Abbexa) are used to assay supernatants of cultured NK cells according to the manufacturers' instructions. To test DNA degrading capacity of transfected NK cells, culture supernatants are tested with a fluorometric DNASE1 assay kit (i.e., AbCam) according to the manufacturer's instructions. To test chromatin degrading capacity of transfected NK cells, culture supernatants are first incubated with NETs generated from phorbol myristate acetate-activated human neutrophils. Neutrophils are isolated from fresh apheresis product by density grade centrifugation. Recombinant human DNASE1 and DNASE1L3 are used as positive controls. The amount of NET DNA released is determined by adding picogreen (Invitrogen), a DNA fluorescence dye, to the mixed culture and then quantified by fluorescence spectrometry.

It is expected that DNASE1- and DNASE1L3-transfected NK cells will express and secrete functional DNASE1 and DNASE1L3 constitutively over the course of at least 24 hours. It is further expected that NK cells will maintain the capacity to express and secrete functional DNASE1 and DNASE1L3 following freeze/thaw.

Thus, NK cells can be transfected with the inventive saRNA sequence to express and secrete functional DNASE1 and DNASE1L3 protein. The result of this process is inventive, i.e., DNase-secreting NK cells that are useful for therapeutic administration, e.g., to a person affected by ARDS.

Example 2: Production of Functional DNAse-Secreting MSCs from an saRNA Construct The following example is of human DNAse-secreting MSCs produced by introduction of an inventive saRNA construct that encodes human DNASE1 and DNASE1L3.

An inventive saRNA construct comprising the nucleotide sequence of SEQ ID NO: 3 is generated by in vitro transcription from a DNA plasmid. The in vitro transcription is performed by SP6 RNA polymerase from a linearized plasmid template (alternatively, a T7 polymerase can be used). A polyadenine tail of about 150 adenine nucleotides is added enzymatically to the saRNA. A 7-methylguanosine cap is incorporated at the 5' end of the saRNA during the co-transcriptional RNA synthesis.

The inventive saRNA construct comprise, from 5' to 3': a 5' cap, a 5' UTR described as SEQ ID NO: 15, an RNA-dependent RNA polymerase (RDRP) sequence described as SEQ ID NO: 17, DNASE1 open reading frame (ORF) described as SEQ ID NO: 1, a T2A sequence described in SEQ ID NO: 14, a DNASE1L3 ORF described as SEQ ID NO: 2, a T2A sequence described in SEQ ID NO: 14, a translation enhancer ORF described as SEQ ID NO: 8, a 3' UTR described as SEQ ID NO: 16, and a 3' polyadenine tail of 150 adenine units or more.

A translation enhancer mRNA construct encoding a protein comprising the sequence of SEQ ID NO: 8 is generated by in vitro transcription from a DNA plasmid. The in vitro transcription is performed by T7 RNA polymerase from a linearized plasmid template. A polyadenine tail of about 150 adenine nucleotides is added enzymatically to the mRNA. A 7-methylguanosine cap is incorporated at the 5' end of the mRNA during the co-transcriptional RNA synthesis. The translation enhancer mRNA construct comprises, from 5' to 3': a 5' cap, a 5' UTR described as SEQ ID NO: 15, a Kozak sequence described in SEQ ID NO: 20, the translation enhancer open reading frame (ORF) comprising the nucleotide sequence of SEQ ID NO: 8, a 3' UTR described as SEQ ID NO: 16, and a 3' polyadenine tail of 150 adenine units or more.

To prepare MSCs from RNA constructs, MSCs isolated from human umbilical cord are purchased from ATCC, thawed and expanded in T75 flasks by culture at 37° C. with 5% $CO_2$ in α-DMEM medium supplemented with 10% human serum. Cells are passaged upon reaching 80% confluency. The cells are resuspended in transfection buffer and transfected with a mixture of the saRNA construct and mRNA construct by electroporation (4D NUCLEOFECTOR®, Lonza) according to manufacturer's instructions. The cells are then returned to culture in complete medium for overnight incubation, then frozen at −80 C. Transfected cells are thawed and incubated for another 7 days in the presence of complete medium and supernatant samples are collected and frozen at 4 h, 1 day, 2 days, 3 days, 5 days and 7 days after thaw. Thawed cells and supernatants are assayed for viability and activity according to the methods described below.

MSCs obtained from the above-described process can be tested for viability, DNASE1 and DNASE1L3 expression, and DNA- and chromatin-degrading capacity. For example, viability is determined by flow cytometry on a GUAVA® EASYCYTE® 12HT Flow cytometer (EMD Millipore). To test viability, a sample of the MSCs is mixed with propidium iodide and run on the flow cytometer with electronic gating on fluorescence in the near infrared channel. To test expression of DNASE1 and DNASE1L3, commercially available DNASE1 and DNASE1L3 kits (i.e., Abbexa) are used to assay supernatants of cultured MSCs according to the manufacturers' instructions. To test DNA degrading capacity of transfected MSCs, culture supernatants are tested with a fluorometric DNASE1 assay kit (i.e., AbCam) according to the manufacturer's instructions. To test chromatin degrading capacity of transfected MSCs, culture supernatants are first incubated with NETs generated from phorbol myristate acetate-activated human neutrophils. Neutrophils are isolated from fresh apheresis product by density grade centrifugation. Recombinant human DNASE1 and DNASE1L3 are used as positive controls. The amount of NET DNA released is determined by adding picogreen (Invitrogen), a DNA fluorescence dye, to the mixed culture and then quantified by fluorescence spectrometry.

It is expected that DNASE1- and DNASE1L3-transfected MSCs will express and secrete functional DNASE1 and DNASE1L3 constitutively over the course of at least 24 hours. It is further expected that MSCs will maintain the capacity to express and secrete functional DNASE1 and DNASE1L3 following freeze/thaw.

Thus, MSCs can be transfected with the inventive saRNA sequence to express and secrete functional DNASE1 and DNASE1L3 protein. The result of this process is inventive, i.e., DNase-secreting MSCs that are useful for therapeutic administration, e.g., to a person affected by ARDS.

Example 3: Production of Functional DNAse-Secreting NK Cells from an Inventive Combination of mRNA Constructs The following example is of human DNAse-secreting NK cells produced by introduction of an inventive combination of mRNA constructs that encode human DNASE1 and DNASE1L3.

Four separate mRNA constructs, corresponding respectively to SEQ ID NO: 1 (DNASE1), SEQ ID NO: 2 (DNASE1L3), SEQ ID NO: 4 (transmembrane IL-15) and SEQ ID NO: 8 (translation enhancer E3), are generated by in vitro transcription from DNA plasmids. The in vitro transcription is performed by T7 RNA polymerase from a linearized plasmid template. A polyadenine tail of about 150 adenine nucleotides is added enzymatically to each mRNA. A 7-methylguanosine cap is incorporated at the 5' end of each mRNA during the co-transcriptional RNA synthesis.

The first mRNA construct comprises, from 5' to 3': a 5' cap; a 5' UTR described as SEQ ID NO: 23; a Kozak sequence described in SEQ ID NO: 20; a sequence of SEQ ID NO:1; a 3' UTR described as SEQ ID NO: 24, and a 3' polyadenine tail of 150 adenine units or more.

The second mRNA construct comprises, from 5' to 3': a 5' cap; a 5' UTR described as SEQ ID NO: 23; a Kozak sequence described in SEQ ID NO: 20; a sequence of SEQ ID NO:2; a 3' UTR described as SEQ ID NO: 24, and a 3' polyadenine tail of 150 adenine units or more.

The third mRNA construct comprises, from 5' to 3': a 5' cap; a 5' UTR described as SEQ ID NO: 23; a Kozak sequence described in SEQ ID NO: 20; a sequence of SEQ ID NO:4; a 3' UTR described as SEQ ID NO: 24, and a 3' polyadenine tail of 150 adenine units or more.

The fourth mRNA construct comprises, from 5' to 3': a 5' cap; a 5' UTR described as SEQ ID NO: 23; a Kozak sequence described in SEQ ID NO: 20; a sequence of SEQ ID NO:8; a 3' UTR described as SEQ ID NO: 24, and a 3' polyadenine tail of 150 adenine units or more.

To prepare NK cells from mRNA constructs, NK cells are isolated from umbilical cord blood by CD3+ magnetic bead negative selection followed by CD56+ magnetic bead positive selection to obtain >98% pure NK cells that are >95% viable. These NK cells are expanded by incubation at 37° C. with 5% $CO_2$ in the presence of K562 feeder cells engineered to express membrane-bound IL-15 for about 14 days. The cells are resuspended in transfection buffer and simultaneously transfected with a mixture of the four aforementioned mRNA constructs by electroporation (4D NUCLEOFECTOR®, Lonza) according to manufacturer's instructions. The cells are then returned to culture in a standard medium containing IL-15 for overnight incubation, and then are frozen at −80 C. Transfected cells are thawed and incubated for another 7 days in the presence of complete medium containing IL-15 and supernatant samples are collected and frozen at 4 h, 1 day, 2 days, 3 days, 5 days and 7 days after thaw. Thawed cells and supernatants are assayed for viability and activity according to the methods described below.

NK cells obtained from the above-described process can be tested for viability, DNASE1 and DNASE1L3 expression, and DNA- and chromatin-degrading capacity. As an example, viability is determined by flow cytometry on a GUAVA® EASYCYTE® 12HT Flow cytometer (EMD Millipore). To test viability, a sample of the NK cells is mixed with propidium iodide and run on the flow cytometer with electronic gating on fluorescence in the near infrared channel. To test expression of DNASE1 and DNASE1L3, commercially available DNASE1 and DNASE1L3 kits (i.e., Abbexa) are used to assay supernatants of cultured NK cells according to the manufacturers' instructions. To test DNA degrading capacity of transfected NK cells, culture supernatants are tested with a fluorometric DNASE1 assay kit (i.e., AbCam) according to the manufacturer's instructions. To test chromatin degrading capacity of transfected NK cells, culture supernatants are first incubated with NETs generated from phorbol myristate acetate-activated human neutrophils. Neutrophils are isolated from fresh apheresis product by density grade centrifugation. Recombinant human DNASE1 and DNASE1L3 are used as positive controls. The amount of NET DNA released is determined by adding picogreen (Invitrogen), a DNA fluorescence dye, to the mixed culture and then quantified by fluorescence spectrometry.

It is expected that the NK cells transfected with the above-described constructs will express and secrete functional DNASE1 and DNASE1L3 constitutively over the course of at least 24 hours. It is further expected that NK cells will maintain the capacity to express and secrete functional DNASE1 and DNASE1L3 following freeze/thaw.

Thus, NK cells can be transfected with the inventive combination of mRNA sequences to express and secrete functional DNASE1 and DNASE1L3 protein. The result of this process is inventive, DNase-secreting, NK cells that are useful for therapeutic administration, e.g., to a person affected by ARDS.

Example 4: Production of Functional DNAse-Secreting MSCs from an Inventive Combination of mRNA Constructs The following example is of human DNAse-secreting MSCs produced by introduction of an inventive combination of mRNA construct that encode human DNASE1 and DNASE1L3.

Three separate mRNA constructs, corresponding respectively to SEQ ID NO: 1 (DNASE1), SEQ ID NO: 2 (DNASE1L3), and SEQ ID NO: 8 (translation enhancer E3), are generated by in vitro transcription from DNA plasmids. The in vitro transcription is performed by T7 RNA polymerase from a linearized plasmid template. A polyadenine tail of about 150 adenine nucleotides is added enzymatically to each mRNA. A 7-methylguanosine cap is incorporated at the 5' end of each mRNA during the co-transcriptional RNA synthesis.

The first mRNA construct comprises, from 5' to 3': a 5' cap; a 5' UTR described as SEQ ID NO: 23; a Kozak sequence described in SEQ ID NO: 20; a sequence of SEQ ID NO:1; a 3' UTR described as SEQ ID NO: 24, and a 3' polyadenine tail of 150 adenine units or more.

The second mRNA construct comprises, from 5' to 3': a 5' cap; a 5' UTR described as SEQ ID NO: 23; a Kozak sequence described in SEQ ID NO: 20; a sequence of SEQ ID NO:2; a 3' UTR described as SEQ ID NO: 24, and a 3' polyadenine tail of 150 adenine units or more.

The third mRNA construct comprises, from 5' to 3': a 5' cap; a 5' UTR described as SEQ ID NO: 23; a Kozak sequence described in SEQ ID NO: 20; a sequence of SEQ ID NO:8; a 3' UTR described as SEQ ID NO: 24, and a 3' polyadenine tail of 150 adenine units or more.

To prepare MSCs from RNA constructs, MSCs isolated from human umbilical cord are purchased from ATCC, thawed and expanded in T75 flasks by culture at 37° C. with 5% $CO_2$ in α-DMEM medium supplemented with 10% human serum. The cells are passaged upon reaching 80% confluency. The cells are resuspended in transfection buffer and simultaneously transfected with a mixture of the three aforementioned mRNA constructs by electroporation (4D NUCLEOFECTOR®, Lonza) according to manufacturer's instructions. The cells are then returned to culture in complete medium for overnight incubation, then frozen at −80 C. Transfected cells are thawed and incubated for another 7 days in the presence of complete medium and supernatant samples are collected and frozen at 4 h, 1 day, 2 days, 3 days, 5 days and 7 days after thaw. Thawed cells and supernatants are assayed for viability and activity according to the methods described below.

MSCs obtained from the above-described process can be tested for viability, DNASE1 and DNASE1L3 expression, and DNA- and chromatin-degrading capacity. As an example, viability is determined by flow cytometry on a GUAVA® EASYCYTE® 12HT Flow cytometer (EMD Millipore). To test viability, a sample of the MSCs is mixed with propidium iodide and run on the flow cytometer with electronic gating on fluorescence in the near infrared channel. To test expression of DNASE1 and DNASE1L3, commercially available DNASE1 and DNASE1L3 kits (i.e., Abbexa) are used to assay supernatants of cultured MSCs according to the manufacturers' instructions. To test DNA degrading capacity of transfected MSCs, culture supernatants are tested with a fluorometric DNASE1 assay kit (i.e., AbCam) according to the manufacturer's instructions. To test chromatin degrading capacity of transfected MSCs, culture supernatants are first incubated with NETs generated from phorbol myristate acetate-activated human neutrophils. Neutrophils are isolated from fresh apheresis product by density grade centrifugation. Recombinant human DNASE1 and DNASE1L3 are used as positive controls. The amount of NET DNA released is determined by adding picogreen (Invitrogen), a DNA fluorescence dye, to the mixed culture and then quantified by fluorescence spectrometry.

It is expected that the MSCs transfected with the above-described constructs will express and secrete functional DNASE1 and DNASE1L3 constitutively over the course of at least 24 hours. It is further expected that MSCs will maintain the capacity to express and secrete functional DNASE1 and DNASE1L3 following freeze/thaw.

Thus, MSCs can be transfected with the inventive combination of mRNA sequences to express and secrete functional DNASE1 and DNASE1L3 protein. The result of this process is inventive, i.e., DNase-secreting, MSCs that are useful for therapeutic administration, e.g., to a person affected by ARDS.

Example 5: In Vivo Safety and Efficacy of Functional DNAse-Secreting MSCs in a Mouse Model of ALI DNAse-secreting MSCs produced from inventive RNA constructs comprising the nucleotide sequences of SEQ ID NO: 1 and SEQ ID NO: 2, were tested in an Acute Lung Injury (ALI) animal model of ARDS. In this model, ALI is first induced by the intratracheal administration of lipopolysaccharide (LPS), and MSCs are then administered by intravenous injection.

DNAse-secreting MSCs were prepared by transfection of the inventive RNA constructs, as discussed in Example 2. 8-12 week old C57BL/6 mice were anesthetized and administered 2 mg/kg of LPS solution by an intratracheal catheter. At 4 hours after LPS administration, mice were randomized to receive intravenous vehicle only (negative control), $1\times10^6$ untransfected MSCs (negative control), or $1\times10^6$ DNAse-secreting MSCs. 5 animals were assigned to each group.

12 hours after MSC administration, mice were anesthetized and bronchoalveolar lavage fluid (BALF) was collected with 1 mL phosphate buffered saline (PBS) solution. 0.5 mL of BALF was frozen without fixation for analysis of TNF-α, IL-6 and IL-10 by commercially available murine ELISA kits or for NET formation by Quant-iT dsDNA HS kit (Invitrogen). 0.5 mL of BALF was collected into Cyto-Chex® BCT Tubes (Streck) for analysis of total cell infiltrate and infiltration of specific cell types (i.e., macrophages, neutrophils and lymphocytes) by flow cytometry.

Two mice from each group were sacrificed 24 hours after LPS administration and lung tissue was collected. Each lung was fixed in 4% formalin solution and processed for H&E staining. The remaining animals were followed for up to 5 days before being sacrificed and processed as above. Inflammation scores were quantified with Image Pro Plus software (Media Cybernetics).

The DNAse-secreting MSC group is expected to show fewer inflammatory cells from BALF, lower amounts of TNF-α and IL-6 from BALF, less NET formation, and lower inflammatory scores on histology compared with the untransfected MSC group and vehicle only-treated animals. Furthermore, animals in the DNAse-secreting MSC group are expected to survive longer compared with the control groups.

Thus, DNAse-secreting MSCs are expected to reduce ALI and improve survival in a murine model of ARDS.

Example 6: Clinical Safety and Efficacy of Functional DNAse-Secreting MSCs in Patients with ARDS A randomized clinical trial is conducted to test inventive, DNAse-secreting MSCs in patients with ARDS. The clinical trial enrolls 20 patients who meet the following criteria: at least 18 years old; ARDS per Berlin Criteria; and current endotracheal intubation with mechanical ventilation. The patients are randomized in a 1:1 ratio to receive standard of care with or without DNAse-secreting MSCs. DNAse-secreting MSCs are made according to Example 2, supra. For those patients thus randomized, the DNAse-secreting MSCs are administered at a dose of about $1.1\times10^9$ cells daily for three successive days. It is expected that following the initiation of treatment, e.g., 24 to 96 hours after the first dose, patients who receive the MSCs will, compared to those who do not receive the MSCs, show more rapid improvement of clinical status as measured by PaO2/FiO2 (ratio of arterial partial pressure of O2 to fraction of inspired O2), time to extubation, and survival.

Example 7: Production of Bifunctional Anti-BCMA Bispecific Antibody and DNAse-Secreting MSCs from an Inventive saRNA Construct The following example is of MSCs modified to secrete a DNAse enzyme and a bispecific antibody. Namely, the MSCs of this example are human MSCs modified by the introduction of saRNA to express human DNASE1, human DNASE1L3, and a bispecific antibody directed to human BCMA and human CD3. The bispecific antibody of this example is also referred to as a bispecific T-cell engager.

An inventive saRNA construct, described hereunder, is generated by in vitro transcription from a DNA plasmid. The in vitro transcription is performed by SP6 RNA polymerase from a linearized plasmid template. A polyadenine tail of about 150 adenine nucleotides is added enzymatically to the saRNA. A 7-methylguanosine cap is incorporated at the 5' end of the saRNA during the co-transcriptional RNA synthesis.

The inventive saRNA construct comprises, from 5' to 3': a 5' cap, a 5' UTR described as SEQ ID NO: 15, an RNA-dependent RNA polymerase (RDRP) sequence described as SEQ ID NO: 17, DNASE1 open reading frame (ORF) described as SEQ ID NO: 1, a T2A sequence described in SEQ ID NO: 14, a DNASE1L3 ORF described as SEQ ID NO: 2, a T2A sequence described as SEQ ID NO: 14, an anti-BCMA-CD3 bispecific antibody ORF described as SEQ ID NO: 21, a T2A sequence described in SEQ ID NO: 14, a translation enhancer ORF described as SEQ ID NO: 8, a 3' UTR described as SEQ ID NO: 16, and a 3' polyadenine tail of 150 adenine units or more. The construct can be represented as follows:

| Cap | 5' UTR | NSP1-NSP4 | 26S promoter | C protein | DNASE1L3 | T2A | DNASE1 | T2A | Bispec | 3' UTR | polyA |
|---|---|---|---|---|---|---|---|---|---|---|---|

A translation enhancer mRNA construct described by sequence of SEQ ID NO: 8 is generated by in vitro transcription from a DNA plasmid. The in vitro transcription is performed by SP6 RNA polymerase from a linearized plasmid template. A polyadenine tail of about 150 adenine nucleotides is added enzymatically to the mRNA. A 7-methylguanosine cap is incorporated at the 5' end of the mRNA during the co-transcriptional RNA synthesis. The translation enhancer mRNA construct comprises, from 5' to 3': a 5' cap, a 5' UTR described as SEQ ID NO: 15, a Kozak sequence described in SEQ ID NO: 20, the open reading frame (ORF) described by the sequence of SEQ ID NO: 8, a 3' UTR described as SEQ ID NO: 16, and a 3' polyadenine tail of 150 adenine units or more.

To prepare MSCs from RNA constructs, MSCs isolated from human umbilical cord are purchased from ATCC, thawed and expanded in T75 flasks by culture at 37° C. with 5% $CO_2$ in DMEM medium supplemented with 10% human serum. The cells are passaged upon reaching 80% confluency. The cells are resuspended in transfection buffer and transfected with a mixture of the saRNA construct and mRNA construct by electroporation (4D NUCLEOFEC- TOR®, Lonza) according to manufacturer's instructions. The cells are then returned to culture in complete medium for overnight incubation, then frozen at −80° C. The transfected cells are thawed and incubated for another 7 days in the presence of complete medium and supernatant samples are collected and frozen at 4 h, 1 day, 2 days, 3 days, 5 days and 7 days after thaw. Thawed cells and supernatants can be assayed for viability and activity according to the methods described below.

MSCs obtained from the above-described process can be tested for viability, DNASE1 and DNASE1L3 expression, DNA- and chromatin-degrading capacity. As an example, viability is determined by flow cytometry on a GUAVA® EASYCYTE® 12HT Flow cytometer (EMD Millipore). To test viability, a sample of the MSCs is mixed with propidium iodide and run on the flow cytometer with electronic gating on fluorescence in the near infrared channel. To test expression of DNASE1 and DNASE1L3, commercially available DNASE1 and DNASE1L3 kits (i.e., Abbexa) are used to assay supernatants of cultured MSCs according to the manufacturers' instructions. To test DNA degrading capacity of transfected MSCs, culture supernatants are tested with a fluorometric DNASE1 assay kit (i.e., AbCam) according to the manufacturer's instructions. To test chromatin degrading capacity of transfected MSCs, culture supernatants are first incubated with NETs generated from phorbol myristate acetate-activated human neutrophils. Neutrophils are isolated from fresh apheresis product by density grade centrifugation. Recombinant human DNASE1 and DNASE1L3 are used as positive controls. The amount of NET DNA released is determined by adding picogreen (Invitrogen), a DNA fluorescence dye, to the mixed culture and then quantified by fluorescence spectrometry.

MSCs obtained from the above-described process were tested for their capacity to secrete functional anti-BCMA-CD3 bispecific antibody, i.e., the ability to kill BCMA+ myeloma (tumor) cells in the presence of naïve CD3+ T-cells. To test the capacity of MSCs to secrete anti-BCMA-CD3 bispecific antibody, supernatant from engineered MSC cultures was collected and assayed by Western blot with anti-TAG antibody directed to the bispecific protein. To test the capacity of engineered MSCs to kill BCMA+ myeloma cells in the presence of naïve CD3+ T-cells, supernatant from MSC cultures were collected and added to co-cultures of BCMA+ myeloma cell line expressing green fluorescent protein (MM.1S-GFP) and unlabeled bystander CD3+ T-cells. T-cells were collected from healthy volunteers by Ficoll separation of mononuclear cells followed by CD3+ bead positive selection. Aliquots of 50,000 MM.1S-GFP tumor cells were placed in wells of a 96-well plate, and between 2,500 to 50,000 T-cells were added to each well to obtain various effector:target ratios (i.e., ratios of T cells to BCMA+ myeloma cells) that were between about 1:1 and 1:20. 100 μL of MSC supernatant was then added to experimental wells. Negative controls included 100 μL of supernatant collected from untransfected MSCs, MM1.S tumor cells alone in the absence of T-cells, or T-cells alone in the absence of MM1.S tumor cells. Following overnight incubation, propidium iodide was used to stain dead cells. Viable target cells were identified, and cell density was determined by flow cytometry. The degree of myeloma cell killing by engineered MSC supernatant was calculated by comparison to the number of myeloma cells in wells concurrent control wells that did not contain engineered MSC supernatant.

It is expected that bifunctional anti-BCMA bispecific antibody, DNASE1 and DNASE1L3 transfected MSCs will express and secrete their respective functional proteins constitutively over the course of at least 24 hours. It is further expected that engineered MSCs will maintain the capacity to express and secrete functional anti-BCMA bispecific antibody, DNASE1 and DNASE1L3 following freeze/thaw.

Thus, MSCs can be transfected with the inventive saRNA sequence to express and secrete functional anti-BCMA bispecific antibody, DNASE1 and DNASE1L3 protein. The result of this process is inventive, i.e., bifunctional anti-BCMA bispecific antibody and DNase-secreting MSCs that are useful for therapeutic administration, e.g., to a person affected by autoimmune diseases, e.g. generalized myasthenia gravis.

Example 8: Direct Comparison of Different Cells Types for Use in the Present Invention The following example describes a direct, head-to-head comparison of the chromatin-degrading activity of four different human cell types, each modified by identical methods to secrete a combination of DNASE1 and DNASE1L3. The study showed that MSCs were qualitatively superior to CD4+ T cells, CD8+ T cells, and NK cells.

Umbilical MSCs were expanded in 2D vessels with standard culture medium. Naïve human CD4+ or CD8+ T cells were activated (anti-CD3) and expanded as known in the art. NK cells were obtained by negative-CD3 selection and cultured in medium supplemented with IL-15, and then selectively expanded by addition of mitomycin-treated K562 cells, as known in the art. The experimental operators had experience with culture of all of these cell types. Upon expansion, the above cells showed viability.

Comparable samples of the four aforementioned cell types (in each case $10^6$ cells) were electroporated by identical methods with either of the following:

a. sterile water (control); or
b. 2 μg of mRNA encoding Green Fluorescent Protein (GFP); 2 μg of mRNA encoding DNASE1 (i.e., SEQ ID NO: 1); and 2 μg of mRNA encoding DNASE1L3 (i.e., SEQ ID NO: 2), wherein substantially all of the uridines were substituted with pseudouridine.

The Purpose of the GFP was to Verify that Electroporation and Viability were Consistent Across the Four Aforementioned Cells Types.

Transfected cells were plated with 2 mL culture medium per well. Supernatants were harvested 24 hours after transfection, and cells were harvested for phenotyping.

Cells were phenotyped by flow cytometry. The MSC cell sample was >90% CD90+CD105+. The CD4+ T cell sample was >95% CD4+. The CD8+ cell sample was >86% CD8+. The NK cell sample was 50% CD56+CD3−. Samples of all four cell types were >90% GFP+.

The supernatant samples were tested with a chromatin digestion (degradation) assay as described in Example 1, supra. The results are shown in the gel electrophoresis of FIG. 1. Where "no supernatant" was included in the digestion assay, the chromatin was not degraded (negative controls). Likewise, in "untransfected" cells—i.e., each of MSCs, CD4+ T cells, CD8+ T cells, and NK cells—chromatin was not degraded (negative controls).

For cells transfected with mRNA to secrete a combination of DNASE1 and DNASE1L3, as described hereinabove, different cell types were associated with different levels of chromatin-degrading activity. CD8+ T cells had the least activity, followed by CD4+ T cells, then NK cells. Each of the foregoing cell types provided only partial chromatin degradation. MSCs, on the other hand, provided complete chromatin degradation, with substantially all degradation products at 180 bp or less.

Thus, in a direct head-to-head comparison of different cell types modified with mRNA to express a combination of DNASE1 and DNASE1L3, MSCs provided superior chromatin-degrading activity. Furthermore, the MSCs were qualitatively superior to the other cell types tested, because only the MSCs provided for complete chromatin digestion.

Example 9: Synergistic Activity of Cells Secreting a Combination of DNASE1 and DNASE1L3 Proteins The following example shows that MSCs modified by mRNA electroporation to co-express both DNASE1 and DNASE1L3 possessed chromatin-degrading activity that was synergistically and qualitatively superior to MSCs modified to express either enzyme alone.

Umbilical MSCs were expanded in 2D vessels with standard culture medium, and $1\times10^6$ cells were electroporated with water or mRNA as follows:

a. sterile water (control);

b. 2 μg of mRNA encoding DNASE1 (i.e., SEQ ID NO: 1);

c. 2 μg of mRNA encoding DNASE1L3 (i.e., SEQ ID NO: 2), wherein substantially all of the uridines were substituted with pseudouridine; or d. 2 μg of mRNA encoding DNASE1 (i.e., SEQ ID NO: 1) and 2 μg of mRNA encoding DNASE1L3 (i.e., SEQ ID NO: 2), wherein substantially all of the uridines were substituted with pseudouridine.

Transfected cells were plated into 6-well plates supplemented with 2 mL culture medium per well. The supernatant was harvested from each well 24 hours after transfection, the wells were washed, and 2 mL culture medium was added to each well. The supernatant was harvested from each well 5 days after transfection, and these supernatant samples were tested with a chromatin digestion (degradation) assay as described in Example 1, supra.

The results of the chromatin digestion assay are shown in FIG. 2. Where the MSCs were unmodified (condition "a", negative control), chromatin was not degraded. Where the MSCs were modified to express DNASE1 (condition "b"), chromatin was only partly degraded; the products of degradation were highly variable and indicated degradation at nonspecific sites, as the lane showed a smear indicating a panoply of DNA/chromatin fragment sizes. Where the MSCs were modified to express DNASE1 and DNASE1L3 (the latter by means of a pseudouridine-substituted mRNA, condition "c"), chromatin was only partially degraded, but in a different pattern from that of condition "b"; here, a laddering pattern was seen wherein the fragments were multiples of 180 bp, e.g., 180, 360, 540, 720, and 900 bp.

Where the MSCs were modified to express both DNASE1 and DNASE1L3 (condition "d"), a surprising result occurred that was not only synergistic, but also qualitatively distinct from either condition "b" or condition "c.". The DNA was almost completely digested to fragments of 180 bp.

Thus, MSCs modified by mRNA electroporation to co-express both DNASE1 and DNASE1L3 possessed chromatin-degrading activity that was synergistically and qualitatively superior to MSCs modified to express either of those enzymes alone.

Example 10: Characterization of GR-17, Human Mesenchymal Stem Cells Electroporated with mRNA Encoding Human DNASE1 and DNASE1L3

A series of six related in vitro studies was conducted to determine the mRNA expression, protein expression, and activity of GR-17, human mesenchymal stem cells (MSCs) electroporated with mRNA encoding human DNASE1 and DNASE1L3.

Human MSCs derived from either adult bone marrow or umbilical cord were purchased from RoosterBio, Inc. (Frederick, MD). Serum-free MSC growth media (e.g., Rooster-Nourish) was purchased from RoosterBio. Cells were thawed and maintained in culture at 37° C. Cells were split by incubating in trypsin (Sigma) for 10 min, harvesting, and re-plating at a maintenance ratio for continued cell growth. Neutrophils were maintained in ExCellerate media (R&D Systems) supplemented with 100× GlutaMax (Gibco).

Time Quantitative PCR was performed to evaluate level of mRNA transcripts. mRNA was extracted from cells using an RNEasy kit (Qiagen) according to the manufacturer's instructions and quantitated by absorption at A260 using a Nanodrop spectrophotometer (ThermoFisher). First-strand cDNA was generated using Superscript IV reverse transcriptase (ThermoFisher) and real-time quantitative PCR was performed using a SYBR green PCR 2× master mix (ThermoFisher) and gene-specific primers for either DNASE1 (forward-AGCTGGCTAGCTCTAAAGAAGC (SEQ ID NO: 25); reverse-TCTCCGAATGTCTGGATATTAAAGGC (SEQ ID NO: 26)) or DNASE1L3 (forward-AAGCAACAGCGTCTTCGAC (SEQ ID NO: 27); reverse-ATCTTTGTAGTCAGAGCCGCC (SEQ ID NO:28)). Amplification was performed on a MX3005P thermal cycler (Stratagene). Quantitation of mRNA was determined by comparison with standard curves generated using known quantities of plasmid DNA for DNASE1 or DNASE1L3.

To perform Western blots, 30 μL of GR-17 or control supernatant was added to 10 μL of 4× Laemmli loading buffer with (reducing) or without (non-reducing) 2-mercaptoethanol and denatured at 70° C. for 5 minutes. SDS-PAGE was performed using 4-20% Tris-glycine gradient gels and proteins were transferred onto PVDF membranes for Western blotting. Following blocking with 5% milk, blots were probed with mouse monoclonal anti-DNASE1 (B-4 clone, Santa Cruz sc-376207) followed by goat anti-mouse HRP (Abcam ab97040). For detection of DNASE1L3, 1 ml MSC control cell or GR17-transfected cell culture medium at 24-hour post electroporation, was used to pull down with 50 ul Heparin Sepharose. The resin was then washed twice with 1 ml 10 mM Tris HCL pH 7.5 and mixed with 4× Laemmli loading buffer with 2-mercaptoethanol and denatured at 70° C. for 5 minutes and proteins transferred to PVDF membrane as above. DNASE1L3 was detected with rabbit polyclonal anti-DNASE1L3 antibody (Sigma SAB2107648) followed by goat anti-rabbit HRP antibody (Abcam ab7090). The antibodies were detected by addition of Radiance Q (Azure Biosystems) and imaging of chemiluminescence using a C280 Imager (Azure Biosystems). The specificity and sensitivity of the Western blotting were evaluated by spiking culture media with or without reference control proteins for DNASE1 (Abcam ab73430) or DNASE1L3 (FLAG-tagged, produced using Origene RC205611; or GST-tagged Abcam ab238220), and comparison of protein bands with a Precision Plus Dual Color reference ladder (Biorad 1610374).

To prepare chromatin, MM1S cells (human myeloma cell line) were centrifuged, and the pellet was disrupted by gentle flicking and resuspended in 4° C. lysis buffer (0.5% Triton X-100 in 10 mM Tris pH 7.8 with 150 mM NaCl) at 100M/mL. The cells were gently vortexed and incubated on ice for 10 min. The nuclei were pelleted by centrifugation and resuspended in ice-cold PBS at 10M/mL. An equal volume of glycerol was added, and the nuclei were stored in aliquots at −80° C.

To prepare NETs, neutrophil polymorphonuclear granulocytes (PMNs) were isolated from whole blood within 2 hours after collection with Histopaque-1119 (Sigma) and Lymphoprep (Stemcell Technologies) according to the manufacturers' instructions. 10 mL of red cell lysis buffer (ACK buffer, Sigma) was added and the solution incubated at room temperature for 6 to 8 minutes. The cells were washed twice and resuspended in serum-free media at the desired concentration.

To induce NETosis, freshly isolated neutrophils were resuspended in serum-free neutrophil media (see above for culture conditions) and 100 nM PMA (Sigma-Aldrich). The desired number of cells (e.g. $10^5$) was added to each well of a 96-well flat-bottom CellBind plate (Corning) in 100 uL and the cells were incubated at 37° C. Following overnight incubation, the plates were centrifuged at 200×g for 3 minutes. NET formation was confirmed by adding a 1:500 dilution of Sytox Green (Life Technologies) per manufacturer's protocol and examined under fluorescent microscopy using a Cytation-5 Imaging system (BioTek). The plates were stored at 4° C. for up to 1 month to be used in NET digestion assays.

DNA degradation assays were performed using chromatin (15K lysed nuclei), NETs (equivalent of 100K neutrophils) or naked DNA (1 μg purified R' plasmid) using the following procedure. A 2× master mix of DNA and buffer (including 10×DNASE1 digestion buffer, New England Biolabs NEB #B0303S) was prepared on ice and added to 10 μL of undiluted sample or sample diluted in nuclease-free $H_2O$. Recombinant human DNASE1 (Abcam ab73430) and recombinant human DNASE1L3 (produced in 293 cells using Origene RC205611) were added to separate reactions as controls. DNA digestion was performed by incubating samples for 30 minutes at 37° C. in a water bath. The reaction was stopped by adding 1 μL of 100 mM EDTA to each tube, and the protein was digested by the addition of 2 μl of 20 mg/mL of Proteinase K. The reaction was incubated for another 20 minutes at 37° C. The nucleic acid was extracted by addition of an equal volume of Phenol:Chloroform:Isoamyl Alcohol 25:24:1 (Sigma), gentle vortexing and centrifugation at 16,000×g for 10 minutes at room temperature. The aqueous layer was added to 6×DNA loading dye and resolved on a 1.5% agarose gel containing Gel-Red nucleic acid stain (Biotium) in comparison with a 100 bp DNA ladder (NEB N04675). Images were captured using a C280 Imager (Azure Biosystems).

Figure 3:
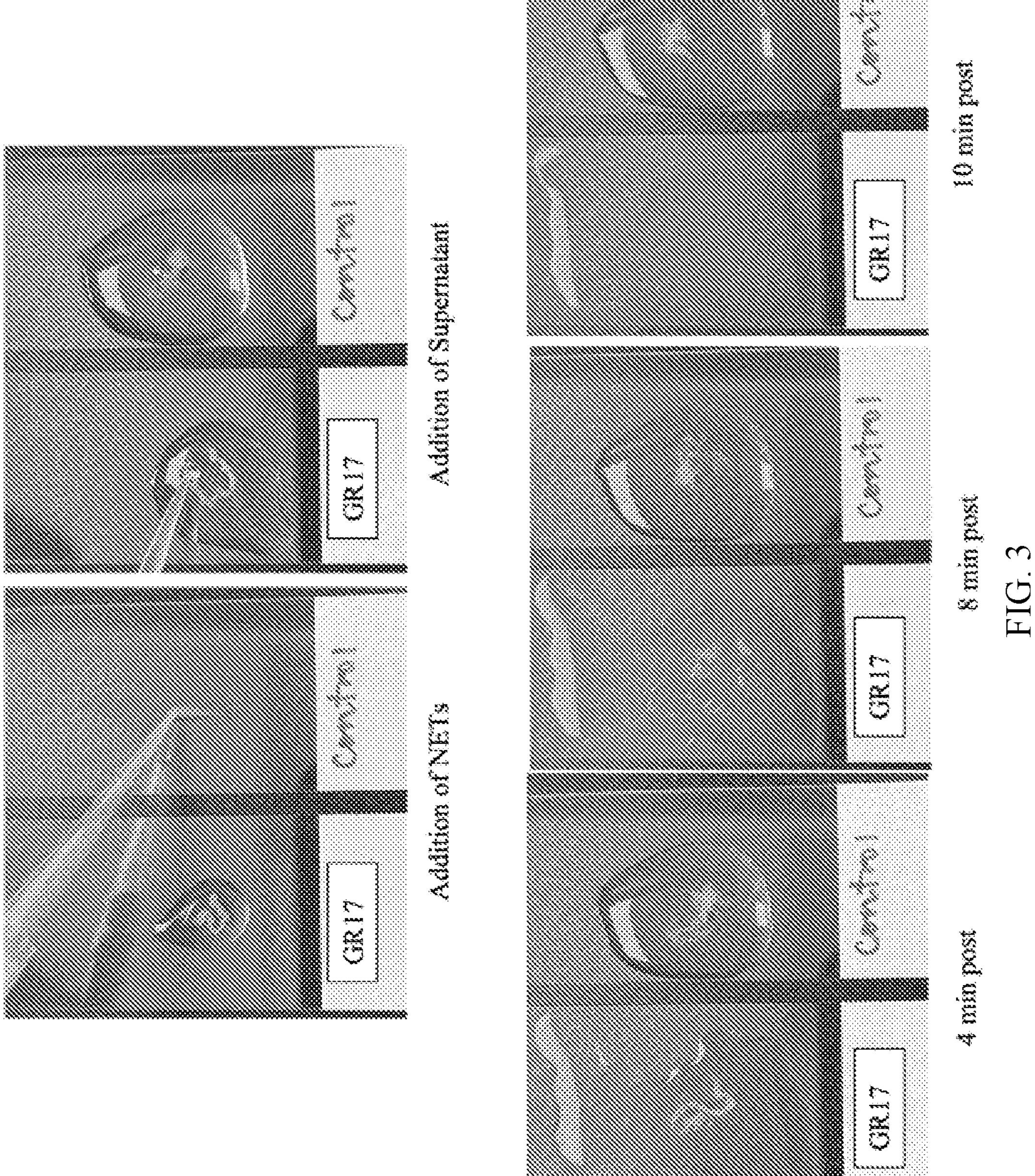
FIG. 3 shows a series of photographs wherein macroscopic amounts of NETs are degraded by GR-17 supernatants. The photographs show the addition of NETs, the addition of supernatant, 4 minutes post addition, 8 minutes post addition, and 10 minutes post addition.

Study GR17-1 visualized the capacity of GR-17 cells to degrade large quantities of NETs that were visible macroscopically. $1.5\times10^6$ MSCs were transfected with DNASE1 and DNASE1L3 mRNA or irrelevant control mRNA (R'; see IND 19050 construct) synthesized in identical fashion. Transfected cells were plated on a 6-well CellBind plate in 1 ml of RoosterBio media for 48 hours. Supernatants were collected and added directly to slides containing large quantities of visible, viscous NETs generated from $4\times10^6$ neutrophils, and the slides were incubated on a 37° C. heat block. The slides were videographed and photographic clips were captured at various timepoints. GR-17 supernatant, but not control MSC supernatant, degraded large quantities of NETs (FIG. 3). Partial degradation was noticeable within the first 5 minutes. Degradation was complete within about 10 minutes. It was concluded that GR-17 degrades large, visible quantities of NETs within minutes.

Figure 4A:
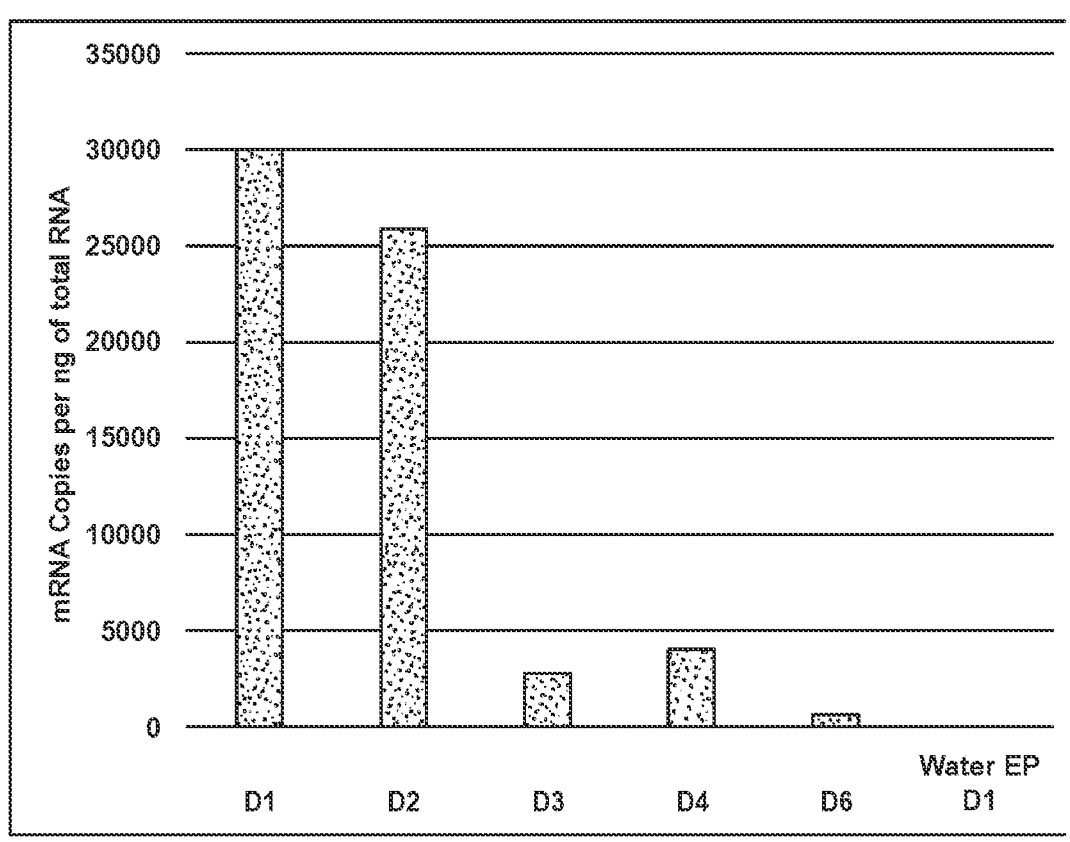
FIGS. 4A-4B shows the levels of DNase-encoding mRNA over time in MSCs. GR-17 samples were prepared, frozen, and thawed. MSCs were incubated for up to 6 days (D1 to D-6) in complete media. mRNA was assayed by quantitative RT-PCR using primers specific for DNase1 and DNase1L3. Results are expressed as mRNA copies per total cell RNA.
Figure 4B:
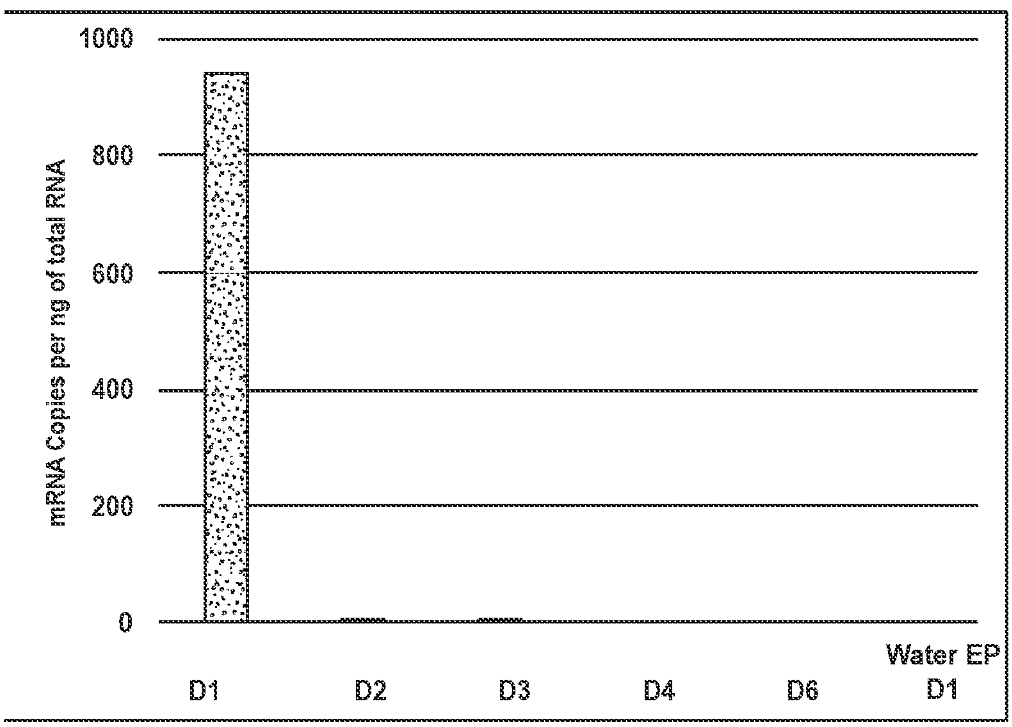
Figure 5A:
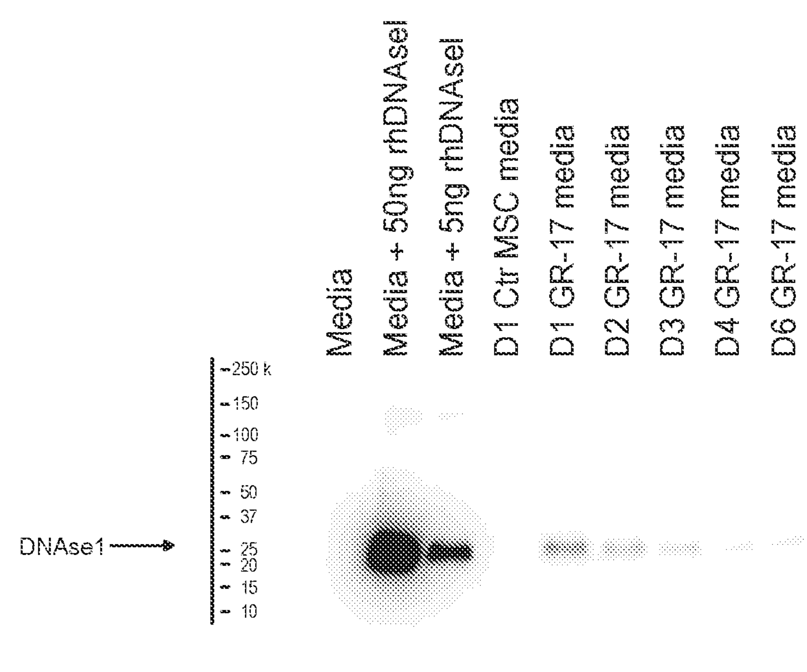
FIGS. 5A-5B show the level of DNASE1 and DNASE1L3 expression using Western blot analysis. GR-17 was prepared, frozen, and thawed. MSCs were incubated for up to 6 days (D1 to D-6) in complete media. DNase1 and DNase1L3 protein were assayed by Western Blot.
Figure 5B:
Figure 6A:
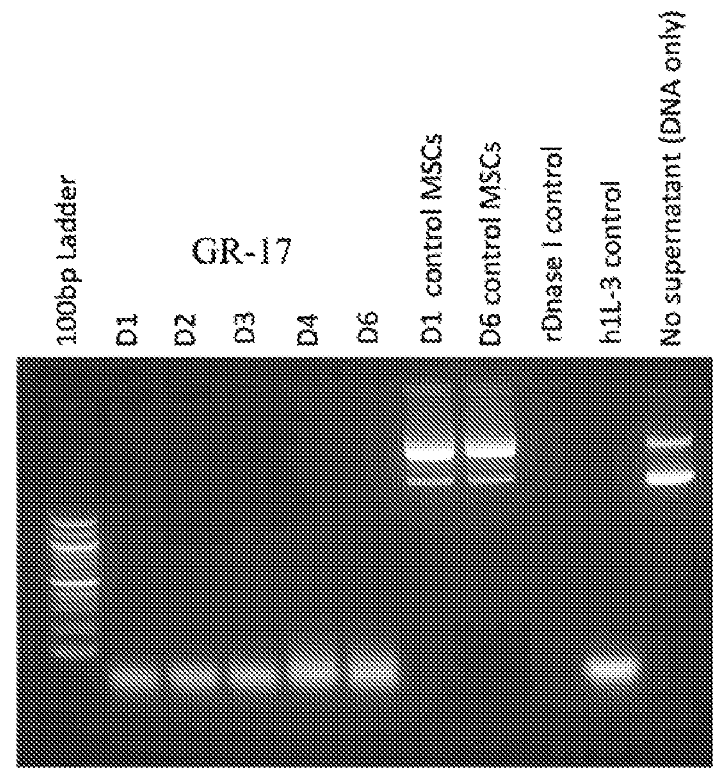
FIGS. 6A-6D show the results of a chromatin degradation assay using DNA electrophoresis following treatment of naked DNA, chromatin, and NETs. GR-17 was prepared, frozen, and thawed. MSCs were incubated for up to 6 days (D1 to D-6) in complete media. Supernatant was collected at the indicated timepoints and assayed for its capacity to degrade cell-free naked DNA (FIG. 6A), chromatin (FIG. 6B), and NETs (FIG. 6C). Negative controls include water-transfected MSC supernatants at Days 1 and 6 and no-supernatant control. Positive controls are exogenous recombinant human DNase1 and purified human DNase1L3.
Figure 6B:
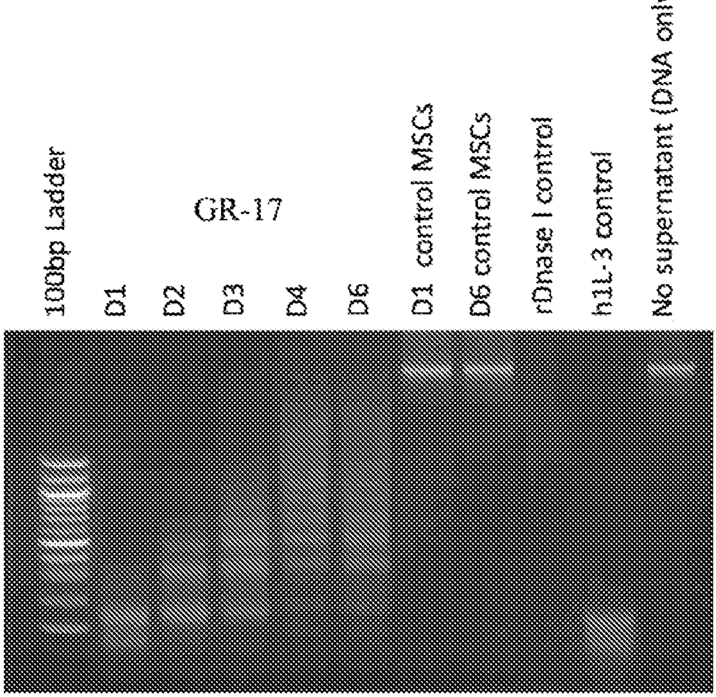
Figure 6C:
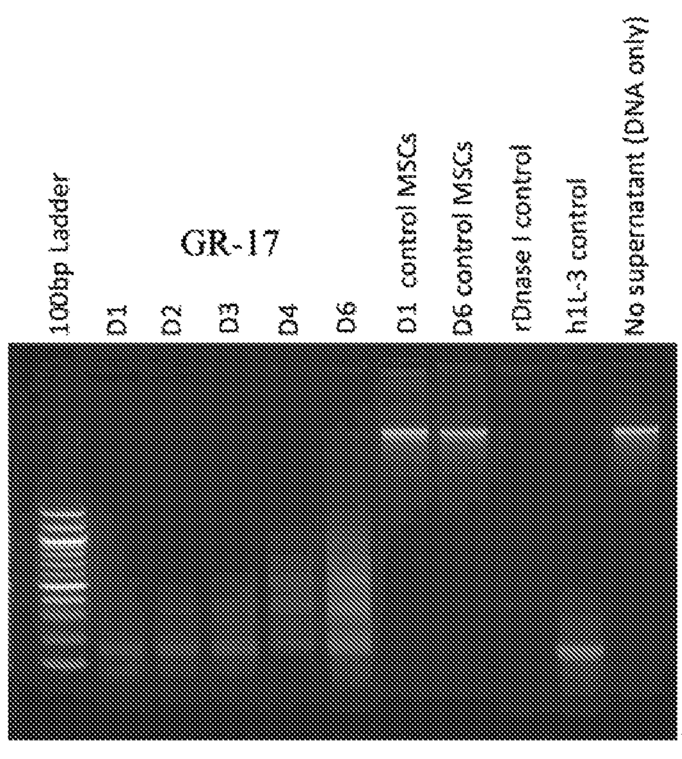
Figure 6D:
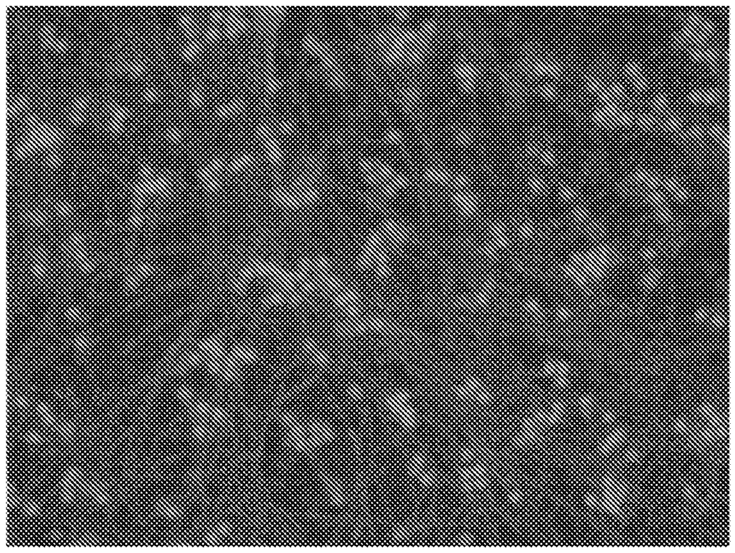

Study GR17-2 determined the presence of mRNA, DNase secretion, and NET-degrading capacity of GR-17 cells over 1 week in cell culture. 10 million human MSCs were electroporated using 100 μL cuvettes with 1 μg of mRNA encoding human DNASE1 and DNASE1L3, cultured for 2 hours, frozen, stored overnight at −80° C., thawed, and cultured at 37° C. for up to 6 days in RoosterNourish media (RoosterBio, Frederick, MD). Cell lysates were collected to detect mRNA by RT-qPCR analysis. Supernatants were collected to detect DNase protein by Western blot. Supernatant was also used to assay enzyme activity by degradation of naked DNA, chromatin, and neutrophil extracellular traps (NETs). GR-17 cells expressed DNase mRNA that waned off over days (FIGS. 4A-4B). DNASE1 mRNA was detectable at higher copy numbers and for a longer time compared with DNASE1L3 mRNA (FIG. 4A vs 4B; compare peak copies per ng total mRNA of 30,000 vs. 950 and compare undetectable mRNA at 6 days vs 2 days). Waning mRNA translated to reduced protein expression over time (FIGS. 5A-5B); and peak expression of both proteins was at Day 1. DNASE1-protein expression was reduced over days and was only faintly detectable at Day 6 (FIG. 5A). DNASE1L3 protein was detectable at Day 1 only (FIG. 5B). Waning protein expression translated to reduced enzymatic activity over time (FIGS. 6A-6D). peak activity was measured at Day 1 and waned over 6 days as measured by the capacity of supernatant to degrade cell-free naked DNA, chromatin, and NETs (FIGS. 6A-6D). A representative fluorescent micrograph of NETs is provided in FIG. 6D. It was concluded that GR-17 expresses DNASE1 and DNASE1L3 protein that degrades NETs. Activity wanes over about 1 week likely due to transient expression of mRNA.

Figure 7A:
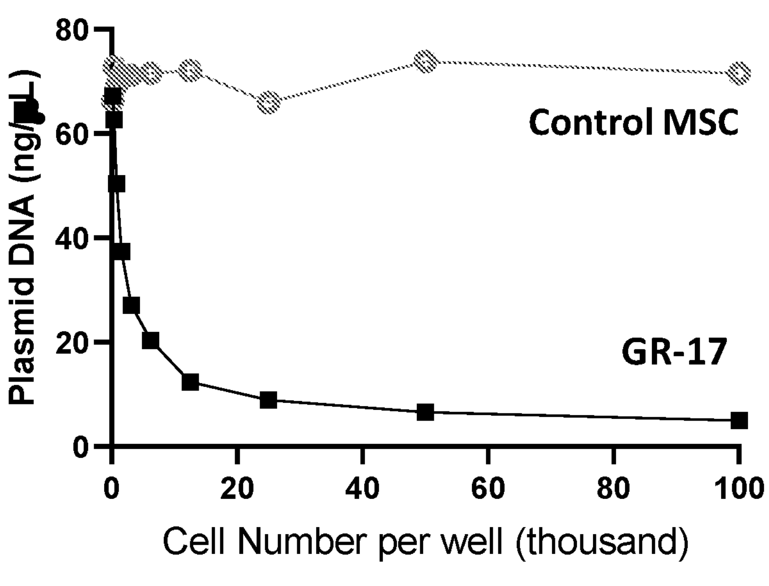
FIGS. 7A-7C chart the time- and dose-dependence of naked DNA and NET degradation by MSCs. Increasing concentrations of GR-17 or control MSCs were cultured overnight in the presence of naked DNA (FIG. 7A) or NETs (FIG. 7B).
Figure 7B:
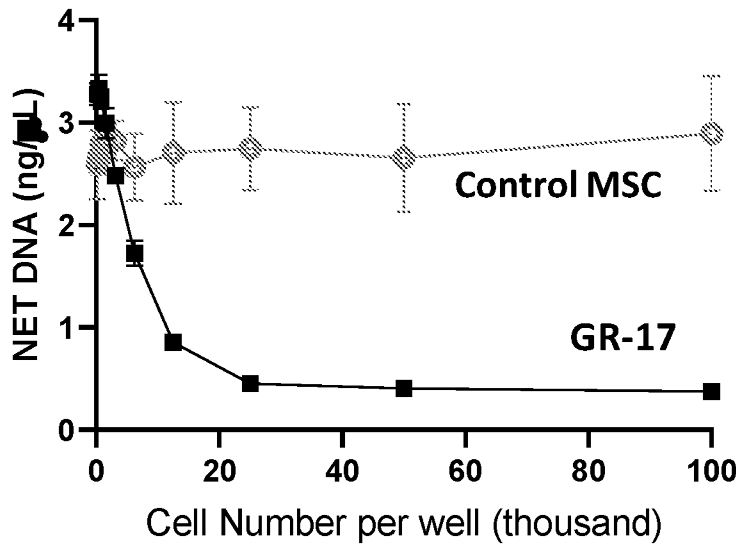
Figure 7C:
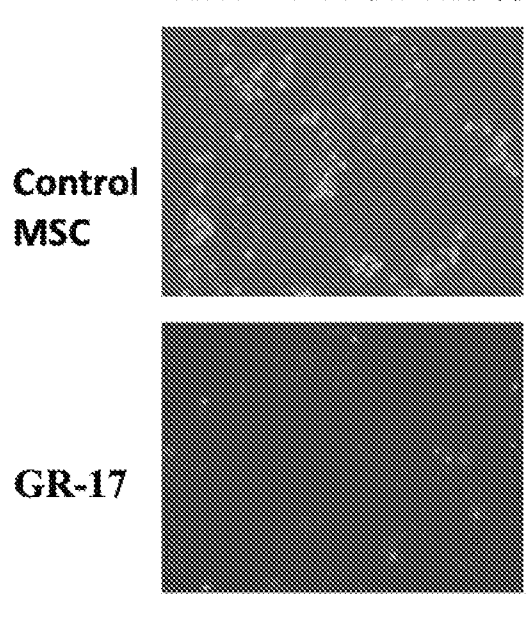

Study GR17-3 assessed the dose-dependent NET-degrading capacity of GR-17 cells when cultured directly with exogenous NETs, which may better reflect conditions in the human lung with ARDS. Human MSCs were transfected with DNASE1 mRNA and DNASE1L3 mRNA (GR-17) or water (control MSCs) and cultured overnight in 96-well plates. Media was removed and fresh media containing 20 μg/mL of naked DNA or 100 μL NETs (generated from 100,000 neutrophils incubated with 100 nM PMA) was added directly onto MSCs. The cells were cultured overnight and assayed for degradation of DNA or NETs as described above. Control MSCs did not degrade either cell-free naked DNA or NETs when incubated in culture overnight. The GR-17 cells degraded naked DNA (FIG. 7A) and NETs (FIGS. 7B, 7C) in a dose-dependent manner. GR-17 viability was unaffected in the presence of exogenous NETs. A representative fluorescent micrograph of NETs is provided in FIG. 7C. It was concluded that GR-17 degrades cell-free naked DNA and NETs in a dose-dependent manner.

Figure 8:
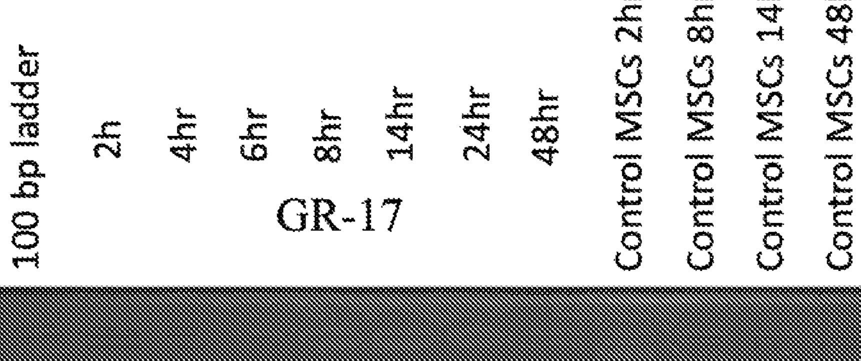
FIG. 8 shows the results of a chromatin degradation assay using DNA electrophoresis conducted to assess degradation of NETs over time by MSCs. GR-17 or control MSCs were cultured in the presence of exogenous NETs for up to 48 h and assayed for NET degradation at the indicated timepoints.
Figure 8:

Study GR17-4 assessed the time-dependent NET-degrading capacity of GR-17 cells when cultured directly with exogenous NETs, which may better reflect conditions in the human lung with ARDS. The GR-17 cells or control MSCs were plated in a 96-well plate at 100,000 per well and in a 2-fold dilution series to 200 per well. 24 hours after plating, supernatants were removed and adherent GR-17 or control MSC monolayers were washed twice with tissue culture media. Either NETs induced from $10^5$ neutrophils in 100 ul of ExCellerate media or naked plasmid DNA (5 μg/100 μL culture) were added directly onto cultures and co-cultured for up to 48 hours. Supernatants were analyzed for presence of NETs using fluorescence microscopy with Sytox green (ThermoFisher) and double-stranded DNA using a Quant-iT™ dsDNA assay (high sensitivity; ThermoFisher) and fluorometry on a Cytation-5 plate reader (BioTek). GR-17 digested NETs over 2 days without loss in activity (FIG. 8). NET digestion was detectable as early as 2 h and increased to complete digestion at about 14 hours. It was concluded that GR-17 digests NETs in a time-dependent manner.

Figure 9:
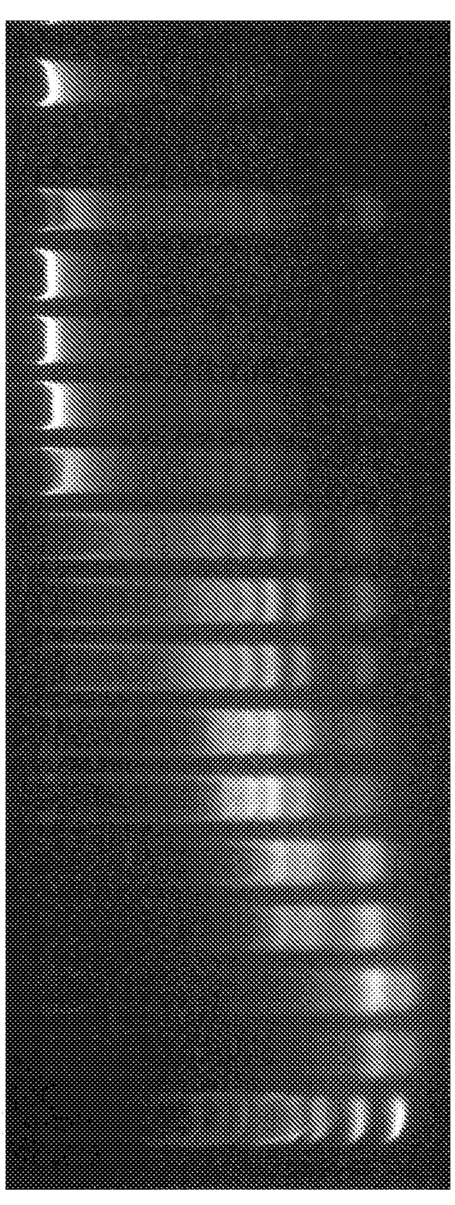
FIG. 9 shows the results of a chromatin degradation assay using DNA electrophoresis with various MSCs made according to a specific embodiment of the invention. MSCs were transfected with DNase1 mRNA or DNase1L3 mRNA and cultured. Between timepoints (e.g., day 0 to day 1 (D1)) supernatants were collected and used in chromatin digestion assays. Control MSCs were transfected with an irrelevant protein.

To confirm the specific activity of each enzyme, Study GR17-5 determined the capacity of DNASE1 or DNASE1L3 to digest chromatin over time. 10 million human MSCs were transfected with 1 μg of mRNA encoding either human DNASE1 or human DNASE1L3, cultured for 2 hours, frozen, stored overnight at −80° C., thawed, and cultured for up to 1 week. Supernatants were collected at the indicated timepoints (see FIG. 9) and their chromatin-digesting activity was assayed as described above. DNASE1 and DNASE1L3 were each capable of degrading chromatin and maintained activity for at least 3 days (FIG. 9). DNASE1 chromatin-digesting activity was detectable up to Day 7 while DNASE1L3 activity waned after about 3 days. Differential activity between DNASE1 and DNASE1L3 was consistent with differences mRNA and protein expression between these enzymes (see Study GR17-1). It was concluded that Human MSCs transfected with DNASE1 mRNA or DNASE1L3 mRNA can degrade chromatin for at least 3 days.

Figure 10:
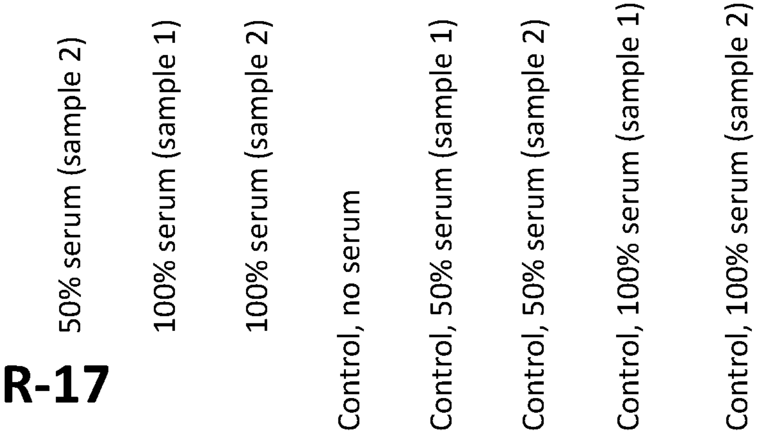
FIG. 10 shows the results of a chromatin degradation assay using DNA electrophoresis with MSCs made according to a specific embodiment of the invention, and in the presence of no serum, 50% serum, or 100% serum. GR-17 was frozen, thawed and incubated in the presence of NETs overnight in media supplemented with 0%, 50% or 100% fresh off-the-clot serum collected from healthy volunteers. Serum incubation was done in replicates.
Figure 10:

Study GR17-6 determined the capacity of GR-17 to degrade DNA and NETs in the presence of human serum. GR-17 was frozen, thawed, and incubated in the presence of NETs overnight ($0.1 \times 10^6$ cells/well) in media with 0%, 50% or 100% fresh off-the-clot serum collected from healthy volunteers. Serum incubation was done in replicates. GR-17 maintained its NET-degrading capacity in the presence of human serum (FIG. 10). The serum-alone exhibited NET-degradation. NET digestion was evident but incomplete in the presence of serum. GR-17 completely eliminated NETs even in the presence of 100% serum, indicating that serum does not inhibit the capacity of GR-17 to inhibit NETs. Results are representative of serum collected from three different healthy donors. It was concluded that Human serum does not interfere with GR-17's capacity to degrade NETs.

Therefore, GR-17 cells express mRNA and protein for DNASE1 and DNASE1L3. GR-17 shows potent activity to degrade cell-free naked DNA, chromatin (nuclei), and NETs in a time- and dose-dependent manner. GR-17 can degrade large (visible) amounts of NETs within 10 minutes.

Example 11: Production of Functional DNAse-Secreting NK Cells from an Inventive Combination of mRNA Constructs The following example is of human DNAse-secreting NK cells produced by introduction of an inventive combination of mRNA constructs that encode human DNASE1 and DNASE1L3.

Two separate mRNA constructs, corresponding respectively to SEQ ID NO: 1 (DNASE1) and SEQ ID NO: 2 (DNASE1L3), were generated by in vitro transcription. The in vitro transcription was performed by amplification of the double-stranded DNA template from DNA plasmids by PCR followed by in vitro transcription using T7 RNA polymerase. An additional polyadenine tail of about 100 adenine nucleotides was added enzymatically to each mRNA. A 7-methylguanosine cap was incorporated at the 5' end of each mRNA during the co-transcriptional RNA synthesis.

The first mRNA construct comprised, from 5' to 3': a 5' cap; a 5' UTR described as SEQ ID NO: 23; a Kozak sequence described in SEQ ID NO: 20; a sequence of SEQ ID NO:1; a 3' UTR described as SEQ ID NO: 24, and a 3' polyadenine tail of 180 adenine units or more.

The second mRNA construct comprised, from 5' to 3': a 5' cap; a 5' UTR described as SEQ ID NO: 23; a Kozak sequence described in SEQ ID NO: 20; a sequence of SEQ ID NO:2; a 3' UTR described as SEQ ID NO: 24, and a 3' polyadenine tail of 180 adenine units or more.

To prepare NK cells, NK cells were isolated from whole blood by isolation of peripheral blood monocytes (PBMC) by centrifuge gradient followed by CD56+ magnetic bead positive selection to obtain >98% pure NK cells that are >90% viable. These NK cells were expanded by incubation at 37° C. with 5% $CO_2$ in the presence of K562 feeder cells and supplemented with IL15 for 7 to 10 days. The cells are resuspended in transfection buffer and simultaneously transfected with a mixture of the two aforementioned mRNA constructs by electroporation (4D NUCLEOFECTOR®, Lonza) according to manufacturer's instructions. Cells are then returned to culture in a standard medium containing IL-15 for overnight incubation prior to analysis for viability and activity according to the methods described below.

NK cells obtained from the above-described process were tested for viability and NET-degrading capacity. Viability was determined by an automated cell counter (Auto2000, Nexcelom Biosciences) following staining with ViaStain™ (acridine orange and propidium iodide) according to the manufacturer's protocol. To test NET-degrading capacity of transfected NK cells, culture supernatants were first incubated with NETs generated from phorbol myristate acetate-activated human neutrophils. Neutrophils were isolated from whole anti-coagulated blood by density grade centrifugation. Recombinant human DNASE1 and DNASE1L3 were used as positive controls. The amount of NET DNA released was determined by addition of picogreen (Invitrogen), a DNA fluorescence dye, to the mixed culture and then quantified by fluorescence spectrometry.

NK cells transfected with the above-described constructs expressed and secreted functional DNASE1 and DNASE1L3 constitutively over the course of at least 24 hours.

Thus, NK cells can be transfected with the inventive combination of mRNA sequences to express and secrete functional DNASE1 and DNASE1L3 protein. The result of this process is inventive, DNase-secreting, NK cells that are useful for therapeutic administration, e.g., to a person affected by ARDS.

Example 12: Production of Functional DNAse-Secreting MSCs from an Inventive Combination of mRNA Constructs The following example is of human DNAse-secreting MSCs produced by introduction of an inventive combination of mRNA construct that encode human DNASE1 and DNASE1L3.

Two separate mRNA constructs, corresponding respectively to SEQ ID NO: 1 (DNASE1) and SEQ ID NO: 2 (DNASE1L3) were generated by in vitro transcription. The in vitro transcription was performed by amplification of the double-stranded DNA template from DNA plasmids by PCR with a 5' primer and a 3' primer that contains 180 additional thymidine nucleotides prior to the template-binding sequence. The PCR product was used for in vitro transcription using T7 RNA polymerase. An additional polyadenine tail of about 60 adenine nucleotides was added enzymatically to each mRNA. A 7-methylguanosine cap was incorporated at the 5' end of each mRNA during the co-transcriptional RNA synthesis.

The first mRNA construct comprised, from 5' to 3': a 5' cap; a 5' UTR described as SEQ ID NO: 23; a Kozak sequence described in SEQ ID NO: 20; a sequence of SEQ ID NO:1; a 3' UTR described as SEQ ID NO: 24, and a 3' polyadenine tail of 180 adenine units or more.

The second mRNA construct comprised, from 5' to 3': a 5' cap; a 5' UTR described as SEQ ID NO: 23; a Kozak sequence described in SEQ ID NO: 20; a sequence of SEQ ID NO:2; a 3' UTR described as SEQ ID NO: 24, and a 3' polyadenine tail of 180 adenine units or more.

To prepare MSCs from RNA constructs, MSCs isolated from human umbilical cord were purchased from ATCC, thawed and expanded in T75 flasks by culture at 37° C. with 5% $CO_2$ in $\alpha$-DMEM medium supplemented with 10% human serum. The cells were then passaged upon reaching 80% confluency. The cells were resuspended in P3 transfection buffer (Lonza) and simultaneously transfected with a mixture of the two aforementioned mRNA constructs by electroporation (4D NUCLEOFECTOR®, Lonza) according to manufacturer's instructions. Cells were then returned to culture in complete medium for overnight incubation, then frozen at −80° C. Transfected cells were thawed and incubated for another 7 days in the presence of complete medium and supernatant samples were collected and frozen at 4 h, 1 day, 2 days, 3 days, 5 days and 7 days after thaw. Thawed cells and supernatants were assayed for viability and activity according to the methods described below.

MSCs obtained from the above-described process were tested for viability, DNASE1 and DNASE1L3 expression, and DNA- and chromatin-degrading capacity. Viability was determined by flow cytometry on a GUAVA® EASYCYTE® 12HT Flow cytometer (EMD Millipore). To test viability, a sample of the MSCs was mixed with propidium iodide and run on the flow cytometer with electronic gating on fluorescence in the near infrared channel. To test expression of DNASE1 and DNASE1L3, commercially available DNASE1 and DNASE1L3 kits (i.e., Abbexa) were used to assay supernatants of cultured MSCs according the manufacturers' instructions. To test DNA degrading capacity of transfected MSCs, culture supernatants were tested with a fluorometric DNASE1 assay kit (i.e., AbCam) according to the manufacturer's instructions. To test chromatin degrading capacity of transfected MSCs, culture supernatants were first incubated with NETs generated from phorbol myristate acetate—activated human neutrophils. Neutrophils were isolated from fresh apheresis product by density grade centrifugation. Recombinant human DNASE1 and DNASE1L3 were used as positive controls. The amount of NET DNA released was determined by adding picogreen (Invitrogen), a DNA fluorescence dye, to the mixed culture and then quantified by fluorescence spectrometry.

The MSCs transfected with the above-described constructs express and secrete functional DNASE1 and DNASE1L3 constitutively over the course of at least 24 hours. MSCs maintain the capacity to express and secrete functional DNASE1 and DNASE1L3 following freeze/thaw.

Thus, MSCs can be transfected with the inventive combination of mRNA sequences to express and secrete functional DNASE1 and DNASE1L3 protein. The result of this process is inventive, i.e., DNase-secreting MSCs that are useful for therapeutic administration, e.g., to a person affected by ARDS.

Example 13: In Vivo Safety and Efficacy of Functional DNAse-Secreting MSCs in a Mouse Model of ALI DNAse-secreting MSCs produced from inventive RNA constructs comprising the nucleotide sequences of SEQ ID NO: 1 and SEQ ID NO: 2, were tested in an Acute Lung Injury (ALI) animal model of ARDS. In this model, ALI was first induced by intratracheal administration of lipopolysaccharide (LPS), and MSCs were then administered by intravenous injection.

DNAse-secreting MSCs were prepared by transfection of the inventive RNA constructs, as discussed in Example 12. 8-12 week old C57BL/6 mice were anesthetized and administered 2 mg/kg of LPS solution by an intratracheal administration. At 12 hours after LPS administration, mice were randomized to receive intravenous vehicle only (negative control), $1.5\times10^6$ untransfected MSCs (negative control), or $0.25\times10^6$ or $1\times10^6$ DNAse-secreting MSCs. 4 to 7 animals were assigned to each group.

24 hours after MSC administration, 3 mice from each group were anesthetized and bronchoalveolar lavage fluid (BALF) was collected with 1 mL phosphate buffered saline (PBS) solution. Mice were then sacrificed; blood and lung tissues collected.

Total cell number and infiltration of specific cell types (i.e., macrophages, neutrophils and lymphocytes) in BALF were analyzed with flow cytometry on a Guava EasyCyte HT flow cytometer (Luminex). Nucleated cells were identified by Forward and Side scatter properties and concentrations were determined by comparison with known numbers of counting beads using 123count eBeads (Invitrogen). The remaining sample was used for cell-free DNA measurement and detection of NET-specific markers in sandwich ELISA assays, specifically Myeloperoxisdase (MPO)-DNA complexes, neutrophil elastase (NE), and citrullinated histone (CitH3).

Serum was collected from whole blood and frozen down for subsequent analysis of NET-specific markers in sandwich ELISA assays similar to BALF.

Lungs were harvested, the left lungs were flashed frozen, and the right lungs were fixed and fixed in 4% formalin solution for subsequent pathologic analysis.

5 days after LPS administration, the remaining mice were sacrificed, blood and lung tissue was collected and processed as above.

All animals tolerated treatment and recovered following a transient ALI between Days 1 and 3 with the exception of one mouse that died prior to randomization and treatment on Day 1. There were no differences between the two Descartes-30 groups and control animals with respect to clinical observations, daily weights, organ weights, and overall survival.

Example 14: Production of Functional DNAse-Secreting MSCs from an Inventive Combination of mRNA Constructs with or without Pseudouridine The following example is of human DNAse-secreting MSCs produced by introduction of an inventive combination of mRNA construct that encode human DNASE1 and DNASE1L3, where such mRNAs are enriched or not enriched in pseudouridine.

MSCs were prepared and tested according to the methods Example 12 above, from mRNAs that were wild-type (U) with respect to uridine, or for which the uridine positions were substantially substituted with pseudouridine (ψ).

Figure 11:
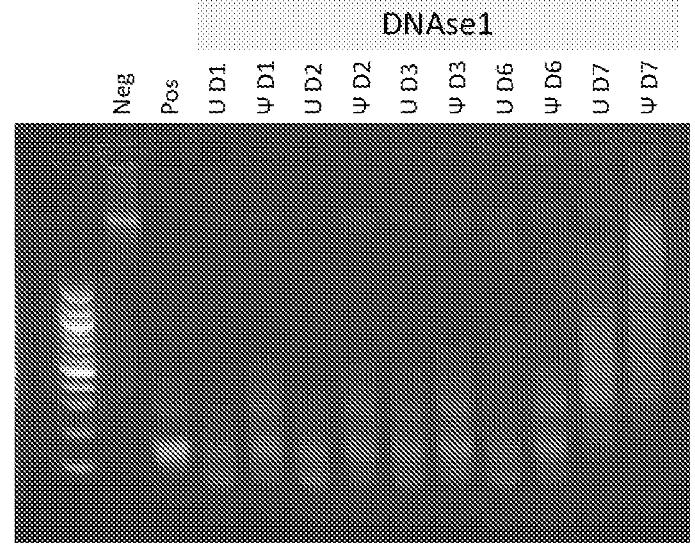
FIG. 11 shows the results of a chromatin degradation assay using DNA electrophoresis with MSCs made according to a specific embodiment of the invention. MSCs were transfected with wild-type (U) or pseudouridine (ψ) DNase1 or DNase1L3 mRNA and cultured as described. Between timepoints, e.g., day 0 to day 1 (D1), supernatants were collected and used in chromatin digestion assays.
Figure 11:
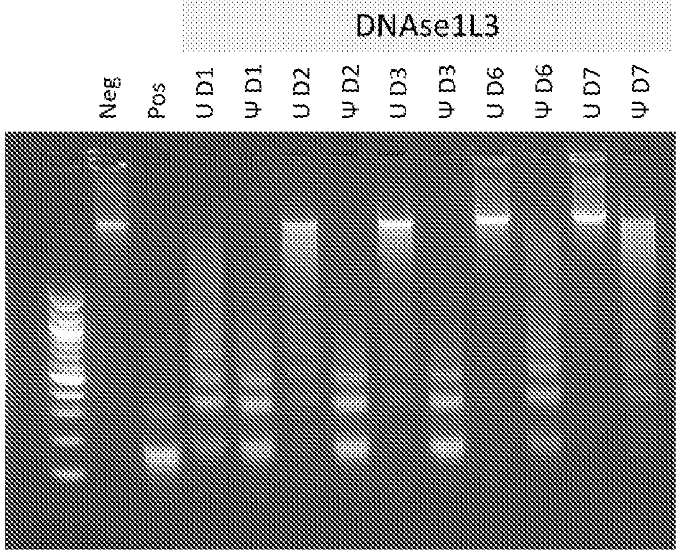

FIG. 11 shows the results of a chromatin degradation assay with MSCs transfected with wild-type (U) or pseudouridine (ψ) DNase1 or DNase1L3 mRNA and cultured as described. Between timepoints, e.g., day 0 to day 1 (D1), supernatants were collected and used in chromatin digestion assays.

Supernatants from MSC transfected with DNase1L3 mRNA consistently resulted in greater chromatin digestion, signifying higher production of DNase1L3, when the mRNA was encoded using pseudouridine rather than uridine. However, modification of the DNase1 rRNA with pseudouridine did not increase its level of activity.

Thus, substitution of pseudouridine for uridine in mRNA encoding DNase1L3 significantly improved chromatin digestion, whereas substitution of pseudouridine for uridine in mRNA encoding DNase1 did not improve chromatin digestion.

EQUIVALENTS AND SCOPE

Those skilled in the art will recognize or be able to ascertain using no more than routine experimentation, many equivalents of the embodiments described herein. The scope of the present disclosure is not intended to be limited to the above description, but rather is as set forth in the appended claims.

Articles such as “a,” “an,” and “the” may mean one or more than one unless indicated to the contrary or otherwise evident from the context. Claims, embodiments, or descriptions that include “or” between two or more members of a group are considered satisfied if one, more than one, or all of the group members are present, unless indicated to the contrary or otherwise evident from the context. The disclosure of a group that includes “or” between two or more group members provides embodiments in which exactly one member of the group is present, embodiments in which two or more members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term “comprising” is intended to be open and permits the inclusion of additional elements or steps. It should be understood that, in general, where an Claim, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular Claim of the present invention may be explicitly excluded from any one or more of the claims. Where ranges are given, any value within the range may explicitly be excluded from any one or more of the claims. Any Claim, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. An isolated mammalian cell modified to express:

at least one DNAse enzyme; and at least one anti-B-cell maturation antigen (BCMA) antibody.

2. The cell of claim 1, wherein the cell is a mesenchymal stem cell.

3. The cell of claim 1, wherein the cell is a T cell.

4. The cell of claim 3, wherein the cell is a cluster of differentiation 8 (CD8+) cell.

5. The cell of claim 1, wherein the anti-BCMA antibody is a monoclonal antibody that binds BCMA.

6. The cell of claim 1, wherein the at least one DNAse enzyme and the at least one anti-BCMA antibody are expressed from one or more mRNAs.

7. The cell of claim 6, wherein the mRNA was introduced into the cell by electroporation.

8. The cell of claim 1, wherein the cell is a human cell.

9. The cell of claim 1, wherein the cell is a cluster of differentiation 4 (CD4+) cell.

10. The cell of claim 1, wherein the anti-BCMA antibody is a monoclonal, bispecific, dual-specific, or multi-specific antibody that binds BCMA.

11. The cell of claim 1, wherein the anti-BCMA antibody is a bispecific T-cell engager.

12. The cell of claim 1, wherein the at least one DNAse enzyme comprises DNASE1 and/or DNASE1L3.

13. The cell of claim 1, wherein the at least one DNAse enzyme comprises the amino acid sequence of any one of SEQ ID NOs: 1-3.

14. The cell of claim 1, wherein the anti-BCMA antibody is a bispecific antibody that comprises the amino acid sequence of SEQ ID NO: 22.

15. A cell therapy product composition comprising a plurality of cells comprising the cell of claim 1.

* * * * *

SEQUENCE LISTING

```
<160> NUMBER OF SEQ ID NOS: 28

<210> SEQ ID NO 1
<211> LENGTH: 282
<212> TYPE: PRT
<213> ORGANISM: Artificial Sequence
<220> FEATURE:
<223> OTHER INFORMATION: Synthetic

<400> SEQUENCE: 1
```

```
Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
        275                 280
```

<210> SEQ ID NO 2
<211> LENGTH: 305
<212> TYPE: PRT
<213> ORGANISM: Artificial Sequence
<220> FEATURE:
<223> OTHER INFORMATION: Synthetic

<400> SEQUENCE: 2

```
Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80
```

```
Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
    290                 295                 300

Ser
305


<210> SEQ ID NO 3
<211> LENGTH: 605
<212> TYPE: PRT
<213> ORGANISM: Artificial Sequence
<220> FEATURE:
<223> OTHER INFORMATION: Synthetic

<400> SEQUENCE: 3

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125
```

```
Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys Glu Gly Arg Gly Ser Leu
        275                 280                 285

Leu Thr Cys Gly Asp Val Glu Glu Asn Pro Gly Pro Met Ser Arg Glu
    290                 295                 300

Leu Ala Pro Leu Leu Leu Leu Leu Leu Ser Ile His Ser Ala Leu Ala
305                 310                 315                 320

Met Arg Ile Cys Ser Phe Asn Val Arg Ser Phe Gly Glu Ser Lys Gln
                325                 330                 335

Glu Asp Lys Asn Ala Met Asp Val Ile Val Lys Val Ile Lys Arg Cys
            340                 345                 350

Asp Ile Ile Leu Val Met Glu Ile Lys Asp Ser Asn Asn Arg Ile Cys
        355                 360                 365

Pro Ile Leu Met Glu Lys Leu Asn Arg Asn Ser Arg Arg Gly Ile Thr
    370                 375                 380

Tyr Asn Tyr Val Ile Ser Ser Arg Leu Gly Arg Asn Thr Tyr Lys Glu
385                 390                 395                 400

Gln Tyr Ala Phe Leu Tyr Lys Glu Lys Leu Val Ser Val Lys Arg Ser
                405                 410                 415

Tyr His Tyr His Asp Tyr Gln Asp Gly Asp Ala Asp Val Phe Ser Arg
            420                 425                 430

Glu Pro Phe Val Val Trp Phe Gln Ser Pro His Thr Ala Val Lys Asp
        435                 440                 445

Phe Val Ile Ile Pro Leu His Thr Thr Pro Glu Thr Ser Val Lys Glu
    450                 455                 460

Ile Asp Glu Leu Val Glu Val Tyr Thr Asp Val Lys His Arg Trp Lys
465                 470                 475                 480

Ala Glu Asn Phe Ile Phe Met Gly Asp Phe Asn Ala Gly Cys Ser Tyr
                485                 490                 495

Val Pro Lys Lys Ala Trp Lys Asn Ile Arg Leu Arg Thr Asp Pro Arg
            500                 505                 510

Phe Val Trp Leu Ile Gly Asp Gln Glu Asp Thr Thr Val Lys Lys Ser
        515                 520                 525

Thr Asn Cys Ala Tyr Asp Arg Ile Val Leu Arg Gly Gln Glu Ile Val
    530                 535                 540
```

```
Ser Ser Val Val Pro Lys Ser Asn Ser Val Phe Asp Phe Gln Lys Ala
545                 550                 555                 560

Tyr Lys Leu Thr Glu Glu Glu Ala Leu Asp Val Ser Asp His Phe Pro
                565                 570                 575

Val Glu Phe Lys Leu Gln Ser Ser Arg Ala Phe Thr Asn Ser Lys Lys
            580                 585                 590

Ser Val Thr Leu Arg Lys Lys Thr Lys Ser Lys Arg Ser
        595                 600                 605


<210> SEQ ID NO 4
<211> LENGTH: 229
<212> TYPE: PRT
<213> ORGANISM: Artificial Sequence
<220> FEATURE:
<223> OTHER INFORMATION: Synthetic

<400> SEQUENCE: 4

Met Ala Leu Pro Val Thr Ala Leu Leu Leu Pro Leu Ala Leu Leu Leu
1               5                   10                  15

His Ala Ala Arg Pro Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser Phe Val Pro Val Phe Leu Pro Ala Lys
    130                 135                 140

Pro Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
        195                 200                 205

Val Ile Thr Leu Tyr Cys Asn His Arg Asn Gly Gly Ser Asp Tyr Lys
    210                 215                 220

Asp Asp Asp Asp Lys
225


<210> SEQ ID NO 5
<211> LENGTH: 519
<212> TYPE: PRT
<213> ORGANISM: Artificial Sequence
<220> FEATURE:
<223> OTHER INFORMATION: Synthetic

<400> SEQUENCE: 5

Met Gly Trp Ser Cys Ile Ile Leu Phe Leu Val Ala Thr Ala Thr Gly
1               5                   10                  15
```

```
Val His Ser Asp Tyr Lys Asp Asp Asp Asp Lys Thr Ile Pro Pro His
            20                  25                  30

Val Gln Lys Ser Val Asn Asn Asp Met Ile Val Thr Asp Asn Asn Gly
        35                  40                  45

Ala Val Lys Phe Pro Gln Leu Cys Lys Phe Cys Asp Val Arg Phe Ser
    50                  55                  60

Thr Cys Asp Asn Gln Lys Ser Cys Met Ser Asn Cys Ser Ile Thr Ser
65                  70                  75                  80

Ile Cys Glu Lys Pro Gln Glu Val Cys Val Ala Val Trp Arg Lys Asn
                85                  90                  95

Asp Glu Asn Ile Thr Leu Glu Thr Val Cys His Asp Pro Lys Leu Pro
            100                 105                 110

Tyr His Asp Phe Ile Leu Glu Asp Ala Ala Ser Pro Lys Cys Ile Met
        115                 120                 125

Lys Glu Lys Lys Lys Pro Gly Glu Thr Phe Phe Met Cys Ser Cys Ser
    130                 135                 140

Ser Asp Glu Cys Asn Asp Asn Ile Ile Phe Ser Glu Glu Tyr Asn Thr
145                 150                 155                 160

Ser Asn Pro Asp Thr Ile Pro Pro His Val Gln Lys Ser Val Asn Asn
                165                 170                 175

Asp Met Ile Val Thr Asp Asn Asn Gly Ala Val Lys Phe Pro Gln Leu
            180                 185                 190

Cys Lys Phe Cys Asp Val Arg Phe Ser Thr Cys Asp Asn Gln Lys Ser
        195                 200                 205

Cys Met Ser Asn Cys Ser Ile Thr Ser Ile Cys Glu Lys Pro Gln Glu
    210                 215                 220

Val Cys Val Ala Val Trp Arg Lys Asn Asp Glu Asn Ile Thr Leu Glu
225                 230                 235                 240

Thr Val Cys His Asp Pro Lys Leu Pro Tyr His Asp Phe Ile Leu Glu
                245                 250                 255

Asp Ala Ala Ser Pro Lys Cys Ile Met Lys Glu Lys Lys Lys Pro Gly
            260                 265                 270

Glu Thr Phe Phe Met Cys Ser Cys Ser Ser Asp Glu Cys Asn Asp Asn
        275                 280                 285

Ile Ile Phe Ser Glu Glu Tyr Asn Thr Ser Asn Pro Asp Gly Thr Gly
    290                 295                 300

Gly Ser Ser Gly Ile Thr Cys Pro Pro Pro Met Ser Val Glu His Ala
305                 310                 315                 320

Asp Ile Trp Val Lys Ser Tyr Ser Leu Tyr Ser Arg Glu Arg Tyr Ile
                325                 330                 335

Cys Asn Ser Gly Phe Lys Arg Lys Ala Gly Thr Ser Ser Leu Thr Glu
            340                 345                 350

Cys Val Leu Asn Lys Ala Thr Asn Val Ala His Trp Thr Thr Pro Ser
        355                 360                 365

Leu Lys Cys Ile Arg Asp Pro Ala Leu Val His Gln Arg Pro Ala Pro
    370                 375                 380

Pro Ser Gly Gly Ser Gly Gly Gly Gly Ser Gly Gly Gly Ser Gly Gly
385                 390                 395                 400

Gly Gly Ser Leu Gln Asn Trp Val Asn Val Ile Ser Asp Leu Lys Lys
                405                 410                 415

Ile Glu Asp Leu Ile Gln Ser Met His Ile Asp Ala Thr Leu Tyr Thr
            420                 425                 430
```

```
Glu Ser Asp Val His Pro Ser Cys Lys Val Thr Ala Met Lys Cys Phe
        435                 440                 445

Leu Leu Glu Leu Gln Val Ile Ser Leu Glu Ser Gly Asp Ala Ser Ile
    450                 455                 460

His Asp Thr Val Glu Asn Leu Ile Ile Leu Ala Asn Asn Ser Leu Ser
465                 470                 475                 480

Ser Asn Gly Asn Val Thr Glu Ser Gly Cys Lys Glu Cys Glu Glu Leu
                485                 490                 495

Glu Glu Lys Asn Ile Lys Glu Phe Leu Gln Ser Phe Val His Ile Val
            500                 505                 510

Gln Met Phe Ile Asn Thr Ser
        515


<210> SEQ ID NO 6
<211> LENGTH: 519
<212> TYPE: PRT
<213> ORGANISM: Artificial Sequence
<220> FEATURE:
<223> OTHER INFORMATION: Synthetic

<400> SEQUENCE: 6

Met Gly Trp Ser Cys Ile Ile Leu Phe Leu Val Ala Thr Ala Thr Gly
1               5                   10                  15

Val His Ser Asp Tyr Lys Asp Asp Asp Asp Lys Asn Trp Val Asn Val
            20                  25                  30

Ile Ser Asp Leu Lys Lys Ile Glu Asp Leu Ile Gln Ser Met His Ile
        35                  40                  45

Asp Ala Thr Leu Tyr Thr Glu Ser Asp Val His Pro Ser Cys Lys Val
    50                  55                  60

Thr Ala Met Lys Cys Phe Leu Leu Glu Leu Gln Val Ile Ser Leu Glu
65                  70                  75                  80

Ser Gly Asp Ala Ser Ile His Asp Thr Val Glu Asn Leu Ile Ile Leu
                85                  90                  95

Ala Asn Asn Ser Leu Ser Ser Asn Gly Asn Val Thr Glu Ser Gly Cys
            100                 105                 110

Lys Glu Cys Glu Glu Leu Glu Glu Lys Asn Ile Lys Glu Phe Leu Gln
        115                 120                 125

Ser Phe Val His Ile Val Gln Met Phe Ile Asn Thr Ser Gly Thr Gly
    130                 135                 140

Gly Ser Ser Gly Ile Thr Cys Pro Pro Pro Met Ser Val Glu His Ala
145                 150                 155                 160

Asp Ile Trp Val Lys Ser Tyr Ser Leu Tyr Ser Arg Glu Arg Tyr Ile
                165                 170                 175

Cys Asn Ser Gly Phe Lys Arg Lys Ala Gly Thr Ser Ser Leu Thr Glu
            180                 185                 190

Cys Val Leu Asn Lys Ala Thr Asn Val Ala His Trp Thr Thr Pro Ser
        195                 200                 205

Leu Lys Cys Ile Arg Asp Pro Ala Leu Val His Gln Arg Pro Ala Pro
    210                 215                 220

Pro Ser Gly Gly Ser Gly Gly Gly Gly Ser Gly Gly Gly Ser Gly Gly
225                 230                 235                 240

Gly Gly Ser Leu Gln Thr Ile Pro Pro His Val Gln Lys Ser Val Asn
                245                 250                 255

Asn Asp Met Ile Val Thr Asp Asn Asn Gly Ala Val Lys Phe Pro Gln
            260                 265                 270
```

```
Leu Cys Lys Phe Cys Asp Val Arg Phe Ser Thr Cys Asp Asn Gln Lys
        275                 280                 285

Ser Cys Met Ser Asn Cys Ser Ile Thr Ser Ile Cys Glu Lys Pro Gln
    290                 295                 300

Glu Val Cys Val Ala Val Trp Arg Lys Asn Asp Glu Asn Ile Thr Leu
305                 310                 315                 320

Glu Thr Val Cys His Asp Pro Lys Leu Pro Tyr His Asp Phe Ile Leu
                325                 330                 335

Glu Asp Ala Ala Ser Pro Lys Cys Ile Met Lys Glu Lys Lys Lys Pro
            340                 345                 350

Gly Glu Thr Phe Phe Met Cys Ser Cys Ser Ser Asp Glu Cys Asn Asp
        355                 360                 365

Asn Ile Ile Phe Ser Glu Glu Tyr Asn Thr Ser Asn Pro Asp Thr Ile
    370                 375                 380

Pro Pro His Val Gln Lys Ser Val Asn Asn Asp Met Ile Val Thr Asp
385                 390                 395                 400

Asn Asn Gly Ala Val Lys Phe Pro Gln Leu Cys Lys Phe Cys Asp Val
                405                 410                 415

Arg Phe Ser Thr Cys Asp Asn Gln Lys Ser Cys Met Ser Asn Cys Ser
            420                 425                 430

Ile Thr Ser Ile Cys Glu Lys Pro Gln Glu Val Cys Val Ala Val Trp
        435                 440                 445

Arg Lys Asn Asp Glu Asn Ile Thr Leu Glu Thr Val Cys His Asp Pro
    450                 455                 460

Lys Leu Pro Tyr His Asp Phe Ile Leu Glu Asp Ala Ala Ser Pro Lys
465                 470                 475                 480

Cys Ile Met Lys Glu Lys Lys Lys Pro Gly Glu Thr Phe Phe Met Cys
                485                 490                 495

Ser Cys Ser Ser Asp Glu Cys Asn Asp Asn Ile Ile Phe Ser Glu Glu
            500                 505                 510

Tyr Asn Thr Ser Asn Pro Asp
        515


<210> SEQ ID NO 7
<211> LENGTH: 230
<212> TYPE: PRT
<213> ORGANISM: Artificial Sequence
<220> FEATURE:
<223> OTHER INFORMATION: Synthetic

<400> SEQUENCE: 7

Met Asp Ser Asn Thr Val Ser Ser Phe Gln Val Asp Cys Phe Leu Trp
1               5                   10                  15

His Val Arg Lys Gln Val Ala Asp Gln Glu Leu Gly Asp Ala Pro Phe
            20                  25                  30

Leu Asp Arg Leu Arg Arg Asp Gln Lys Ser Leu Lys Gly Arg Gly Ser
        35                  40                  45

Thr Leu Gly Leu Asn Ile Glu Thr Ala Thr Cys Val Gly Lys Gln Ile
    50                  55                  60

Val Glu Arg Ile Leu Lys Glu Glu Ser Asp Glu Ala Phe Arg Met Thr
65                  70                  75                  80

Met Ala Ser Ala Leu Ala Ser Arg Tyr Leu Thr Asp Met Thr Ile Glu
                85                  90                  95

Glu Met Ser Arg Asp Trp Phe Met Leu Met Pro Lys Gln Lys Val Ala
            100                 105                 110
```

```
Gly Pro Leu Cys Val Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Thr Leu Leu Arg Ala Phe Thr Glu Glu Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Gly Pro Pro Leu Thr Pro Thr Gln Lys Arg Lys Met Ala Gly
    210                 215                 220

Lys Ile Arg Ser Glu Val
225                 230


<210> SEQ ID NO 8
<211> LENGTH: 190
<212> TYPE: PRT
<213> ORGANISM: Artificial Sequence
<220> FEATURE:
<223> OTHER INFORMATION: Synthetic

<400> SEQUENCE: 8

Met Ser Lys Ile Tyr Ile Asp Glu Arg Ser Asp Ala Glu Ile Val Cys
1               5                   10                  15

Ala Ala Ile Lys Asn Ile Gly Ile Glu Gly Ala Thr Ala Ala Gln Leu
            20                  25                  30

Thr Arg Gln Leu Asn Met Glu Lys Arg Glu Val Asn Lys Ala Leu Tyr
        35                  40                  45

Asp Leu Gln Arg Ser Ala Met Val Tyr Ser Ser Asp Asp Ile Pro Pro
    50                  55                  60

Arg Trp Phe Met Thr Thr Glu Ala Asp Lys Pro Asp Ala Asp Ala Met
65                  70                  75                  80

Ala Asp Val Ile Ile Asp Asp Val Ser Arg Glu Lys Ser Met Arg Glu
                85                  90                  95

Asp His Lys Ser Phe Asp Asp Val Ile Pro Ala Lys Lys Ile Ile Asp
            100                 105                 110

Trp Lys Asp Ala Asn Pro Val Thr Ile Ile Asn Glu Tyr Cys Gln Ile
        115                 120                 125

Thr Lys Arg Asp Trp Ser Phe Arg Ile Glu Ser Val Gly Pro Ser Asn
    130                 135                 140

Ser Pro Thr Phe Tyr Ala Cys Val Asp Ile Asp Gly Arg Val Phe Asp
145                 150                 155                 160

Lys Ala Asp Gly Lys Ser Lys Arg Asp Ala Lys Asn Asn Ala Ala Lys
                165                 170                 175

Leu Ala Val Asp Lys Leu Leu Gly Tyr Val Ile Ile Arg Phe
            180                 185                 190


<210> SEQ ID NO 9
<211> LENGTH: 376
<212> TYPE: PRT
<213> ORGANISM: Artificial Sequence
<220> FEATURE:
<223> OTHER INFORMATION: Synthetic

<400> SEQUENCE: 9
```

```
Met Val Val Val Ala Ala Ala Pro Asn Pro Ala Asp Gly Thr Pro Lys
1               5                   10                  15

Val Leu Leu Leu Ser Gly Gln Pro Ala Ser Ala Ala Gly Ala Pro Ala
            20                  25                  30

Gly Gln Ala Leu Pro Leu Met Val Pro Ala Gln Arg Gly Ala Ser Pro
        35                  40                  45

Glu Ala Ala Ser Gly Gly Leu Pro Gln Ala Arg Lys Arg Gln Arg Leu
    50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
            100                 105                 110

Leu Leu Glu Asn Gln Leu Leu Arg Glu Lys Thr His Gly Leu Val Val
        115                 120                 125

Glu Asn Gln Glu Leu Arg Gln Arg Leu Gly Met Asp Ala Leu Val Ala
    130                 135                 140

Glu Glu Glu Ala Glu Ala Lys Gly Asn Glu Val Arg Pro Val Ala Gly
145                 150                 155                 160

Ser Ala Glu Ser Ala Ala Gly Ala Gly Pro Val Val Thr Pro Pro Glu
                165                 170                 175

His Leu Pro Met Asp Ser Gly Gly Ile Asp Ser Ser Asp Ser Glu Ser
            180                 185                 190

Asp Ile Leu Leu Gly Ile Leu Asp Asn Leu Asp Pro Val Met Phe Phe
        195                 200                 205

Lys Cys Pro Ser Pro Glu Pro Ala Ser Leu Glu Glu Leu Pro Glu Val
    210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255

Asp His Ile Tyr Thr Lys Pro Leu Val Leu Glu Ile Pro Ser Glu Thr
            260                 265                 270

Glu Ser Gln Ala Asn Val Val Val Lys Ile Glu Glu Ala Pro Leu Ser
        275                 280                 285

Pro Ser Glu Asn Asp His Pro Glu Phe Ile Val Ser Val Lys Glu Glu
    290                 295                 300

Pro Val Glu Asp Asp Leu Val Pro Glu Leu Gly Ile Ser Asn Leu Leu
305                 310                 315                 320

Ser Ser Ser His Cys Pro Lys Pro Ser Ser Cys Leu Leu Asp Ala Tyr
                325                 330                 335

Ser Asp Cys Gly Tyr Gly Gly Ser Leu Ser Pro Phe Ser Asp Met Ser
            340                 345                 350

Ser Leu Leu Gly Val Asn His Ser Trp Glu Asp Thr Phe Ala Asn Glu
        355                 360                 365

Leu Phe Pro Gln Leu Ile Ser Val
    370                 375
```

<210> SEQ ID NO 10
<211> LENGTH: 71
<212> TYPE: PRT
<213> ORGANISM: Artificial Sequence
<220> FEATURE:

```
<223> OTHER INFORMATION: Synthetic

<400> SEQUENCE: 10

Met Gly Gly Arg Arg Arg Lys Lys Arg Thr Asn Asp Thr Lys His Val
1               5                   10                  15

Arg Phe Ala Ala Ala Val Glu Val Trp Glu Ala Asp Asp Ile Glu Arg
            20                  25                  30

Lys Gly Pro Trp Glu Gln Val Ala Val Asp Arg Phe Arg Phe Gln Arg
        35                  40                  45

Arg Ile Ala Ser Val Glu Glu Leu Leu Ser Thr Val Leu Leu Arg Gln
    50                  55                  60

Lys Lys Leu Leu Glu Gln Gln
65                  70


<210> SEQ ID NO 11
<211> LENGTH: 370
<212> TYPE: PRT
<213> ORGANISM: Artificial Sequence
<220> FEATURE:
<223> OTHER INFORMATION: Synthetic

<400> SEQUENCE: 11

Met Ser Asp Ser Glu Lys Leu Asn Leu Asp Ser Ile Ile Gly Arg Leu
1               5                   10                  15

Leu Glu Val Gln Gly Ser Arg Pro Gly Lys Asn Val Gln Leu Thr Glu
            20                  25                  30

Asn Glu Ile Arg Gly Leu Cys Leu Lys Ser Arg Glu Ile Phe Leu Ser
        35                  40                  45

Gln Pro Ile Leu Leu Glu Leu Glu Ala Pro Leu Lys Ile Cys Gly Asp
    50                  55                  60

Ile His Gly Gln Tyr Tyr Asp Leu Leu Arg Leu Phe Glu Tyr Gly Gly
65                  70                  75                  80

Phe Pro Pro Glu Ser Asn Tyr Leu Phe Leu Gly Asp Tyr Val Asp Arg
                85                  90                  95

Gly Lys Gln Ser Leu Glu Thr Ile Cys Leu Leu Leu Ala Tyr Lys Ile
            100                 105                 110

Lys Tyr Pro Glu Asn Phe Phe Leu Leu Arg Gly Asn His Glu Cys Ala
        115                 120                 125

Ser Ile Asn Arg Ile Tyr Gly Phe Tyr Asp Glu Cys Lys Arg Arg Tyr
    130                 135                 140

Asn Ile Lys Leu Trp Lys Thr Phe Thr Asp Cys Phe Asn Cys Leu Pro
145                 150                 155                 160

Ile Ala Ala Ile Val Asp Glu Lys Ile Phe Cys Cys His Gly Gly Leu
                165                 170                 175

Ser Pro Asp Leu Gln Ser Met Glu Gln Ile Arg Arg Ile Met Arg Pro
            180                 185                 190

Thr Asp Val Pro Asp Gln Gly Leu Leu Cys Asp Leu Leu Trp Ser Asp
        195                 200                 205

Pro Asp Lys Asp Val Gln Gly Trp Gly Glu Asn Asp Arg Gly Val Ser
    210                 215                 220

Phe Thr Phe Gly Ala Glu Val Val Ala Lys Phe Leu His Lys His Asp
225                 230                 235                 240

Asp Leu Ile Cys Arg Ala His Gln Val Val Glu Asp Gly Tyr Glu Phe
                245                 250                 255

Phe Ala Lys Arg Gln Leu Val Thr Leu Phe Ser Ala Pro Asn Tyr Cys
            260                 265                 270
```

```
Gly Glu Phe Asp Asn Ala Gly Ala Met Met Ser Val Asp Glu Thr Leu
        275                 280                 285

Met Cys Ser Phe Gln Ile Leu Lys Pro Ala Asp Lys Asn Lys Gly Lys
    290                 295                 300

Tyr Gly Gln Phe Ser Gly Leu Asn Pro Gly Gly Arg Pro Ile Thr Pro
305                 310                 315                 320

Pro Arg Asn Ser Ala Lys Ala Lys Lys Ala Arg Gln Gly Pro Trp Glu
                325                 330                 335

Gln Leu Ala Arg Asp Arg Ser Arg Phe Ala Arg Arg Ile Thr Gln Ala
            340                 345                 350

Gln Glu Glu Leu Ser Pro Cys Leu Thr Pro Ala Ala Arg Ala Arg Ala
        355                 360                 365

Trp Ala
    370


<210> SEQ ID NO 12
<211> LENGTH: 352
<212> TYPE: PRT
<213> ORGANISM: Artificial Sequence
<220> FEATURE:
<223> OTHER INFORMATION: Synthetic

<400> SEQUENCE: 12

Met Gly Thr Met Lys Met Met Val His Ile Tyr Phe Val Ser Leu Leu
1               5                   10                  15

Leu Leu Leu Phe His Ser Tyr Ala Ile Asp Ile Glu Asn Glu Ile Thr
            20                  25                  30

Glu Phe Phe Asn Lys Met Arg Asp Thr Leu Pro Ala Lys Asp Ser Lys
        35                  40                  45

Trp Leu Asn Pro Ala Cys Met Phe Gly Gly Thr Met Asn Asp Ile Ala
    50                  55                  60

Ala Leu Gly Glu Pro Phe Ser Ala Lys Cys Pro Pro Ile Glu Asp Ser
65                  70                  75                  80

Leu Leu Ser His Arg Tyr Lys Asp Tyr Val Val Lys Trp Glu Arg Leu
                85                  90                  95

Glu Lys Asn Arg Arg Arg Gln Val Ser Asn Lys Arg Val Lys His Gly
            100                 105                 110

Asp Leu Trp Ile Ala Asn Tyr Thr Ser Lys Phe Ser Asn Arg Arg Tyr
        115                 120                 125

Leu Cys Thr Val Thr Thr Lys Asn Gly Asp Cys Val Gln Gly Ile Val
    130                 135                 140

Arg Ser His Ile Arg Lys Pro Pro Ser Cys Ile Pro Lys Thr Tyr Glu
145                 150                 155                 160

Leu Gly Thr His Asp Lys Tyr Gly Ile Asp Leu Tyr Cys Gly Ile Leu
                165                 170                 175

Tyr Ala Lys His Tyr Asn Asn Ile Thr Trp Tyr Lys Asp Asn Lys Glu
            180                 185                 190

Ile Asn Ile Asp Asp Ile Lys Tyr Ser Gln Thr Gly Lys Glu Leu Ile
        195                 200                 205

Ile His Asn Pro Glu Leu Glu Asp Ser Gly Arg Tyr Asp Cys Tyr Val
    210                 215                 220

His Tyr Asp Asp Val Arg Ile Lys Asn Asp Ile Val Val Ser Arg Cys
225                 230                 235                 240

Lys Ile Leu Thr Val Ile Pro Ser Gln Asp His Arg Phe Lys Leu Ile
                245                 250                 255
```

```
Leu Asp Pro Lys Ile Asn Val Thr Ile Gly Glu Pro Ala Asn Ile Thr
            260                 265                 270

Cys Thr Ala Val Ser Thr Ser Leu Leu Ile Asp Asp Val Leu Ile Glu
        275                 280                 285

Trp Glu Asn Pro Ser Gly Trp Leu Ile Gly Phe Asp Phe Asp Val Tyr
    290                 295                 300

Ser Val Leu Thr Ser Arg Gly Gly Ile Thr Glu Ala Thr Leu Tyr Phe
305                 310                 315                 320

Glu Asn Val Thr Glu Glu Tyr Ile Gly Asn Thr Tyr Lys Cys Arg Gly
                325                 330                 335

His Asn Tyr Tyr Phe Glu Lys Thr Leu Thr Thr Thr Val Val Leu Glu
            340                 345                 350
```

<210> SEQ ID NO 13
<211> LENGTH: 644
<212> TYPE: DNA
<213> ORGANISM: Artificial Sequence
<220> FEATURE:
<223> OTHER INFORMATION: Synthetic

<400> SEQUENCE: 13

```
gcggccatcg atgtcgacaa ctaacttaag ctagcaacgg tttccctcta gcgggatcaa     60

ttccgccccc ccccctaac gttactggcc gaagccgctt ggaataaggc cggtgtgcgt    120

ttgtctatat gttattttcc accatattgc cgtcttttgg caatgtgagg gcccggaaac    180

ctggccctgt cttcttgacg agcattccta ggggtctttc ccctctcgcc aaaggaatgc    240

aaggtctgtt gaatgtcgtg aaggaagcag ttcctctgga agcttcttga agacaaacaa    300

cgtctgtagc gaccctttgc aggcagcgga acccccacc tggcgacagg tgcctctgcg    360

gccaaaagcc acgtgtataa gatacacctg caaaggcggc acaaccccag tgccacgttg    420

tgagttggat agttgtggaa agagtcaaat ggctctcctc aagcgtattc aacaaggggc    480

tgaaggatgc ccagaaggta ccccattgta tgggatctga tctggggcct cggtgcacat    540

gctttacatg tgtttagtcg aggttaaaaa aacgtctagg ccccccgaac cacggggacg    600

tggttttcct ttgaaaaaca cgataatacc aattcgccgc cacc                    644
```

<210> SEQ ID NO 14
<211> LENGTH: 18
<212> TYPE: PRT
<213> ORGANISM: Artificial Sequence
<220> FEATURE:
<223> OTHER INFORMATION: Synthetic

<400> SEQUENCE: 14

```
Glu Gly Arg Gly Ser Leu Leu Thr Cys Gly Asp Val Glu Glu Asn Pro
1               5                   10                  15

Gly Pro
```

<210> SEQ ID NO 15
<211> LENGTH: 85
<212> TYPE: DNA
<213> ORGANISM: Artificial Sequence
<220> FEATURE:
<223> OTHER INFORMATION: Synthetic

<400> SEQUENCE: 15

```
atggcggatg tgtgacatac acgacgccaa aagattttgt tccagctcct gccacctccg     60

ctacgcgaga gattaaccac ccacg                                           85
```

<210> SEQ ID NO 16
<211> LENGTH: 805
<212> TYPE: DNA
<213> ORGANISM: Artificial Sequence
<220> FEATURE:
<223> OTHER INFORMATION: Synthetic

<400> SEQUENCE: 16

```
taataaccgg gcagggggga tcccgggtaa ttaattgaat tacatcccta cgcaaacgtt      60

ttacggccgc cggtggcgcc cgcgcccggc ggcccgtccc tggccgttgc aggccactcc     120

ggtggctccc gtcgtccccg acttccaggc ccagcagatg cagcaactca tcagcgccgt     180

aaatgcgctg acaatgagac agaacgcaat tgctcctgct aggcctccca aaccaaagaa     240

gaagaagaca accaaaccaa agccgaaaac gcagcccaag aagatcaacg gaaaaacgca     300

gcagcaaaag aagaaagaca agcaagccga caagaagaag aagaaacccg gaaaaagaga     360

aagaatgtgc atgaagattg aaaatgactg tatctatgcg gctagccaca gtaacgtagt     420

gtttccagac atgtcgggca ccgcactatc atgggtgcag aaaatctcgg gtggtctggg     480

ggccttcgca atcggcgcta tcctggtgct ggttgtggtc acttgcattg ggctccgcag     540

ataagttagg gtaggcaatg gcattgatat agcaagaaaa ttgaaaacag aaaaagttag     600

ggtaagcaat ggcatataac cataactgta taacttgtaa caaagcgcaa caagacctgc     660

gcaattggcc ccgtggtccg cctcacggaa actcggggca actcatattg acacattaat     720

tggcaataat tggaagctta cataagctta attcgacgaa taattggatt tttattttat     780

tttgcaattg gtttttaata tttcc                                           805
```

<210> SEQ ID NO 17
<211> LENGTH: 2432
<212> TYPE: PRT
<213> ORGANISM: Artificial Sequence
<220> FEATURE:
<223> OTHER INFORMATION: Synthetic

<400> SEQUENCE: 17

```
Met Ala Ala Lys Val His Val Asp Ile Glu Ala Asp Ser Pro Phe Ile
1               5                   10                  15

Lys Ser Leu Gln Lys Ala Phe Pro Ser Phe Glu Val Glu Ser Leu Gln
            20                  25                  30

Val Thr Pro Asn Asp His Ala Asn Ala Arg Ala Phe Ser His Leu Ala
        35                  40                  45

Thr Lys Leu Ile Glu Gln Glu Thr Asp Lys Asp Thr Leu Ile Leu Asp
    50                  55                  60

Ile Gly Ser Ala Pro Ser Arg Arg Met Met Ser Thr His Lys Tyr His
65                  70                  75                  80

Cys Val Cys Pro Met Arg Ser Ala Glu Asp Pro Glu Arg Leu Val Cys
                85                  90                  95

Tyr Ala Lys Lys Leu Ala Ala Ala Ser Gly Lys Val Leu Asp Arg Glu
            100                 105                 110

Ile Ala Gly Lys Ile Thr Asp Leu Gln Thr Val Met Ala Thr Pro Asp
        115                 120                 125

Ala Glu Ser Pro Thr Phe Cys Leu His Thr Asp Val Thr Cys Arg Thr
    130                 135                 140

Ala Ala Glu Val Ala Val Tyr Gln Asp Val Tyr Ala Val His Ala Pro
145                 150                 155                 160
```

-continued

```
Thr Ser Leu Tyr His Gln Ala Met Lys Gly Val Arg Thr Ala Tyr Trp
                165                 170                 175

Ile Gly Phe Asp Thr Thr Pro Phe Met Phe Asp Ala Leu Ala Gly Ala
            180                 185                 190

Tyr Pro Thr Tyr Ala Thr Asn Trp Ala Asp Glu Gln Val Leu Gln Ala
        195                 200                 205

Arg Asn Ile Gly Leu Cys Ala Ala Ser Leu Thr Glu Gly Arg Leu Gly
    210                 215                 220

Lys Leu Ser Ile Leu Arg Lys Lys Gln Leu Lys Pro Cys Asp Thr Val
225                 230                 235                 240

Met Phe Ser Val Gly Ser Thr Leu Tyr Thr Glu Ser Arg Lys Leu Leu
                245                 250                 255

Arg Ser Trp His Leu Pro Ser Val Phe His Leu Lys Gly Lys Gln Ser
            260                 265                 270

Phe Thr Cys Arg Cys Asp Thr Ile Val Ser Cys Glu Gly Tyr Val Val
        275                 280                 285

Lys Lys Ile Thr Met Cys Pro Gly Leu Tyr Gly Lys Thr Val Gly Tyr
    290                 295                 300

Ala Val Thr Tyr His Ala Glu Gly Phe Leu Val Cys Lys Thr Thr Asp
305                 310                 315                 320

Thr Val Lys Gly Glu Arg Val Ser Phe Pro Val Cys Thr Tyr Val Pro
                325                 330                 335

Ser Thr Ile Cys Asp Gln Met Thr Gly Ile Leu Ala Thr Asp Val Thr
            340                 345                 350

Pro Glu Asp Ala Gln Lys Leu Leu Val Gly Leu Asn Gln Arg Ile Val
        355                 360                 365

Val Asn Gly Arg Thr Gln Arg Asn Thr Asn Thr Met Lys Asn Tyr Leu
    370                 375                 380

Leu Pro Ile Val Ala Val Ala Phe Ser Lys Trp Ala Arg Glu Tyr Lys
385                 390                 395                 400

Ala Asp Leu Asp Asp Glu Lys Pro Leu Gly Val Arg Glu Arg Ser Leu
                405                 410                 415

Thr Cys Cys Cys Leu Trp Ala Phe Lys Thr Arg Lys Met His Thr Met
            420                 425                 430

Tyr Lys Lys Pro Asp Thr Gln Thr Ile Val Lys Val Pro Ser Glu Phe
        435                 440                 445

Asn Ser Phe Val Ile Pro Ser Leu Trp Ser Thr Gly Leu Ala Ile Pro
    450                 455                 460

Val Arg Ser Arg Ile Lys Met Leu Leu Ala Lys Lys Thr Lys Arg Glu
465                 470                 475                 480

Leu Ile Pro Val Leu Asp Ala Ser Ser Ala Arg Asp Ala Glu Gln Glu
                485                 490                 495

Glu Lys Glu Arg Leu Glu Ala Glu Leu Thr Arg Glu Ala Leu Pro Pro
            500                 505                 510

Leu Val Pro Ile Ala Pro Ala Glu Thr Gly Val Val Asp Val Asp Val
        515                 520                 525

Glu Glu Leu Glu Tyr His Ala Gly Ala Gly Val Val Glu Thr Pro Arg
    530                 535                 540

Ser Ala Leu Lys Val Thr Ala Gln Pro Asn Asp Val Leu Leu Gly Asn
545                 550                 555                 560

Tyr Val Val Leu Ser Pro Gln Thr Val Leu Lys Ser Ser Lys Leu Ala
                565                 570                 575

Pro Val His Pro Leu Ala Glu Gln Val Lys Ile Ile Thr His Asn Gly
```

```
            580                 585                 590

Arg Ala Gly Arg Tyr Gln Val Asp Gly Tyr Asp Gly Arg Val Leu Leu
        595                 600                 605

Pro Cys Gly Ser Ala Ile Pro Val Pro Glu Phe Gln Ala Leu Ser Glu
    610                 615                 620

Ser Ala Thr Met Val Tyr Asn Glu Arg Glu Phe Val Asn Arg Lys Leu
625                 630                 635                 640

Tyr His Ile Ala Val His Gly Pro Ser Leu Asn Thr Asp Glu Glu Asn
                645                 650                 655

Tyr Glu Lys Val Arg Ala Glu Arg Thr Asp Ala Glu Tyr Val Phe Asp
            660                 665                 670

Val Asp Lys Lys Cys Cys Val Lys Arg Glu Glu Ala Ser Gly Leu Val
        675                 680                 685

Leu Val Gly Glu Leu Thr Asn Pro Pro Phe His Glu Phe Ala Tyr Glu
    690                 695                 700

Gly Leu Lys Ile Arg Pro Ser Ala Pro Tyr Lys Thr Thr Val Val Gly
705                 710                 715                 720

Val Phe Gly Val Pro Gly Ser Gly Lys Ser Ala Ile Ile Lys Ser Leu
                725                 730                 735

Val Thr Lys His Asp Leu Val Thr Ser Gly Lys Lys Glu Asn Cys Gln
            740                 745                 750

Glu Ile Val Asn Asp Val Lys Lys His Arg Gly Leu Asp Ile Gln Ala
        755                 760                 765

Lys Thr Val Asp Ser Ile Leu Leu Asn Gly Cys Arg Arg Ala Val Asp
    770                 775                 780

Ile Leu Tyr Val Asp Glu Ala Phe Ala Cys His Ser Gly Thr Leu Leu
785                 790                 795                 800

Ala Leu Ile Ala Leu Val Lys Pro Arg Ser Lys Val Val Leu Cys Gly
                805                 810                 815

Asp Pro Lys Gln Cys Gly Phe Phe Asn Met Met Gln Leu Lys Val Asn
            820                 825                 830

Phe Asn His Asn Ile Cys Thr Glu Val Cys His Lys Ser Ile Ser Arg
        835                 840                 845

Arg Cys Thr Arg Pro Val Thr Ala Ile Val Ser Thr Leu His Tyr Gly
    850                 855                 860

Gly Lys Met Arg Thr Thr Asn Pro Cys Asn Lys Pro Ile Ile Ile Asp
865                 870                 875                 880

Thr Thr Gly Gln Thr Lys Pro Lys Pro Gly Asp Ile Val Leu Thr Cys
                885                 890                 895

Phe Arg Gly Trp Val Lys Gln Leu Gln Leu Asp Tyr Arg Gly His Glu
            900                 905                 910

Val Met Thr Ala Ala Ala Ser Gln Gly Leu Thr Arg Lys Gly Val Tyr
        915                 920                 925

Ala Val Arg Gln Lys Val Asn Glu Asn Pro Leu Tyr Ala Pro Ala Ser
    930                 935                 940

Glu His Val Asn Val Leu Leu Thr Arg Thr Glu Asp Arg Leu Val Trp
945                 950                 955                 960

Lys Thr Leu Ala Gly Asp Pro Trp Ile Lys Val Leu Ser Asn Ile Pro
                965                 970                 975

Gln Gly Asn Phe Thr Ala Thr Leu Glu Glu Trp Gln Glu Glu His Asp
            980                 985                 990

Lys Ile Met Lys Val Ile Glu Gly  Pro Ala Ala Pro Val  Asp Ala Phe
        995                 1000                 1005
```

```
Gln Asn  Lys Ala Asn Val Cys  Trp Ala Lys Ser Leu  Val Pro Val
    1010                 1015                 1020

Leu Asp  Thr Ala Gly Ile Arg  Leu Thr Ala Glu Glu  Trp Ser Thr
    1025                 1030                 1035

Ile Ile  Thr Ala Phe Lys Glu  Asp Arg Ala Tyr Ser  Pro Val Val
    1040                 1045                 1050

Ala Leu  Asn Glu Ile Cys Thr  Lys Tyr Tyr Gly Val  Asp Leu Asp
    1055                 1060                 1065

Ser Gly  Leu Phe Ser Ala Pro  Lys Val Ser Leu Tyr  Tyr Glu Asn
    1070                 1075                 1080

Asn His  Trp Asp Asn Arg Pro  Gly Gly Arg Met Tyr  Gly Phe Asn
    1085                 1090                 1095

Ala Ala  Thr Ala Ala Arg Leu  Glu Ala Arg His Thr  Phe Leu Lys
    1100                 1105                 1110

Gly Gln  Trp His Thr Gly Lys  Gln Ala Val Ile Ala  Glu Arg Lys
    1115                 1120                 1125

Ile Gln  Pro Leu Ser Val Leu  Asp Asn Val Ile Pro  Ile Asn Arg
    1130                 1135                 1140

Arg Leu  Pro His Ala Leu Val  Ala Glu Tyr Lys Thr  Val Lys Gly
    1145                 1150                 1155

Ser Arg  Val Glu Trp Leu Val  Asn Lys Val Arg Gly  Tyr His Val
    1160                 1165                 1170

Leu Leu  Val Ser Glu Tyr Asn  Leu Ala Leu Pro Arg  Arg Arg Val
    1175                 1180                 1185

Thr Trp  Leu Ser Pro Leu Asn  Val Thr Gly Ala Asp  Arg Cys Tyr
    1190                 1195                 1200

Asp Leu  Ser Leu Gly Leu Pro  Ala Asp Ala Gly Arg  Phe Asp Leu
    1205                 1210                 1215

Val Phe  Val Asn Ile His Thr  Glu Phe Arg Ile His  His Tyr Gln
    1220                 1225                 1230

Gln Cys  Val Asp His Ala Met  Lys Leu Gln Met Leu  Gly Gly Asp
    1235                 1240                 1245

Ala Leu  Arg Leu Leu Lys Pro  Gly Gly Ser Leu Leu  Met Arg Ala
    1250                 1255                 1260

Tyr Gly  Tyr Ala Asp Lys Ile  Ser Glu Ala Val Val  Ser Ser Leu
    1265                 1270                 1275

Ser Arg  Lys Phe Ser Ser Ala  Arg Val Leu Arg Pro  Asp Cys Val
    1280                 1285                 1290

Thr Ser  Asn Thr Glu Val Phe  Leu Leu Phe Ser Asn  Phe Asp Asn
    1295                 1300                 1305

Gly Lys  Arg Pro Ser Thr Leu  His Gln Met Asn Thr  Lys Leu Ser
    1310                 1315                 1320

Ala Val  Tyr Ala Gly Glu Ala  Met His Thr Ala Gly  Cys Ala Pro
    1325                 1330                 1335

Ser Tyr  Arg Val Lys Arg Ala  Asp Ile Ala Thr Cys  Thr Glu Ala
    1340                 1345                 1350

Ala Val  Val Asn Ala Ala Asn  Ala Arg Gly Thr Val  Gly Asp Gly
    1355                 1360                 1365

Val Cys  Arg Ala Val Ala Lys  Lys Trp Pro Ser Ala  Phe Lys Gly
    1370                 1375                 1380

Glu Ala  Thr Pro Val Gly Thr  Ile Lys Thr Val Met  Cys Gly Ser
    1385                 1390                 1395
```

-continued

```
Tyr Pro  Val Ile His Ala Val  Ala Pro Asn Phe Ser  Ala Thr Thr
    1400                 1405                 1410

Glu Ala  Glu Gly Asp Arg Glu  Leu Ala Ala Val Tyr  Arg Ala Val
    1415                 1420                 1425

Ala Ala  Glu Val Asn Arg Leu  Ser Leu Ser Ser Val  Ala Ile Pro
    1430                 1435                 1440

Leu Leu  Ser Thr Gly Val Phe  Ser Gly Gly Arg Asp  Arg Leu Gln
    1445                 1450                 1455

Gln Ser  Leu Asn His Leu Phe  Thr Ala Met Asp Ala  Thr Asp Ala
    1460                 1465                 1470

Asp Val  Thr Ile Tyr Cys Arg  Asp Lys Ser Trp Glu  Lys Lys Ile
    1475                 1480                 1485

Gln Glu  Ala Ile Asp Met Arg  Thr Ala Val Glu Leu  Leu Asn Asp
    1490                 1495                 1500

Asp Val  Glu Leu Thr Thr Asp  Leu Val Arg Val His  Pro Asp Ser
    1505                 1510                 1515

Ser Leu  Val Gly Arg Lys Gly  Tyr Ser Thr Thr Asp  Gly Ser Leu
    1520                 1525                 1530

Tyr Ser  Tyr Phe Glu Gly Thr  Lys Phe Asn Gln Ala  Ala Ile Asp
    1535                 1540                 1545

Met Ala  Glu Ile Leu Thr Leu  Trp Pro Arg Leu Gln  Glu Ala Asn
    1550                 1555                 1560

Glu Gln  Ile Cys Leu Tyr Ala  Leu Gly Glu Thr Met  Asp Asn Ile
    1565                 1570                 1575

Arg Ser  Lys Cys Pro Val Asn  Asp Ser Asp Ser Ser  Thr Pro Pro
    1580                 1585                 1590

Arg Thr  Val Pro Cys Leu Cys  Arg Tyr Ala Met Thr  Ala Glu Arg
    1595                 1600                 1605

Ile Ala  Arg Leu Arg Ser His  Gln Val Lys Ser Met  Val Val Cys
    1610                 1615                 1620

Ser Ser  Phe Pro Leu Pro Lys  Tyr His Val Asp Gly  Val Gln Lys
    1625                 1630                 1635

Val Lys  Cys Glu Lys Val Leu  Leu Phe Asp Pro Thr  Val Pro Ser
    1640                 1645                 1650

Val Val  Ser Pro Arg Lys Tyr  Ala Ala Ser Thr Thr  Asp His Ser
    1655                 1660                 1665

Asp Arg  Ser Leu Arg Gly Phe  Asp Leu Asp Trp Thr  Thr Asp Ser
    1670                 1675                 1680

Ser Ser  Thr Ala Ser Asp Thr  Met Ser Leu Pro Ser  Leu Gln Ser
    1685                 1690                 1695

Cys Asp  Ile Asp Ser Ile Tyr  Glu Pro Met Ala Pro  Ile Val Val
    1700                 1705                 1710

Thr Ala  Asp Val His Pro Glu  Pro Ala Gly Ile Ala  Asp Leu Ala
    1715                 1720                 1725

Ala Asp  Val His Pro Glu Pro  Ala Asp His Val Asp  Leu Glu Asn
    1730                 1735                 1740

Pro Ile  Pro Pro Pro Arg Pro  Lys Arg Ala Ala Tyr  Leu Ala Ser
    1745                 1750                 1755

Arg Ala  Ala Glu Arg Pro Val  Pro Ala Pro Arg Lys  Pro Thr Pro
    1760                 1765                 1770

Ala Pro  Arg Thr Ala Phe Arg  Asn Lys Leu Pro Leu  Thr Phe Gly
    1775                 1780                 1785

Asp Phe  Asp Glu His Glu Val  Asp Ala Leu Ala Ser  Gly Ile Thr
```

```
    1790                1795                1800

Phe Gly  Asp Phe Asp Asp Val  Leu Arg Leu Gly Arg  Ala Gly Ala
    1805                1810                1815

Tyr Ile  Phe Ser Ser Asp Thr  Gly Ser Gly His Leu  Gln Gln Lys
    1820                1825                1830

Ser Val  Arg Gln His Asn Leu  Gln Cys Ala Gln Leu  Asp Ala Val
    1835                1840                1845

Glu Glu  Glu Lys Met Tyr Pro  Pro Lys Leu Asp Thr  Glu Arg Glu
    1850                1855                1860

Lys Leu  Leu Leu Leu Lys Met  Gln Met His Pro Ser  Glu Ala Asn
    1865                1870                1875

Lys Ser  Arg Tyr Gln Ser Arg  Lys Val Glu Asn Met  Lys Ala Thr
    1880                1885                1890

Val Val  Asp Arg Leu Thr Ser  Gly Ala Arg Leu Tyr  Thr Gly Ala
    1895                1900                1905

Asp Val  Gly Arg Ile Pro Thr  Tyr Ala Val Arg Tyr  Pro Arg Pro
    1910                1915                1920

Val Tyr  Ser Pro Thr Val Ile  Glu Arg Phe Ser Ser  Pro Asp Val
    1925                1930                1935

Ala Ile  Ala Ala Cys Asn Glu  Tyr Leu Ser Arg Asn  Tyr Pro Thr
    1940                1945                1950

Val Ala  Ser Tyr Gln Ile Thr  Asp Glu Tyr Asp Ala  Tyr Leu Asp
    1955                1960                1965

Met Val  Asp Gly Ser Asp Ser  Cys Leu Asp Arg Ala  Thr Phe Cys
    1970                1975                1980

Pro Ala  Lys Leu Arg Cys Tyr  Pro Lys His His Ala  Tyr His Gln
    1985                1990                1995

Pro Thr  Val Arg Ser Ala Val  Pro Ser Pro Phe Gln  Asn Thr Leu
    2000                2005                2010

Gln Asn  Val Leu Ala Ala Ala  Thr Lys Arg Asn Cys  Asn Val Thr
    2015                2020                2025

Gln Met  Arg Glu Leu Pro Thr  Met Asp Ser Ala Val  Phe Asn Val
    2030                2035                2040

Glu Cys  Phe Lys Arg Tyr Ala  Cys Ser Gly Glu Tyr  Trp Glu Glu
    2045                2050                2055

Tyr Ala  Lys Gln Pro Ile Arg  Ile Thr Thr Glu Asn  Ile Thr Thr
    2060                2065                2070

Tyr Val  Thr Lys Leu Lys Gly  Pro Lys Ala Ala Ala  Leu Phe Ala
    2075                2080                2085

Lys Thr  His Asn Leu Val Pro  Leu Gln Glu Val Pro  Met Asp Arg
    2090                2095                2100

Phe Thr  Val Asp Met Lys Arg  Asp Val Lys Val Thr  Pro Gly Thr
    2105                2110                2115

Lys His  Thr Glu Glu Arg Pro  Lys Val Gln Val Ile  Gln Ala Ala
    2120                2125                2130

Glu Pro  Leu Ala Thr Ala Tyr  Leu Cys Gly Ile His  Arg Glu Leu
    2135                2140                2145

Val Arg  Arg Leu Asn Ala Val  Leu Arg Pro Asn Val  His Thr Leu
    2150                2155                2160

Phe Asp  Met Ser Ala Glu Asp  Phe Asp Ala Ile Ile  Ala Ser His
    2165                2170                2175

Phe His  Pro Gly Asp Pro Val  Leu Glu Thr Asp Ile  Ala Ser Phe
    2180                2185                2190
```

```
Asp Lys  Ser Gln Asp Asp Ser  Leu Ala Leu Thr Gly  Leu Met Ile
    2195                 2200                 2205

Leu Glu  Asp Leu Gly Val Asp  Gln Tyr Leu Leu Asp  Leu Ile Glu
    2210                 2215                 2220

Ala Ala  Phe Gly Glu Ile Ser  Ser Cys His Leu Pro  Thr Gly Thr
    2225                 2230                 2235

Arg Phe  Lys Phe Gly Ala Met  Met Lys Ser Gly Met  Phe Leu Thr
    2240                 2245                 2250

Leu Phe  Ile Asn Thr Val Leu  Asn Ile Thr Ile Ala  Ser Arg Val
    2255                 2260                 2265

Leu Glu  Gln Arg Leu Thr Asp  Ser Ala Cys Ala Ala  Phe Ile Gly
    2270                 2275                 2280

Asp Asp  Asn Ile Val His Gly  Val Ile Ser Asp Lys  Leu Met Ala
    2285                 2290                 2295

Glu Arg  Cys Ala Ser Trp Val  Asn Met Glu Val Lys  Ile Ile Asp
    2300                 2305                 2310

Ala Val  Met Gly Glu Lys Pro  Pro Tyr Phe Cys Gly  Gly Phe Ile
    2315                 2320                 2325

Val Phe  Asp Ser Val Thr Gln  Thr Ala Cys Arg Val  Ser Asp Pro
    2330                 2335                 2340

Leu Lys  Arg Leu Phe Lys Leu  Gly Lys Pro Leu Thr  Ala Glu Asp
    2345                 2350                 2355

Lys Gln  Asp Glu Asp Arg Arg  Arg Ala Leu Ser Asp  Glu Val Ser
    2360                 2365                 2370

Lys Trp  Phe Arg Thr Gly Leu  Gly Ala Glu Leu Glu  Val Ala Leu
    2375                 2380                 2385

Thr Ser  Arg Tyr Glu Val Glu  Gly Cys Lys Ser Ile  Leu Ile Ala
    2390                 2395                 2400

Met Ala  Thr Leu Ala Arg Asp  Ile Lys Ala Phe Lys  Lys Leu Arg
    2405                 2410                 2415

Gly Pro  Val Ile His Leu Tyr  Gly Gly Pro Arg Leu  Val Arg
    2420                 2425                 2430
```

<210> SEQ ID NO 18
<211> LENGTH: 125
<212> TYPE: DNA
<213> ORGANISM: Artificial Sequence
<220> FEATURE:
<223> OTHER INFORMATION: Synthetic

<400> SEQUENCE: 18

```
tacacagaat tctgattata gcgcactatt atagcaccat gaattacatc cctacgcaaa     60

cgttttacgg ccgccggtgg cgcccgcgcc cggcggcccg tccctggccg ttgcaggcca    120

ctccg                                                                125
```

<210> SEQ ID NO 19
<211> LENGTH: 240
<212> TYPE: PRT
<213> ORGANISM: Artificial Sequence
<220> FEATURE:
<223> OTHER INFORMATION: Synthetic

<400> SEQUENCE: 19

```
Val Ala Pro Val Val Pro Asp Phe Gln Ala Gln Gln Met Gln Gln Leu
1               5                   10                  15

Ile Ser Ala Val Asn Ala Leu Thr Met Arg Gln Asn Ala Ile Ala Pro
```

```
            20                  25                  30

Ala Arg Pro Pro Lys Pro Lys Lys Lys Lys Thr Thr Lys Pro Lys Pro
        35                  40                  45

Lys Thr Gln Pro Lys Lys Ile Asn Gly Lys Thr Gln Gln Gln Lys Lys
    50                  55                  60

Lys Asp Lys Gln Ala Asp Lys Lys Lys Lys Lys Pro Gly Lys Arg Glu
65                  70                  75                  80

Arg Met Cys Met Lys Ile Glu Asn Asp Cys Ile Phe Glu Val Lys His
                85                  90                  95

Glu Gly Lys Val Thr Gly Tyr Ala Cys Leu Val Gly Asp Lys Val Met
            100                 105                 110

Lys Pro Ala His Val Lys Gly Val Ile Asp Asn Ala Asp Leu Ala Lys
        115                 120                 125

Leu Ala Phe Lys Lys Ser Ser Lys Tyr Asp Leu Glu Cys Ala Gln Ile
    130                 135                 140

Pro Val His Met Arg Ser Asp Ala Ser Lys Tyr Thr His Glu Lys Pro
145                 150                 155                 160

Glu Gly His Tyr Asn Trp His His Gly Ala Val Gln Tyr Ser Gly Gly
                165                 170                 175

Arg Phe Thr Ile Pro Thr Gly Ala Gly Lys Pro Gly Asp Ser Gly Arg
            180                 185                 190

Pro Ile Phe Asp Asn Lys Gly Arg Val Val Ala Ile Val Leu Gly Gly
        195                 200                 205

Ala Asn Glu Gly Ser Arg Thr Ala Leu Ser Val Val Thr Trp Asn Lys
    210                 215                 220

Asp Met Val Thr Arg Val Thr Pro Glu Gly Ser Glu Glu Trp Asp Pro
225                 230                 235                 240


<210> SEQ ID NO 20
<211> LENGTH: 13
<212> TYPE: DNA
<213> ORGANISM: Artificial Sequence
<220> FEATURE:
<223> OTHER INFORMATION: Synthetic

<400> SEQUENCE: 20

gccgccacca tga                                                          13


<210> SEQ ID NO 21
<211> LENGTH: 516
<212> TYPE: PRT
<213> ORGANISM: Artificial Sequence
<220> FEATURE:
<223> OTHER INFORMATION: Synthetic

<400> SEQUENCE: 21

Met Tyr Arg Met Gln Leu Leu Ser Cys Ile Ala Leu Ser Leu Ala Leu
1               5                   10                  15

Val Thr Asn Ser Asp Ile Val Leu Thr Gln Ser Pro Ala Ser Leu Ala
            20                  25                  30

Val Ser Pro Gly Gln Arg Ala Thr Ile Thr Cys Arg Ala Ser Glu Ser
        35                  40                  45

Val Ser Phe Leu Gly Ile Asn Leu Ile His Trp Tyr Gln Gln Lys Pro
    50                  55                  60

Gly Gln Pro Pro Lys Leu Leu Ile Tyr Ser Ala Ser Asn Leu Gln Ser
65                  70                  75                  80

Gly Val Pro Ala Arg Phe Ser Gly Ser Gly Ser Gly Thr Asp Phe Thr
```

```
                85                  90                  95

Leu Thr Ile Ser Ser Val Glu Pro Glu Asp Thr Ala Asn Tyr Tyr Cys
            100                 105                 110

Leu Gln Ser Arg Thr Leu Pro Arg Thr Phe Gly Gln Gly Thr Lys Val
        115                 120                 125

Glu Ile Lys Gly Ser Thr Ser Gly Ser Gly Lys Pro Gly Ser Gly Glu
    130                 135                 140

Gly Ser Thr Lys Gly Gln Ile Gln Leu Val Gln Ser Gly Pro Glu Leu
145                 150                 155                 160

Lys Lys Pro Gly Gly Ser Val Lys Ile Ser Cys Lys Ala Ser Gly Tyr
                165                 170                 175

Thr Phe Thr Ser Tyr Ser Ile Asn Trp Val Arg Gln Ala Pro Gly Lys
            180                 185                 190

Gly Leu Glu Trp Val Gly Trp Ile Asn Thr Glu Thr Arg Glu Pro Ala
        195                 200                 205

Tyr Ala Gln Gly Phe Thr Gly Arg Phe Thr Phe Ser Ala Asp Thr Ser
    210                 215                 220

Lys Ser Met Ala Tyr Leu Gln Ile Asn Ser Leu Arg Ala Glu Asp Thr
225                 230                 235                 240

Ala Val Tyr Tyr Cys Ala Leu Asp Tyr Leu Tyr Ser Leu Asp Phe Trp
                245                 250                 255

Gly Gln Gly Thr Leu Val Thr Val Ser Ser Gly Gly Gly Gly Ser Gln
            260                 265                 270

Val Gln Leu Val Gln Ser Gly Ala Glu Val Lys Lys Pro Gly Ala Ser
        275                 280                 285

Val Lys Val Ser Cys Lys Ala Ser Gly Tyr Thr Phe Thr Arg Tyr Thr
    290                 295                 300

Met His Trp Val Arg Gln Ala Pro Gly Gln Gly Leu Glu Trp Ile Gly
305                 310                 315                 320

Tyr Ile Asn Pro Ser Lys Gly Tyr Thr Asn Tyr Asn Gln Lys Phe Lys
                325                 330                 335

Gly Arg Val Thr Met Thr Ala Asp Lys Ser Thr Ser Thr Ala Tyr Met
            340                 345                 350

Glu Leu Ser Ser Leu Arg Ser Glu Asp Thr Ala Val Tyr Tyr Cys Ala
        355                 360                 365

Arg Tyr Tyr Asp Asp His Tyr Ser Leu Asp Tyr Trp Gly Gln Gly Thr
    370                 375                 380

Leu Val Thr Val Ser Ser Gly Gly Gly Gly Ser Gly Gly Gly Gly Ser
385                 390                 395                 400

Gly Gly Gly Gly Ser Gly Gly Gly Gly Ser Glu Ile Val Met Thr Gln
                405                 410                 415

Ser Pro Ala Thr Leu Ser Val Ser Pro Gly Glu Arg Ala Thr Leu Ser
            420                 425                 430

Cys Arg Ala Ser Ser Ser Val Ser Tyr Leu Asn Trp Tyr Gln Gln Lys
        435                 440                 445

Ser Gly Thr Ser Pro Lys Arg Trp Ile Tyr Asp Thr Ser Lys Val Ala
    450                 455                 460

Ser Gly Val Pro Tyr Arg Phe Ser Gly Ser Gly Ser Gly Thr Asp Phe
465                 470                 475                 480

Thr Leu Thr Ile Ser Ser Leu Gln Ala Glu Asp Glu Ala Thr Tyr Tyr
                485                 490                 495

Cys Gln Gln Trp Ser Ser Asn Pro Leu Thr Phe Gly Gln Gly Thr Lys
            500                 505                 510
```

```
Leu Glu Ile Lys
        515


<210> SEQ ID NO 22
<211> LENGTH: 496
<212> TYPE: PRT
<213> ORGANISM: Artificial Sequence
<220> FEATURE:
<223> OTHER INFORMATION: Synthetic

<400> SEQUENCE: 22

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Phe Leu
            20                  25                  30

Gly Ile Asn Leu Ile His Trp Tyr Gln Gln Lys Pro Gly Gln Pro Pro
        35                  40                  45

Lys Leu Leu Ile Tyr Ser Ala Ser Asn Leu Gln Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Thr Ala Asn Tyr Tyr Cys Leu Gln Ser Arg
                85                  90                  95

Thr Leu Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Gly Ser Val Lys Ile Ser Cys Lys Ala Ser Gly Tyr Thr Phe Thr Ser
145                 150                 155                 160

Tyr Ser Ile Asn Trp Val Arg Gln Ala Pro Gly Lys Gly Leu Glu Trp
                165                 170                 175

Val Gly Trp Ile Asn Thr Glu Thr Arg Glu Pro Ala Tyr Ala Gln Gly
            180                 185                 190

Phe Thr Gly Arg Phe Thr Phe Ser Ala Asp Thr Ser Lys Ser Met Ala
        195                 200                 205

Tyr Leu Gln Ile Asn Ser Leu Arg Ala Glu Asp Thr Ala Val Tyr Tyr
    210                 215                 220

Cys Ala Leu Asp Tyr Leu Tyr Ser Leu Asp Phe Trp Gly Gln Gly Thr
225                 230                 235                 240

Leu Val Thr Val Ser Ser Gly Gly Gly Gly Ser Gln Val Gln Leu Val
                245                 250                 255

Gln Ser Gly Ala Glu Val Lys Lys Pro Gly Ala Ser Val Lys Val Ser
            260                 265                 270

Cys Lys Ala Ser Gly Tyr Thr Phe Thr Arg Tyr Thr Met His Trp Val
        275                 280                 285

Arg Gln Ala Pro Gly Gln Gly Leu Glu Trp Ile Gly Tyr Ile Asn Pro
    290                 295                 300

Ser Lys Gly Tyr Thr Asn Tyr Asn Gln Lys Phe Lys Gly Arg Val Thr
305                 310                 315                 320

Met Thr Ala Asp Lys Ser Thr Ser Thr Ala Tyr Met Glu Leu Ser Ser
                325                 330                 335

Leu Arg Ser Glu Asp Thr Ala Val Tyr Tyr Cys Ala Arg Tyr Tyr Asp
            340                 345                 350
```

```
Asp His Tyr Ser Leu Asp Tyr Trp Gly Gln Gly Thr Leu Val Thr Val
        355                 360                 365

Ser Ser Gly Gly Gly Gly Ser Gly Gly Gly Gly Ser Gly Gly Gly Gly
    370                 375                 380

Ser Gly Gly Gly Gly Ser Glu Ile Val Met Thr Gln Ser Pro Ala Thr
385                 390                 395                 400

Leu Ser Val Ser Pro Gly Glu Arg Ala Thr Leu Ser Cys Arg Ala Ser
                405                 410                 415

Ser Ser Val Ser Tyr Leu Asn Trp Tyr Gln Gln Lys Ser Gly Thr Ser
            420                 425                 430

Pro Lys Arg Trp Ile Tyr Asp Thr Ser Lys Val Ala Ser Gly Val Pro
        435                 440                 445

Tyr Arg Phe Ser Gly Ser Gly Ser Gly Thr Asp Phe Thr Leu Thr Ile
    450                 455                 460

Ser Ser Leu Gln Ala Glu Asp Glu Ala Thr Tyr Tyr Cys Gln Gln Trp
465                 470                 475                 480

Ser Ser Asn Pro Leu Thr Phe Gly Gln Gly Thr Lys Leu Glu Ile Lys
                485                 490                 495
```

<210> SEQ ID NO 23
<211> LENGTH: 52
<212> TYPE: DNA
<213> ORGANISM: Artificial Sequence
<220> FEATURE:
<223> OTHER INFORMATION: Synthetic

<400> SEQUENCE: 23

```
agacccaagc tggctagctc taaagaagcc cctgggagca cagctcatca cc             52
```

<210> SEQ ID NO 24
<211> LENGTH: 218
<212> TYPE: DNA
<213> ORGANISM: Artificial Sequence
<220> FEATURE:
<223> OTHER INFORMATION: Synthetic

<400> SEQUENCE: 24

```
ctatgaagaa ggaaggcatc cagaccagaa accgaaaaat gtctagcaaa tccaaaaagt     60

gcaaaaaagt gcatgactca ctggaggact tccccaagaa cagctcgttt aacccggccg    120

ccctctccag acacatgtcc tccctgagcc acatctcgcc cttcagccac tccagccaca    180

tgctgaccac gcccacgccg atgcacccgc catccagc                            218
```

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25

```
agctggctag ctctaaagaa gc                                              22
```

<210> SEQ ID NO 26
<211> LENGTH: 26
<212> TYPE: DNA
<213> ORGANISM: Artificial Sequence
<220> FEATURE:
<223> OTHER INFORMATION: Synthetic

<400> SEQUENCE: 26

```
tctccgaatg tctggatatt aaaggc                                            26


<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27

aagcaacagc gtcttcgac                                                    19


<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28

atctttgtag tcagagccgc c                                                 21
```